United States Patent
Bonnet et al.

(10) Patent No.: US 11,046,657 B2
(45) Date of Patent: Jun. 29, 2021

(54) PYRIMIDINONE DERIVATIVES AND USES THEREOF TO NEUTRALIZE THE BIOLOGICAL ACTIVITY OF CHEMOKINES

(71) Applicants: Centre National de la Recherche Scientifique (CNRS), Paris (FR); Institute National de la Santé et de la Recherche Médicale (INSERM), Paris (FR); Université de Strasbourg, Strasbourg (FR); Universite Paris-Sud, Orsay (FR); Centre International de Recherche aux Frontieres de la Chimie, Strasbourg (FR)

(72) Inventors: Dominique Bonnet, Geispolsheim (FR); Nelly Frossard, Strasbourg (FR); Jean-Luc Galzi, Weitbruch (FR); Christophe Guignabert, Arcueil (FR); Marcel Hibert, Eschau (FR); Frédéric Simonin, Gresswiller (FR); Sylviane Muller, Strasbourg (FR)

(73) Assignees: Centre National de la Recherche Scientifique, Paris (FR); Institut National de la Sante et de la Recherche Medicale, Paris (FR); Universite de Strasbourg, Strasbourg (FR); Universite Paris-Sud, Orsay (FR); Centre International de Recherche aux Frontieres de la Chimie, Strasbourg (FR)

( * ) Notice: Subject to any disclaimer, the term of this patent is extended or adjusted under 35 U.S.C. 154(b) by 43 days.

(21) Appl. No.: 16/316,614

(22) PCT Filed: Jul. 13, 2017

(86) PCT No.: PCT/EP2017/067775
§ 371 (c)(1),
(2) Date: Jan. 9, 2019

(87) PCT Pub. No.: WO2018/011376
PCT Pub. Date: Jan. 18, 2018

(65) Prior Publication Data
US 2020/0181093 A1    Jun. 11, 2020

(30) Foreign Application Priority Data
Jul. 13, 2016   (EP) ..................................... 16305908

(51) Int. Cl.
| C07D 239/36 | (2006.01) |
| C07D 403/10 | (2006.01) |
| C07D 413/10 | (2006.01) |
| C07D 401/04 | (2006.01) |
| C07D 405/04 | (2006.01) |
| C07D 417/04 | (2006.01) |
| C07D 409/04 | (2006.01) |
| C07D 403/04 | (2006.01) |

(Continued)

(52) U.S. Cl.
CPC ............ *C07D 239/36* (2013.01); *A61P 29/00* (2018.01); *A61P 35/00* (2018.01); *C07D 401/04* (2013.01); *C07D 403/04* (2013.01); *C07D 403/10* (2013.01); *C07D 405/04* (2013.01); *C07D 409/04* (2013.01); *C07D 413/04* (2013.01); *C07D 413/10* (2013.01); *C07D 417/04* (2013.01)

(58) Field of Classification Search
CPC .. C07D 239/36; C07D 403/04; C07D 403/10; C07D 413/04; C07D 413/10; C07D 401/04; C07D 405/04; C07D 417/04; C07D 409/04; A61P 29/00; A61P 35/10
USPC ......................................................... 514/235
See application file for complete search history.

(56) References Cited

U.S. PATENT DOCUMENTS

2009/0215803 A1*   8/2009   Rice ........................ A61P 43/00
                                                                            514/274

OTHER PUBLICATIONS

International Search Report issued in corresponding International Patent Application No. PCT/EP2017/067775 dated Sep. 25, 2017.

(Continued)

*Primary Examiner* — Tracy Vivlemore
*Assistant Examiner* — Ebenezer O Sackey
(74) *Attorney, Agent, or Firm* — Morgan, Lewis & Bockius LLP

(57) ABSTRACT

A subject of the present invention is a compound having the general formula (I):

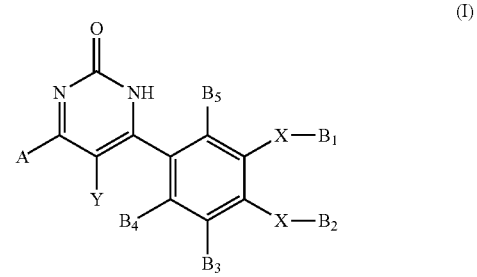

a pharmaceutically acceptable salt thereof or a tautomeric form thereof,
wherein A, $B_3$, $B_4$, $B_5$, Y, X, $B_1$ and $B_2$ are as defined in any one of claims 1 to 10.
Another subject of the invention is the compound as defined above for use as a medicament, in particular for preventing and/or treating inflammation and inflammatory diseases, immune and auto-immune diseases, pain related diseases, genetic diseases and/or cancer.

16 Claims, 5 Drawing Sheets

(51) Int. Cl.
    *C07D 413/04*    (2006.01)
    *A61P 29/00*     (2006.01)
    *A61P 35/00*     (2006.01)

(56)             References Cited

OTHER PUBLICATIONS

Dinakaran et al., "Synthesis and biological evaluation of novel pyrimidine-2(1H)-ones/thiones as potent anti-inflammatory and anti-cancer agents," Medicinal Chemistry Research, 21: 3598-3606 (2012).
Liang-Ce et al., "An Efficient and Facile Synthesis of 5-(Thiophene-2-carbonyl)-6-(trifluoromethyl)-tetrahydro-pyrimidin-2(1H)-one and 6-(Thiophen-2-yl)-4,5-dihydropyrimidin-2(1H)-one from Same Substrates Under Different Conditions," Journal of Heterocyclic Chemistry, 53: 56-63 (2016).
Jayaramu et al., "Synthesis and in vitro biological activities of chalcones and their heterocyclic derivatives," Der Pharma Chemica, 7: 30-35 (2015).
Kundariya et al., "Synthesis towards 4,6-Disubstituted Pyrimidines via Chalcone Derivatives and Their Biological Evaluation," Research Journal of Pharmaceutical, Biological and Chemical Sciences, 3: 325-337 (2012).
Written Opinion issued in corresponding International Patent Application No. PCT/EP2017/067775 dated Sep. 25, 2017.

\* cited by examiner (Scale bar = 50 μm)

(Scale bar = 50 μm)

PYRIMIDINONE DERIVATIVES AND USES THEREOF TO NEUTRALIZE THE BIOLOGICAL ACTIVITY OF CHEMOKINES

FIELD OF THE INVENTION

The present invention relates to new pyrimidinone derivatives and uses thereof to neutralize the biological activity of chemokines, in particular chemokine CXCL12.

More particularly, the invention relates to the use of said compounds as a pharmacological tool or as a medicament, in particular for preventing and/or treating inflammation and inflammatory diseases, immune and auto-immune diseases, pain-related diseases, genetic diseases and/or cancer.

BACKGROUND OF THE INVENTION

Chemokines are small proteins that play critical roles in the development and function of various tissues in vertebrates. As a rather general rule, chemokines and their G protein-coupled receptors display redundancy and binding promiscuity, i.e. several chemokines may bind to the same receptor, whereas a few chemokines play a pivotal and non-redundant homeostatic role. In the adult, they regulate the directional migration of leukocytes under normal and pathological conditions. They are associated with an extraordinary high number of diseases, including chronic inflammatory diseases, autoimmune diseases (lupus erythematosus), cancer, atherosclerosis and AIDS, and their receptors represent druggable targets. Indeed, classical drug design strategies aim at discovering chemokine receptor ligands, mainly antagonists, in order to regulate the associated functions. However, many antagonists have disappointingly failed clinical trials due to chemokine receptors redundancy.

The chemokine CXCL12 plays a pivotal role in normal and pathological situations, including brain development, hematopoiesis, and chronic inflammation[1]. Recently, a group of innovative compounds belonging to the chalcone family that prevent CXCL12 from binding to its CXCR4 or CXCR7 receptors[2-5], have been created with original mechanisms of action: they bind to the chemokine rather than to the receptor, and neutralize its biological activity.

Such molecules were termed "neutraligands" by analogy with neutralizing antibodies, and proved to have therapeutic potential. Indeed a small molecule, "chalcone-4"[5] inhibits binding of CXCL12 to CXCR4 and CXCR7, inhibits intracellular calcium responses, blocks chemotaxis of human peripheral blood CD4+ lymphocytes and prevents CXCR4 internalization in response to CXCL12. This chemical compound is also active in vivo in a mouse model of airway allergic eosinophilic inflammation in which it inhibits inflammatory infiltration in particular of eosinophils. Its activity in other pathologies involving the CXCL12/CXCR4 axis such as the WHIM syndrom or carcinogenesis has also been recently demonstrated[6,7]. Analogues of "chalcone-4" acting as prodrugs to improve its solubility[8] or as an antedrug to optimize the specificity of its topic action[9] have also been developed. Therefore, neutralizing CXCL12 chemokine by small compounds prove to be a promising strategy in inflammatory diseases and for cancer therapy.

These results showing that small organic compounds are able to bind CXCL12 and to neutralize its activity represent a proof of concept that opens new therapeutic routes and the need to develop novel druggable CXCL12 neutraligands.

SUMMARY OF THE INVENTION

One of the objectives of the invention is to find novel compounds able to bind CXCL12 and to neutralize its activity in vivo.

The invention relates to a new class of pyrimidinone derivatives, and uses thereof for inhibiting the biological activity of chemokine CXCL12.

The invention also relates to pharmacological tools or pharmaceutical compositions comprising said new pyrimidinone derivatives for neutralizing CXCL12.

The compounds of the invention are exemplified by formula (I) as described herein.

Another aspect of the invention relates to a method of treating a disease or a condition that involves CXCL12, comprising administration to a patient, in need of said treatment, of a compound according to formula (I) or a pharmaceutical composition comprising a compound according to formula (I).

The disease or condition that can be treated by the compounds of formula (I) as well as the pharmaceutical compositions thereof, includes inflammation and inflammatory diseases, immune and auto-immune diseases, pain-related diseases, genetic diseases and/or cancer.

Non-limiting examples of the diseases that can be treated with the compounds or the compositions of the invention include atopic dermatitis, asthma, atopic rhinitis, atopic conjunctivitis, chronic obstructive pulmonary disease (COPD), pulmonary hypertension (PH), obliterative bronchiolitis and chronic lung allograft dysfunction (CLAD), hyperalgesia/pain, lupus, Sjögren disease, chronic inflammatory diseases such as rhumatoid arthritis, inflammatory bowel disease, WHIM syndrome, rare diseases associated with hypereosinophilia (such as hypereosinophilic syndromes, eosinophilic bronchiolitis, Churg-Strauss syndrome or eosinophilic granulomatosis with polyangeiitis).

DETAILED DESCRIPTION OF THE INVENTION

A subject of the invention is a compound having the general formula (I):

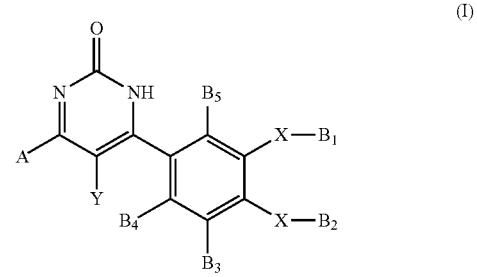

a pharmaceutically acceptable salt thereof or a tautomeric form thereof,
wherein
A represents a cyclic or heterocyclic radical chosen from

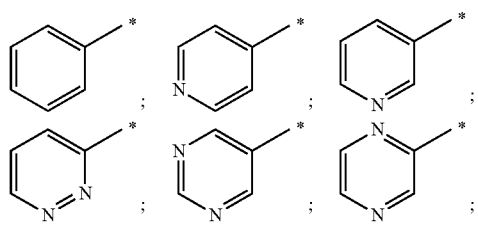

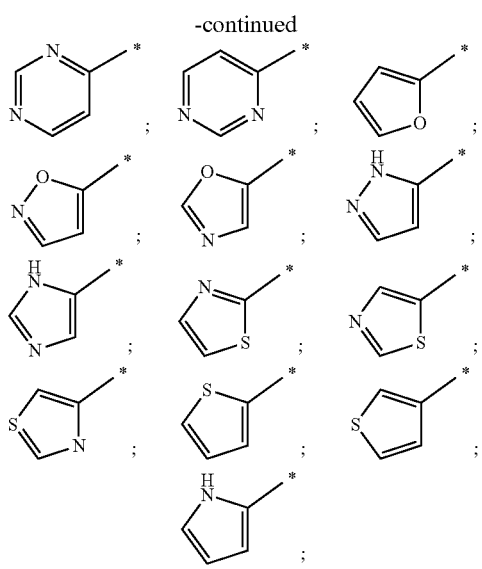

said cyclic or heterocyclic radical may be substituted with substituents chosen from halogen such as F, I, Cl or Br; $(C_1$-$C_{10})$ alkyl; OR with R representing H, $(C_1$-$C_{10})$ alkyl, $CF_3$; CONHR' with R' representing H, $(C_1$-$C_6)$alkyl-$NH_2$, a divalent hydrocarbon radical ($—CH_2—)_n$ linked covalently to a cyclic or heterocyclic compound, saturated or unsaturated, chosen from cyclopropyl $(C_3H_5—)$, cyclobutyl $(C_4H_7—)$, cyclopentyl $(C_5H_9—)$, cyclohexyl $(C_6H_{11}—)$, morpholinyl

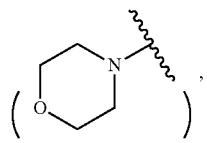

piperazinyl, piperazinyl salt

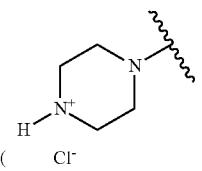

phenyl $(C_6H_5—)$, benzyl $(C_6H_5CH_2—)$, phenetyl $(C_6H_5CH_2CH_2—)$, tolyl $(C_6H_4CH_3—)$, xylyl $(C_6H_3(CH_3)_2—)$, benzylidene $(C_6H_5CH=CH—)$ benzoyl $(C_6H_5CO)$, biphenyl (or diphenyl) $(C_{12}H_9—)$, naphtyl $(C_{10}H_7—)$ or tetrazolyl

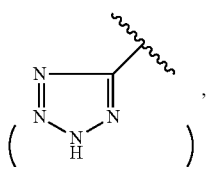

COOR$_a$ with R$_a$ representing H, $(C_1$-$C_{10})$alkyl; NR$_a$R'$_a$ with R$_a$ and R'$_a$ representing independently H, $(C_1$-$C_{10})$alkyl;

CN; a divalent hydrocarbon radical ($—CH_2—)_n$ linked covalently to a cyclic or heterocyclic compound, saturated or unsaturated, chosen from cyclopropyl $(C_3H_5—)$, cyclobutyl $(C_4H_7—)$, cyclopentyl $(C_5H_9—)$, cyclohexyl $(C_6H_{11}—)$, morpholinyl

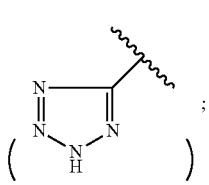

piperazinyl, piperazinyl salt

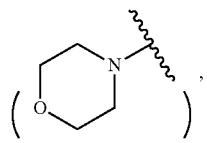

phenyl $(C_6H_5—)$, benzyl $(C_6H_5CH_2—)$, phenetyl $(C_6H_5CH_2CH_2—)$, tolyl $(C_6H_4CH_3—)$, xylyl $(C_6H_3(CH_3)_2—)$, benzylidene $(C_6H_5CH=CH—)$, benzoyl $(C_6H_5CO)$, biphenyl (or diphenyl) $(C_{12}H_9—)$, naphtyl $(C_{10}H_7—)$ or tetrazolyl

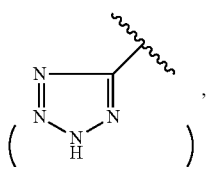

and n being an integer from 0 to 5;

Y represents H; $(C_1$-$C_{10})$alkyl; $(CO)(C_1$-$C_{10})$alkyl; aryl chosen from phenyl, benzyl, phenetyl, tolyl, xylyl, benzylidene or benzoyl;

X represents O, NH or CO;

when X represents O or NH, then $B_1$ and $B_2$ are each independently H; $(C_1$-$C_{10})$alkyl; $CO(C_1$-$C_{10})$alkyl; $CF_3$; $(CH_2)_mNR_aR_b$; $P(O)(OH)_2$; $(CH_2)_pOCO(C_1$-$C_{10})$alkyl; $CO(CH_2)_pNR_aR_b$; $COCH[(CH_2)_nOH][NR_aR_b]$; $COCH[(CH_2)_nNR_aR_b][NR_aR_b]$; $COCH[(CH_2)_nNR_aR_b][NHCOR_a]$; $COCH[(C_1$-$C_{10})$alkyl]$[NR_aR_b]$; $COCH(R_d)NH(R_e)$; a divalent hydrocarbon radical ($—CH_2—)_n$ linked covalently to a cyclic or heterocyclic compound, saturated or unsaturated, chosen from cyclopropyl, cyclobutyl, cyclopentyl, cyclohexyl, morpholinyl, morpholinyl salt, piperazinyl, piperazinyl salt, phenyl, benzyl, phenetyl, tolyl, xylyl, benzylidene, benzoyl, biphenyl, naphtyl or tetrazolyl; sulfonate; carboxylate; one or more aminoacids, such as Lysine or Serine;

with m being an integer from 2 to 5, p being an integer from 1 to 5, n being an integer from 0 to 5, $R_a$ and $R_b$ being each independently H, $(C_1$-$C_{10})$alkyl and $R_d$ and $R_e$ being each independently H, $(C_1$-$C_{10})$alkyl, $(CH_2)_nNR_aR_b$, $COCH_3$, when at least one X represents CO, then $B_1$ and/or $B_2$ which is linked to said CO represents, independently, $(C_1$-$C_{10})$ alkyl; $OR_c$; $C_6H_5$; $(PO)(OH)_2$; a $(CH_2)_n$ group linked covalently to a cyclic or heterocyclic compound, saturated or unsaturated, chosen from cyclopropyl, cyclobutyl, cyclopentyl, cyclohexyl, morpholinyl, morpholinyl salt, piperazinyl, piperazinyl salt, phenyl, benzyl, phenetyl, tolyl, xylyl, benzylidene, benzoyl, biphenyl, naphtyl, tetrazolyl, thiophen, pyrrol, pyrazol, oxazol, thiazol, oxadiazol, thiadiazol, pyrimidine, pyrazine, pyridazine;

with $R_c$ being H, $(C_1-C_{10})$ alkyl, aryl chosen from phenyl, benzyl, phenetyl, tolyl, xylyl, benzylidene or benzoyl, and n being as defined previously, $B_3$, $B_4$, $B_5$ are each independently H; halogen chosen from F, I, Cl or Br; $(C_1-C_{10})$ alkyl; OR; CONHR'; COOR$_a$; CN; a divalent hydrocarbon radical $(—CH_2-)_n$ linked covalently to a cyclic or heterocyclic compound, saturated or unsaturated, chosen from cyclopropyl ($C_3H_5$—), cyclobutyl ($C_4H_7$—), cyclopentyl ($C_5H_9$—), cyclohexyl ($C_6H_{11}$—), morpholinyl

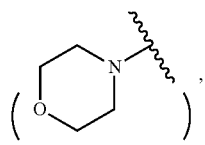, piperazinyl, piperazinyl salt

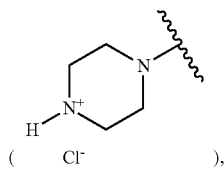 [SMILES: *N1CC[NH2+]CC1 ; [Cl-]]

phenyl ($C_6H_5$—), benzyl ($C_6H_5CH_2$—), phenetyl ($C_6H_5CH_2CH_2$—), tolyl ($C_6H_4CH_3$—), xylyl ($C_6H_3(CH_3)_2$—), benzylidene ($C_6H_5CH=CH$—), benzoyl ($C_6H_5CO$), biphenyl (or diphenyl) ($C_{12}H_9$—), naphtyl ($C_{10}H_7$—) or tetrazolyl

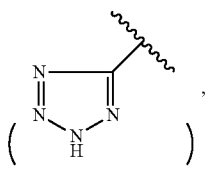, with R representing H, $(C_1-C_{10})$ alkyl, $CF_3$; R' representing H, $(C_1-C_6)$alkyl-$NH_2$, a divalent hydrocarbon radical $(—CH_2-)_n$ linked covalently to a cyclic or heterocyclic compound, saturated or unsaturated, chosen from cyclopropyl ($C_3H_5$—), cyclobutyl ($C_4H_7$—), cyclopentyl ($C_5H_9$—), cyclohexyl ($C_6H_{11}$—), morpholinyl

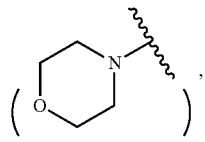, piperazinyl, piperazinyl salt

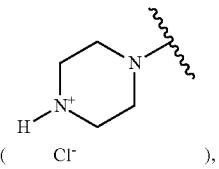

phenyl ($C_6H_5$—), benzyl ($C_6H_5CH_2$—), phenetyl ($C_6H_5CH_2CH_2$—), tolyl ($C_6H_4CH_3$—), xylyl ($C_6H_3(CH_3)_2$—), benzylidene ($C_6H_5CH=CH$—), benzoyl ($C_6H_5CO$), biphenyl (or diphenyl) ($C_{12}H_9$—), naphtyl ($C_{10}H_7$—) or tetrazolyl

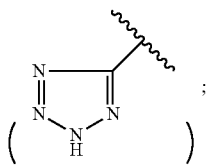;

$R_a$ and n being as defined previously, with the proviso that when X represents O, then $B_1$ and $B_2$ do not represent at the same time a $(C_1-C_{10})$ alkyl.

and with the proviso that compound (I) is not the 4-(1,2-dihydro-6-(4-hydroxy-3-methoxyphenyl)-2-oxopyrimidin-4-yl)-2-methylbenzoic acid.

The term "alkyl" means any monovalent radical of a linear or branched hydrocarbon chain. A $(C_1-C_{10})$ alkyl represents an alkyl having from 1 to 10 carbon atoms. Examples of alkyl groups include methyl, ethyl, n-propyl, i-propyl, n-butyl, i-butyl, s-butyl or t-butyl, n-pentyl, n-hexyl, n-heptyl, n-octyl, 2-ethylhexyl, n-nonyl, 3,5,5-trimethylhexyl, n-decyl, n-undecyl, n-dodecyl or n-octadecyl. Preferred alkyls are methyl, ethyl, isopropyl and t-butyl.

Pharmaceutically acceptable salts comprise, for example, tosylate, mesylate, hydrochloride, hydrobromide, tartrate, hydroiodide, fumarate, oxalate, sulfate, ethanesulfonate, citrate, trifluoroacetate, ascorbate, triflate, formate, acetate, maleate, propionate, furoate.

Tautomeric forms of compound (I) comprise the following compounds:

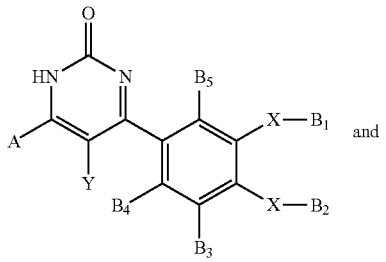

and

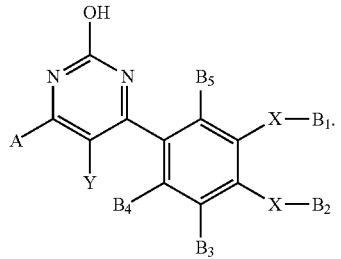

According to an embodiment of the invention, in formula (I) above, it is also possible for A to represent a cyclic or heterocyclic radical having 3 to 10 atoms, which may be saturated or not, which may be substituted or not, and which are for examples the following:

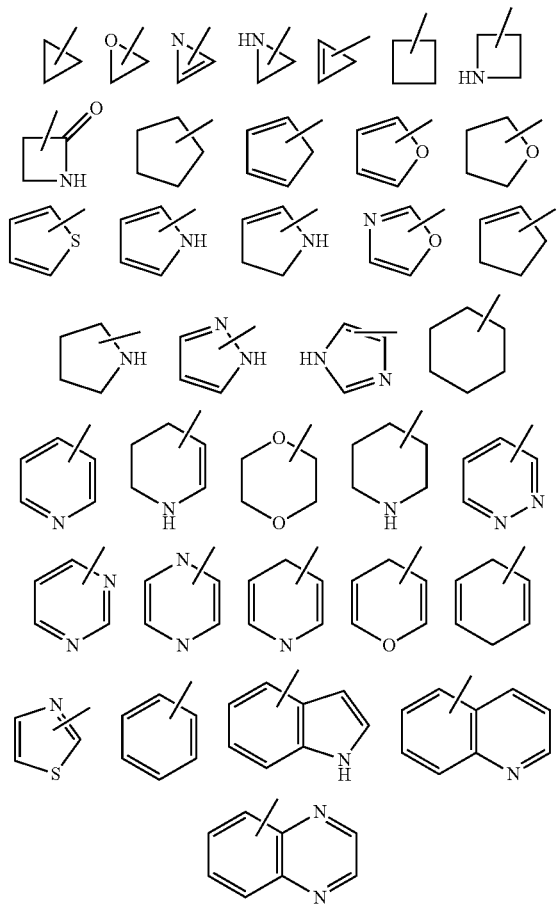

Said cycles may be substituted. The substitution may substitute an H of a carbon atom or may substitute the H in NH groups. Examples of substituents are halogen chosen from F, I, Cl or Br; $(C_1-C_{10})$ alkyl; OR with R as defined previously; CONHR' with R' as defined previously; COOR$_a$ with R$_a$ as defined previously; NR$_a$R'$_a$ with R$_a$ and R'$_a$ as defined previously; CN; a divalent hydrocarbon radical (—CH$_2$-)$_n$ linked covalently to a cyclic or heterocyclic compound, saturated or unsaturated, chosen from cyclopropyl (C$_3$H$_5$—), cyclobutyl (C$_4$H$_7$—), cyclopentyl (C$_5$H$_9$—), cyclohexyl (C$_6$H$_{11}$—), morpholinyl

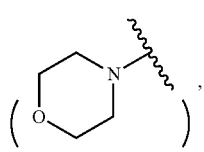

piperazinyl, piperazinyl salt

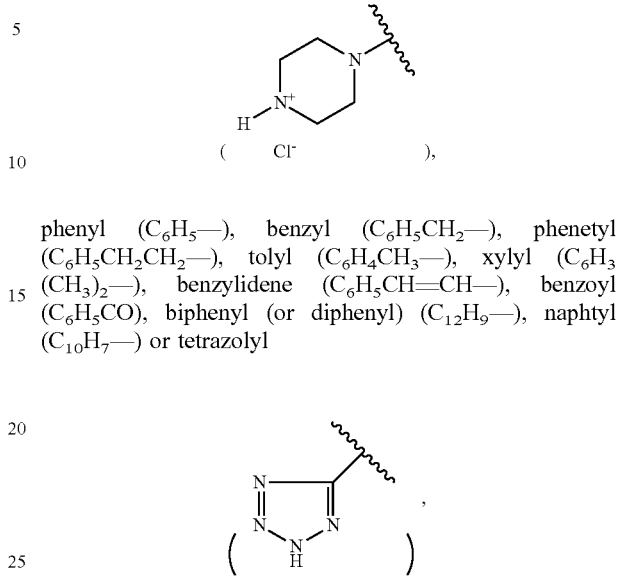

phenyl (C$_6$H$_5$—), benzyl (C$_6$H$_5$CH$_2$—), phenetyl (C$_6$H$_5$CH$_2$CH$_2$—), tolyl (C$_6$H$_4$CH$_3$—), xylyl (C$_6$H$_3$(CH$_3$)$_2$—), benzylidene (C$_6$H$_5$CH=CH—), benzoyl (C$_6$H$_5$CO), biphenyl (or diphenyl) (C$_{12}$H$_9$—), naphtyl (C$_{10}$H$_7$—) or tetrazolyl

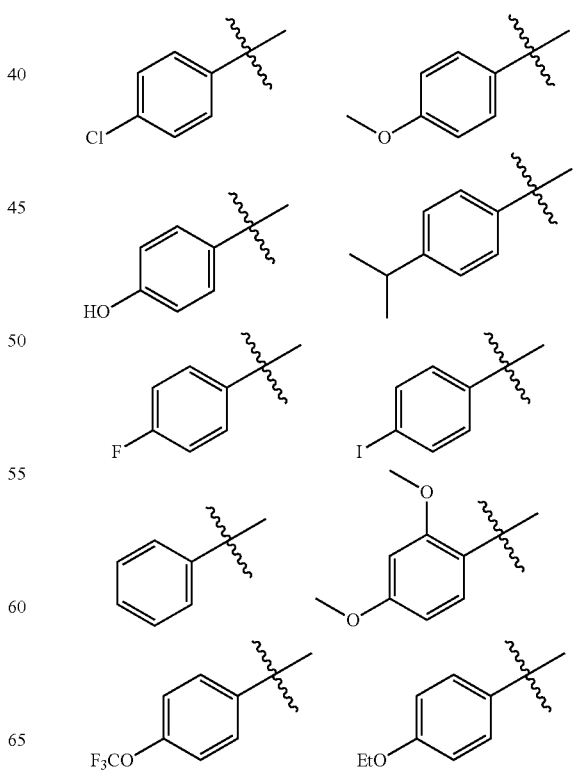

and n being as defined previously.

According to a specific embodiment, A is selected from phenyl, furanyl, pyridinyl, thiophenyl, pyrrolyl, oxazolyl, thiazolyl, pyrimidinyl, pyrazinyl or pyridazinyl, which may be substituted.

According to another embodiment, in compound of formula (I), A is selected from:

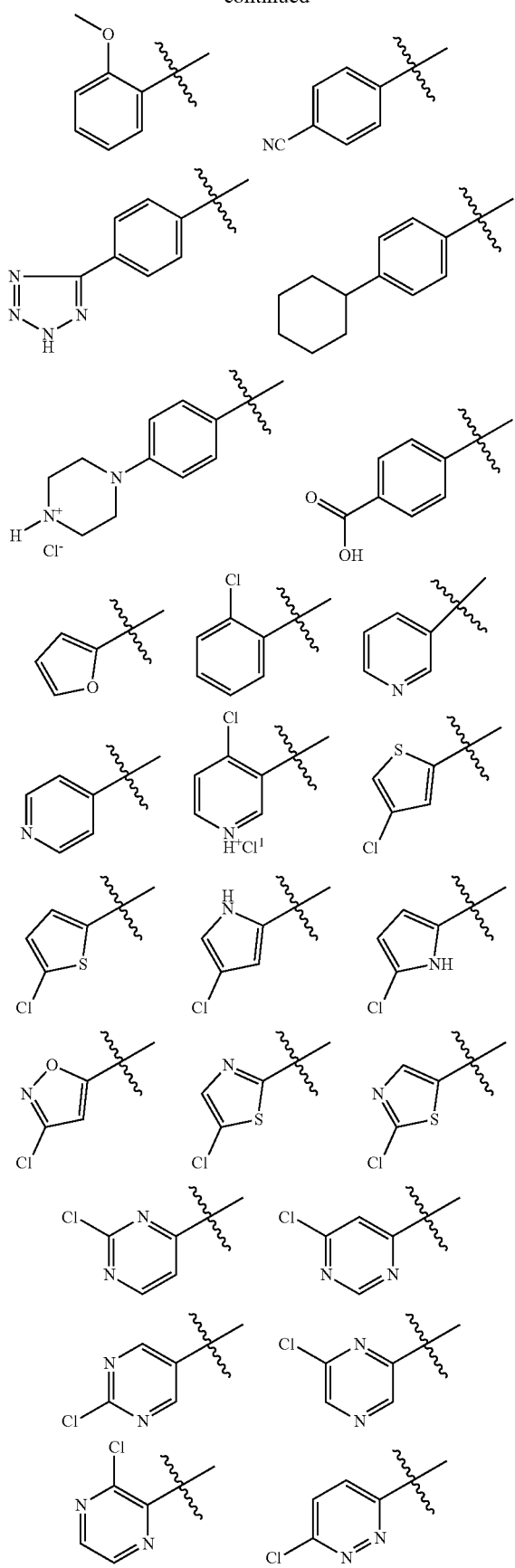
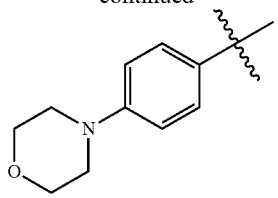
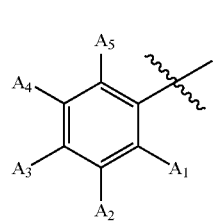
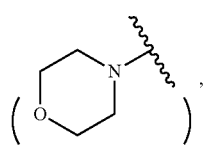
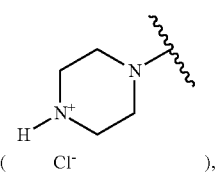

According to still another embodiment, A is not pyrrolyl, pyridinyl, dihydropyrodinyl and indolyl.

According to another embodiment of the invention, when X represents O or NH in the above mentioned compound (I), and when $B_1$ and $B_2$ are each independently $(CH_2)_m NR_a R_b$ $CO(CH_2)_p NR_a R_b$; $COCH[(CH_2)_n OH][NR_a R_b]$; $COCH$ $[(CH_2)_n NR_a R_b][NR_a R_b]$; $COCH[(CH_2)_n NR_a R_b]$ $[NHCOR_a]$; $COCH[(C_1-C_{10})\text{alkyl}][NR_a R_b]$, then the $NR_a R_b$ group represents $NH_2$ or $NH_3^+$ $Cl^-$, and m, p, n are as defined previously.

According to another embodiment of the invention, in compound (I) as defined above, A is a substituted phenyl group having the following formula:

(A)

wherein $A_1$, $A_2$, $A_3$, $A_4$, $A_5$ are each independently H; halogen chosen from F, I, Cl or Br;

$(C_1-C_{10})$ alkyl; OR with R representing H, $(C_1-C_{10})$ alkyl, $CF_3$; CONHR' with R'=H, $(C_1-C_6)$ alkyl-$NH_2$, a divalent hydrocarbon radical $(-CH_2-)_n$ linked covalently to a cyclic or heterocyclic compound, saturated or unsaturated, chosen from cyclopropyl ($C_3H_5$—), cyclobutyl ($C_4H_7$—), cyclopentyl ($C_5H_9$—), cyclohexyl ($C_6H_{11}$—), morpholinyl

, piperazinyl, piperazinyl salt ( $Cl^-$ ), phenyl ($C_6H_5$—), benzyl ($C_6H_5CH_2$—), phenetyl ($C_6H_5CH_2CH_2$—), tolyl ($C_6H_4CH_3$—), xylyl ($C_6H_3$ ($CH_3)_2$—), benzylidene ($C_6H_5CH=CH$—), benzoyl ($C_6H_5CO$), biphenyl (or diphenyl) ($C_{12}H_9$—), naphtyl ($C_{10}H_7$—) or tetrazolyl

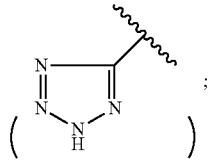

$COOR_a$ with $R_a$ representing H, ($C_1$-$C_{10}$)alkyl; $NR_aR'_a$ with $R_a$ and $R'_a$ representing independently H, ($C_1$-$C_{10}$)alkyl; CN; a divalent hydrocarbon radical (—$CH_2$-$)_n$ linked covalently to a cyclic or heterocyclic compound, saturated or unsaturated, chosen from cyclopropyl ($C_3H_5$—), cyclobutyl ($C_4H_7$—), cyclopentyl ($C_5H_9$—), cyclohexyl ($C_6H_{11}$—), morpholinyl

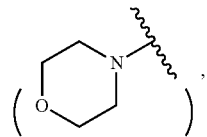

piperazinyl, piperazinyl salt

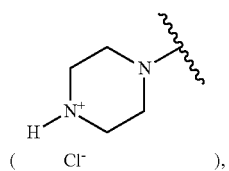 [SMILES: *N1CC[NH2+]CC1 ; [Cl-]]

phenyl ($C_6H_5$—), benzyl ($C_6H_5CH_2$—), phenetyl ($C_6H_5CH_2CH_2$—), tolyl ($C_6H_4CH_3$—), xylyl ($C_6H_3(CH_3)_2$—), benzylidene ($C_6H_5CH=CH$—), benzoyl ($C_6H_5CO$), biphenyl (or diphenyl) ($C_{12}H_9$—), naphtyl ($C_{10}H_7$—) or tetrazolyl

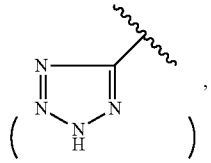

and n being an integer from 0 to 5.

According to another embodiment of the invention, in compound of formula (I) as defined above, $A_1$, $A_2$, $A_4$, $B_4$, $B_5$ and Y represent H, and $A_3$, $A_5$, $B_3$, X, $B_1$ and $B_2$ are as defined above.

According to a particular embodiment of the invention, in compound of formula (I) above:

A represents:

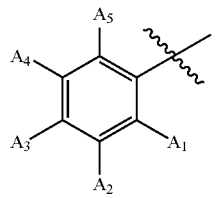

wherein $A_1$, $A_2$, $A_4$ represent H, $B_4$, $B_5$ and Y represent H, and, $A_3$, $A_5$ and $B_3$ are each independently H; a halogen chosen from F, I or Cl; an alkyl radical chosen from methyl, ethyl or isopropyl; an OR group chosen from OH, $OCH_3$, $OC_2H_5$ or $OCF_3$; COOH; CN; a cyclic or heterocyclic compound chosen from cyclohexyl, morpholinyl, piperazinyl, piperazinyl salt or tetrazolyl;

when X represents O or NH, then $B_1$ and $B_2$ are each independently H; methyl, ethyl; $COCH_3$; $COCH(CH_3)_2$; $CF_3$; $CH_2$—$CH_2$—$NH_2$, $CH_2$—$CH_2$—$NH_3^+Cl^-$; $P(O)(OH)_2$, $P(O)(ONa)_2$; $CH_2OCOCH_3$; $COCH[(CH_2)OH][NH_3^+$ $Cl^-]$; $COCH[(CH_2)_4NH_3^+$ $Cl^-][NH_3^+$ $Cl^-]$; $SO_3^-Na^+$; $COCH[(CH_2)_4NH_3^+$ $Cl^-][NHCOCH_3]$; $COCH[(CH(CH_3)_2][NH_3^+$ $Cl^-]$; a hydrocarbon radical (—$CH_2$-$)_n$ linked covalently to a cyclic or heterocyclic compound, saturated or unsaturated, chosen from

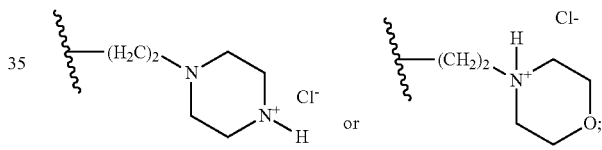

n being as defined previously, when at least one X represents CO, then $B_1$ and/or $B_2$ which is linked to said CO represents, independently, methyl, ethyl; OH, $OCH_3$, $OC_6H_5$; $C_6H_5$; $(PO)(OH)_2$; a hydrocarbon radical (—$CH_2$-$)_n$ linked covalently to a cyclic or heterocyclic compound, saturated or unsaturated, chosen from

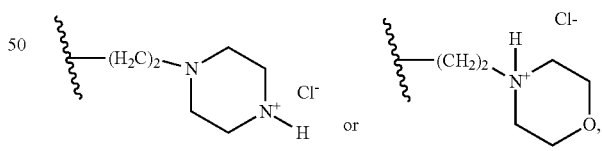

n being as defined previously.

According to an advantageous embodiment of the invention, in compounds of formula (I) as defined previously, the X linked to the $B_2$ group represents O and $B_2$ represents H.

According to another advantageous embodiment of the invention, in compound of formula (I) as defined previously, X represents O, $B_1$ represents a ($C_1$-$C_{10}$) alkyl and $B_2$ represents H.

Examples of such compounds are those selected from the group wherein:

$A_1$=$A_2$=$A_4$=$B_4$=$B_5$=Y=H, and

X=O, $A_5$=$B_3$=H, $A_3$=Cl, $B_1$=$CH_3$, $B_2$=H (1),

X=O, $A_5$=$B_3$=H, $A_3$=OCH$_3$, $B_1$=CH$_3$, $B_2$=H (2),
X=O, $A_5$=$B_3$=H, $A_3$=OH, $B_1$=CH$_3$, $B_2$=H (3),
X=O, $A_5$=$B_3$=H, $A_3$=CH(CH$_3$)$_2$, $B_1$=CH$_3$, $B_2$=H (4),
X=O, $A_5$=$B_3$=H, $A_3$=F, $B_1$=CH$_3$, $B_2$=H (5),
X=O, $A_5$=$B_3$=H, $A_3$=I, $B_1$=CH$_3$, $B_2$=H (6),
X=O, $A_5$=Cl, $A_3$=$B_3$=H, $B_1$=CH$_3$, $B_2$=H (7),
X=O, $A_5$=$A_3$=$B_3$=H, $B_1$=CH$_3$, $B_2$=H (8),
X=O, $A_5$=$A_3$=OCH$_3$, $B_3$=H, $B_1$=CH$_3$, $B_2$=H (11),
X=O, $A_3$=OCF$_3$, $A_5$=$B_3$=H, $B_1$=CH$_3$, $B_2$=H (12),
X=O, $A_3$=OCH$_2$CH$_3$, $A_5$=$B_3$=H, $B_1$=CH$_3$, $B_2$=H (13),
X=O, $A_5$=OCH$_3$, $A_3$=$B_3$=H, $B_1$=CH$_3$, $B_2$=H (14),
X=O, $A_3$=CN, $A_5$=$B_3$=H, $B_1$=CH$_3$, $B_2$=H (15),
X=O, $A_3$=cyclohexyl, $A_5$=$B_3$=H, $B_1$=CH$_3$, $B_2$=H (16),
X=O, $A_3$=Cl, $A_5$=H, $B_3$=OCH$_3$, $B_1$=CH$_3$, $B_2$=H (17),
X=O, $A_3$=tetrazolyl, $A_5$=$B_3$=H, $B_1$=CH$_3$, $B_2$=H (18),
X=O, $A_3$=morpholinyl, $A_5$=$B_3$=H, $B_1$=CH$_3$, $B_2$=H (19),
X=O, $A_3$=piperazinyl salt

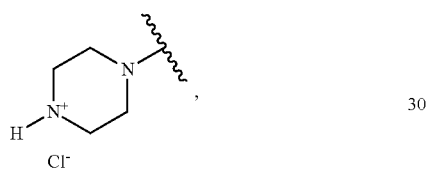

$A_5$=$B_3$=H, $B_1$=CH$_3$, $B_2$=H (21),
X=O, $A_3$=COOH, $A_5$=$B_3$=H, B=CH$_3$, $B_2$=H (22),
X=O, $A_3$=methyl-piperaziny

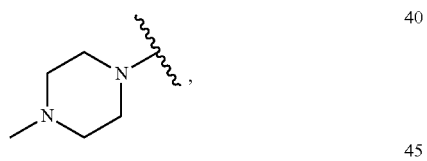

$A_5$=$B_3$=H, $B_1$=CH$_3$, $B_2$=H (24),
and their mixtures.

Another example of such a compound is a compound of formula (I) wherein $A_1$=$A_2$=$A_5$=$B_3$=$B_4$=$B_5$=Y=H, and
X=O, $A_4$=CH$_3$, $A_3$=OH, $B_1$=CH$_3$, $B_2$=H (59).

Still other examples of compounds of formula (I) wherein X represents O, $B_1$ represents a (C$_1$-C$_{10}$) alkyl and $B_2$ represents H are those selected from the group wherein:

X=O, $B_3$=$B_4$=$B_5$=Y=H, $B_1$=CH$_3$, $B_2$=H, and A represents

(28)

A represents

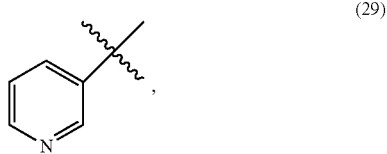 [SMILES: *c1cccnc1]

(29)

A represents

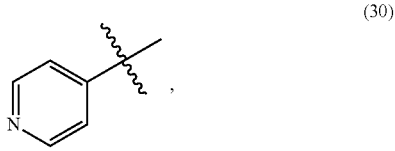 [SMILES: *c1ccncc1]

(30)

A represents

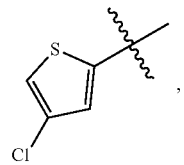

(31)

A represents

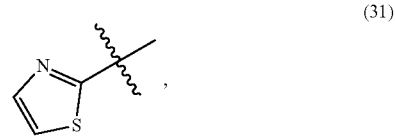 [SMILES: *c1nccs1]

(32)

A represents

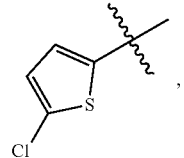

(33)

A represents

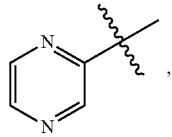

(34)

A represents
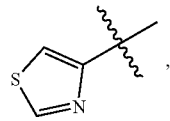 (35)
A represents
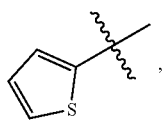 (36)
A represents
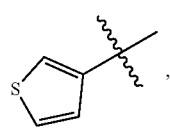 (37)
A represents
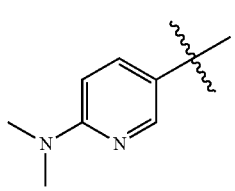 (38)
A represents
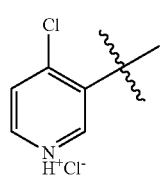 (39)
A represents
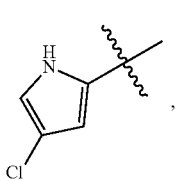 (40)
A represents
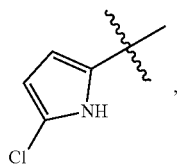 (41)
A represents
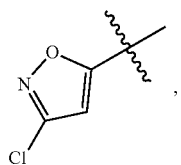 (42)
A represents
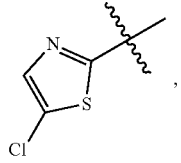 (43)
A represents
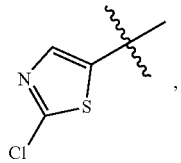 (44)
A represents
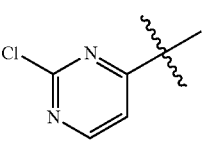 (45)
A represents
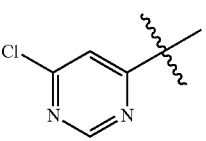 (46)

A represents

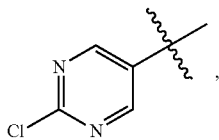 (47)

A represents

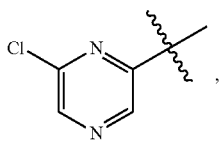 (48)

A represents

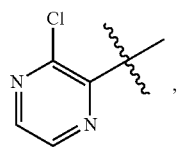 (49)

A represents

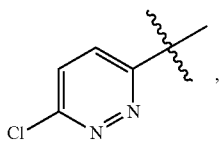 (50)

A represents

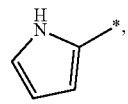 (60)

and their mixtures.

According to another embodiment of the invention, compounds of general formula (I) are those selected from the group wherein:

$A_1=A_2=A_4=B_4=B_5=Y=H$, and $X=O$, $A_5=B_3=H$, $A_3=Cl$, $B_1=CF_3$, $B_2=H$ (9), $X=O$, $A_5=B_3=H$, $A_3=Cl$, $B_1=H$, $B_2=CH_3$ (10), $X=O$, $A_3=Cl$, $A_5=B_3=H$, $B_1=CH_3$, $B_2=PO(ONa)_2$ (20), $X=O$, $A_3=Cl$, $A_5=B_3=H$, $B_1=CH_2CH_2NH_3^+$ $Cl^-$, $B_2=H$ (23), $X=O$, $A_3=Cl$, $A_5=B_3=H$, $B_1=$

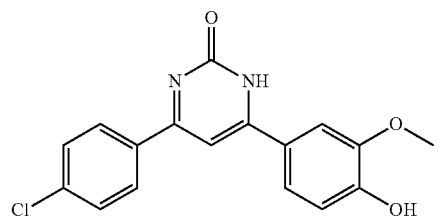 [SMILES: COc1cc(-c2cc(-c3ccc(Cl)cc3)nc(=O)[nH]2)ccc1O]

$B_2=H$ (25),

X linked to $B_1$ represents O and X linked to $B_2$ represents NH, $A_3=Cl$, $A_5=B_3=H$, $B_1=CH_3$, $B_2=COCH_3$ (26), X linked to $B_1$ represents O and X linked to $B_2$ represents CO, $A_3=Cl$, $A_5=B_3=H$, $B_1=CH_3$, $B_2=OH$ (27), and their mixtures.

Compounds (1) to (60) of formula (I) are represented in Table 1 below.

TABLE 1

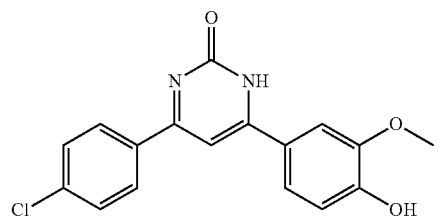 [SMILES: COc1cc(-c2cc(-c3ccc(Cl)cc3)nc(=O)[nH]2)ccc1O] (1)

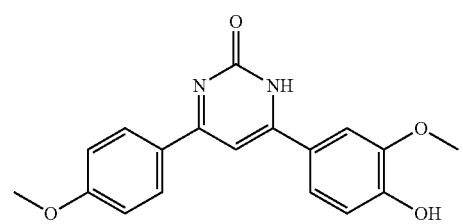 (2)

TABLE 1-continued
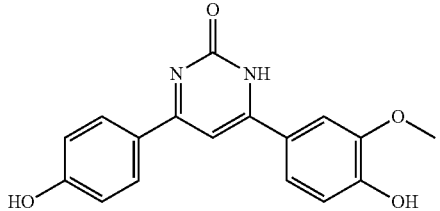 [SMILES: COc1cc(-c2cc(-c3ccc(O)cc3)nc(=O)[nH]2)ccc1O] (3)
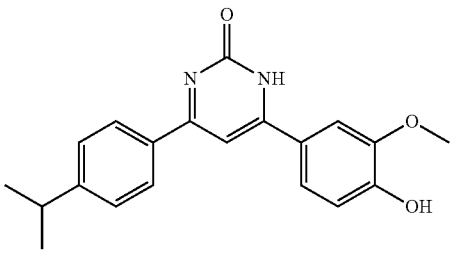 [SMILES: COc1cc(-c2cc(-c3ccc(C(C)C)cc3)nc(=O)[nH]2)ccc1O] (4)
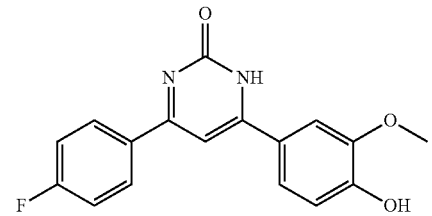 [SMILES: COc1cc(-c2cc(-c3ccc(I)cc3)nc(=O)[nH]2)ccc1O] (5)
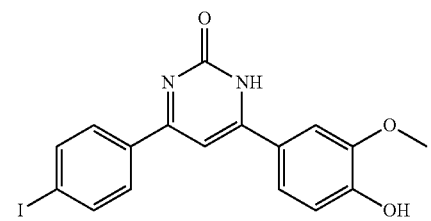 (6)
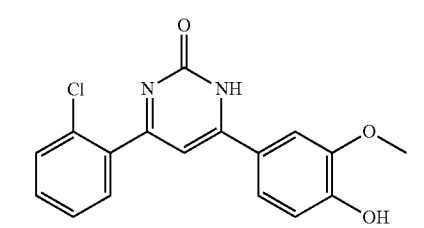 [SMILES: COc1cc(-c2cc(-c3ccccc3Cl)nc(=O)[nH]2)ccc1O] (7)
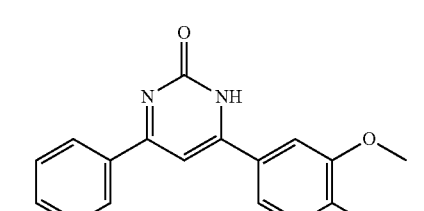 (8)
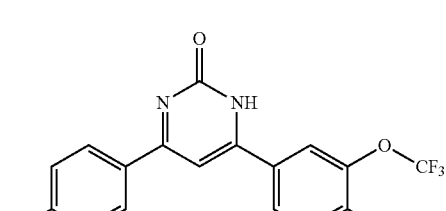 (9)

TABLE 1-continued
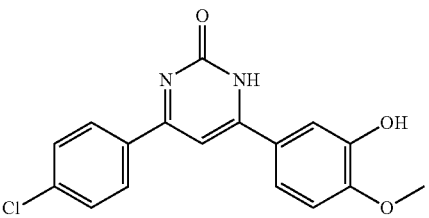 [SMILES: COc1ccc(-c2cc(-c3ccc(Cl)cc3)nc(=O)[nH]2)cc1O]
(10)
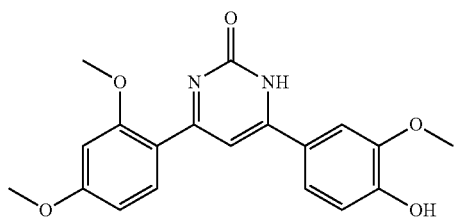
(11)
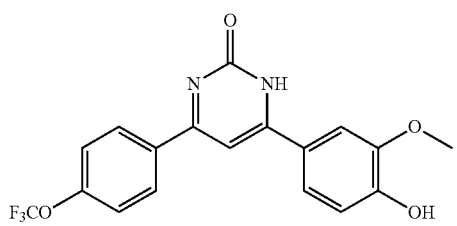 [SMILES: COc1cc(-c2cc(-c3ccc(OC(F)(F)F)cc3)nc(=O)[nH]2)ccc1O]
(12)
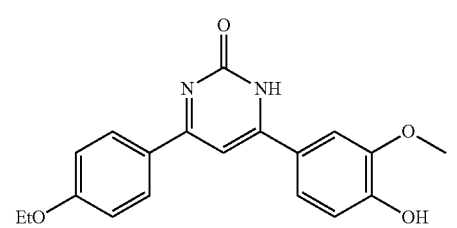 [SMILES: CCOc1ccc(-c2cc(-c3ccc(O)c(OC)c3)[nH]c(=O)n2)cc1]
(13)
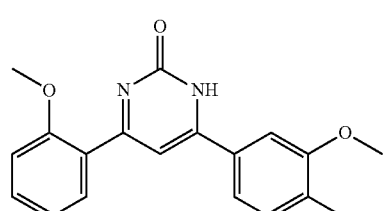
(14)
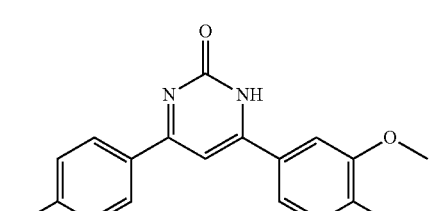
(15)
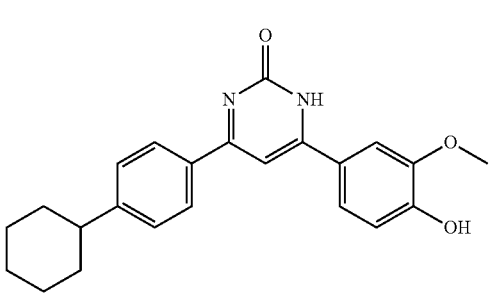 [SMILES: COc1cc(-c2cc(-c3ccc(C4CCCCC4)cc3)nc(=O)[nH]2)ccc1O]
(16)

TABLE 1-continued
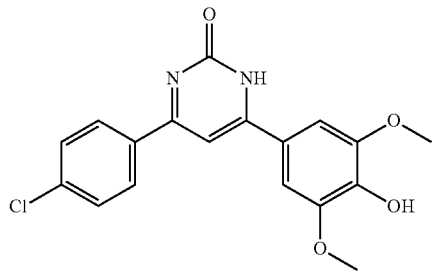 [SMILES: COc1cc(-c2cc(-c3ccc(Cl)cc3)nc(=O)[nH]2)cc(OC)c1O]
(17)
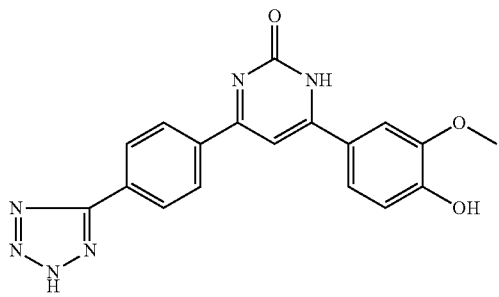 [SMILES: COc1cc(-c2cc(-c3ccc(-c4nn[nH]n4)cc3)nc(=O)[nH]2)ccc1O]
(18)
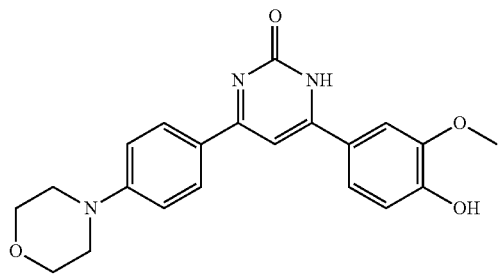 [SMILES: COc1cc(-c2cc(-c3ccc(N4CCOCC4)cc3)nc(=O)[nH]2)ccc1O]
(19)
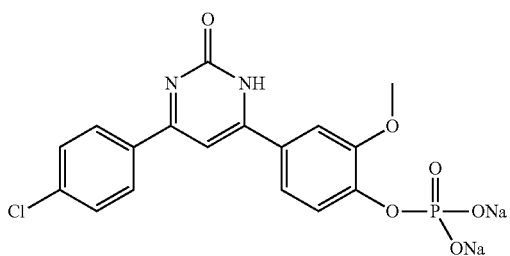
(20)
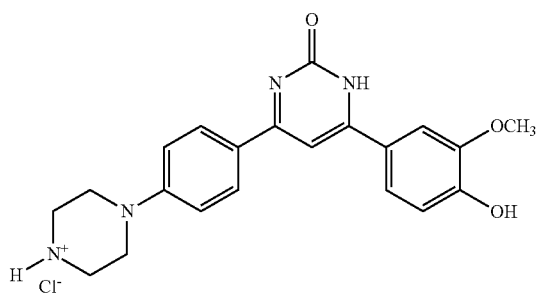 [SMILES: COc1cc(-c2cc(-c3ccc(N4CC[NH2+]CC4)cc3)nc(=O)[nH]2)ccc1O ; [Cl-]]
(21)

TABLE 1-continued
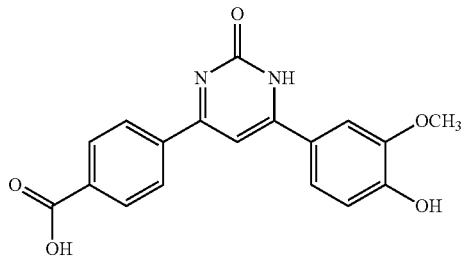 [SMILES: COc1cc(-c2cc(-c3ccc(C(=O)O)cc3)nc(=O)[nH]2)ccc1O]
(22)
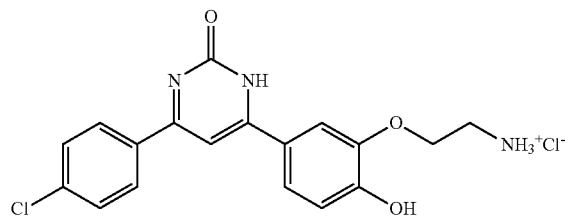
(23)
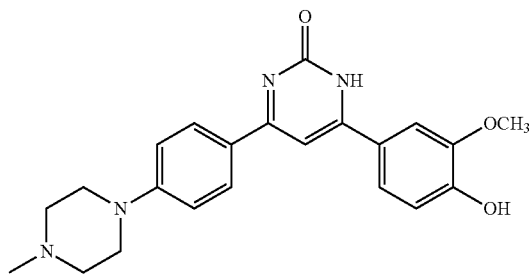 [SMILES: COc1cc(-c2cc(-c3ccc(N4CCN(C)CC4)cc3)nc(=O)[nH]2)ccc1O]
(24)
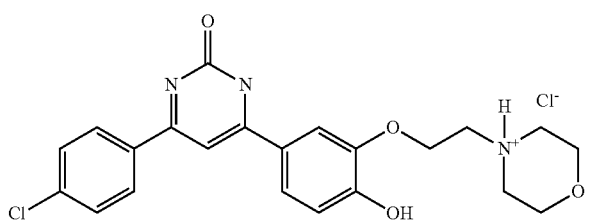 [SMILES: O=c1nc(-c2ccc(Cl)cc2)cc(-c2ccc(O)c(OCC[NH+]3CCOCC3)c2)[nH]1 ; [Cl-]]
(25)
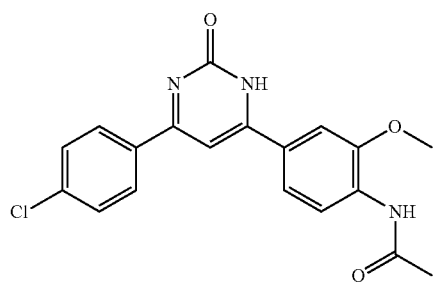 [SMILES: COc1cc(-c2cc(-c3ccc(Cl)cc3)nc(=O)[nH]2)ccc1NC(C)=O]
(26)
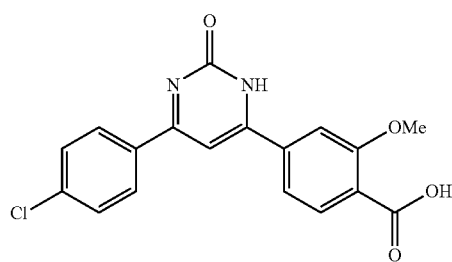 [SMILES: COc1cc(-c2cc(-c3ccc(Cl)cc3)nc(=O)[nH]2)ccc1C(=O)O]
(27)

TABLE 1-continued
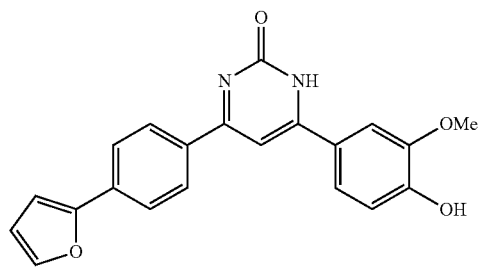 [SMILES: COc1cc(-c2cc(-c3ccc(-c4ccco4)cc3)nc(=O)[nH]2)ccc1O]
(28)
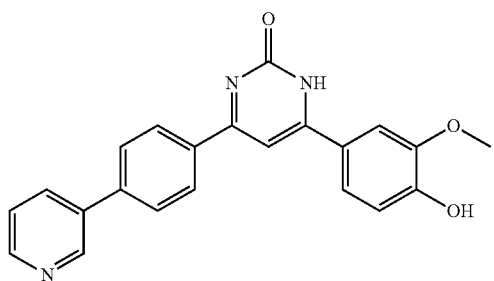 [SMILES: COc1cc(-c2cc(-c3ccc(-c4cccnc4)cc3)nc(=O)[nH]2)ccc1O]
(29)
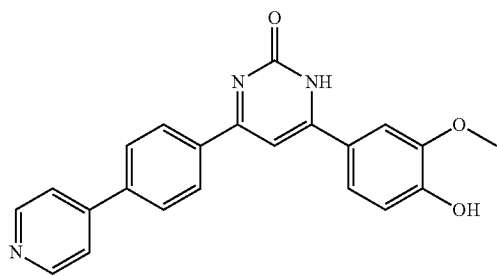 [SMILES: COc1cc(-c2cc(-c3ccc(-c4ccncc4)cc3)nc(=O)[nH]2)ccc1O]
(30)
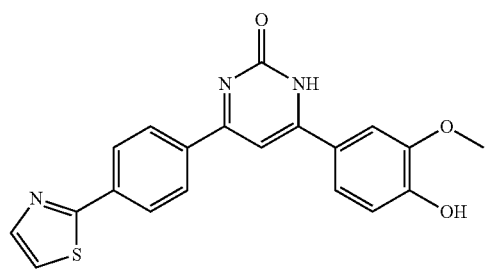 [SMILES: COc1cc(-c2cc(-c3ccc(-c4nccs4)cc3)nc(=O)[nH]2)ccc1O]
(31)
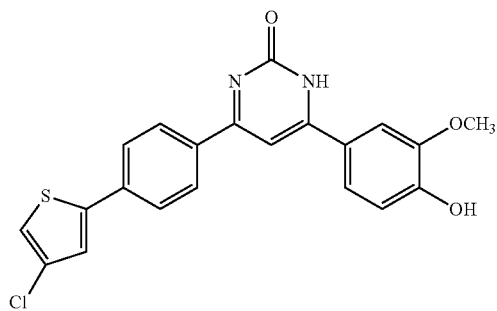 [SMILES: COc1cc(-c2cc(-c3ccc(-c4cc(Cl)cs4)cc3)nc(=O)[nH]2)ccc1O]
(32)

TABLE 1-continued
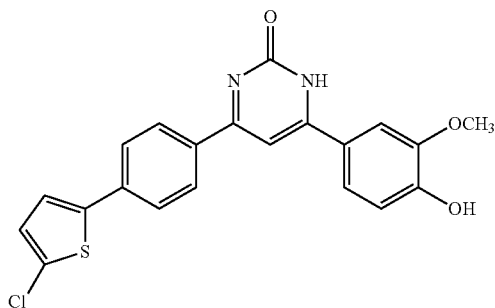 [SMILES: COc1cc(-c2cc(-c3ccc(-c4ccc(Cl)s4)cc3)nc(=O)[nH]2)ccc1O]
(33)
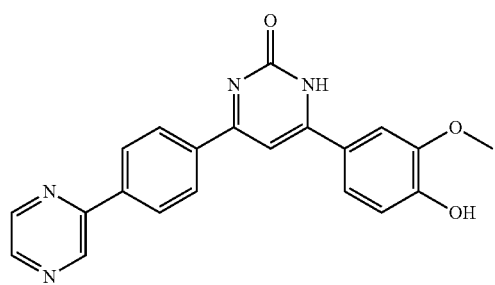 [SMILES: COc1cc(-c2cc(-c3ccc(-c4cnccn4)cc3)nc(=O)[nH]2)ccc1O]
(34)
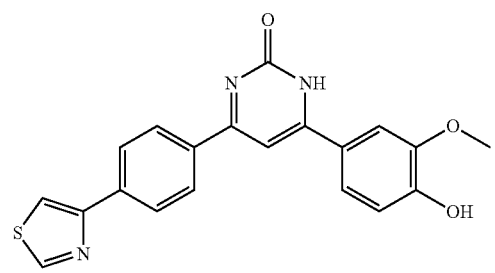 [SMILES: COc1cc(-c2cc(-c3ccc(-c4cscn4)cc3)nc(=O)[nH]2)ccc1O]
(35)
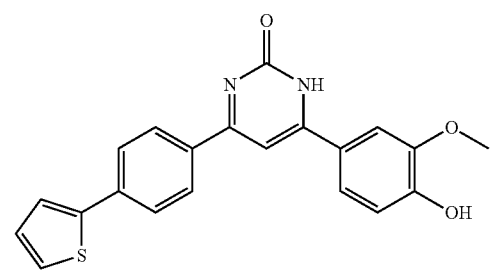
(36)
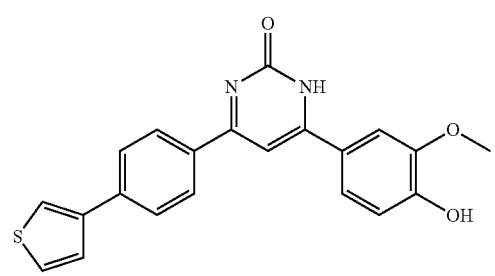 [SMILES: COc1cc(-c2cc(-c3ccc(-c4ccsc4)cc3)nc(=O)[nH]2)ccc1O]
(37)

TABLE 1-continued
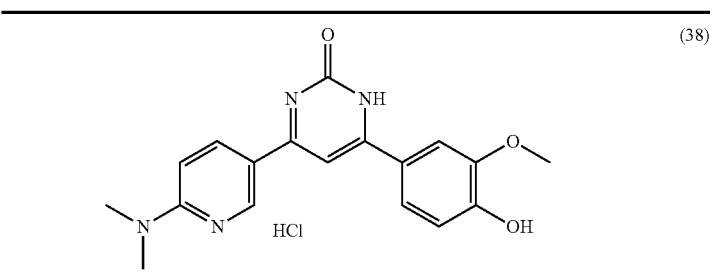
(38)
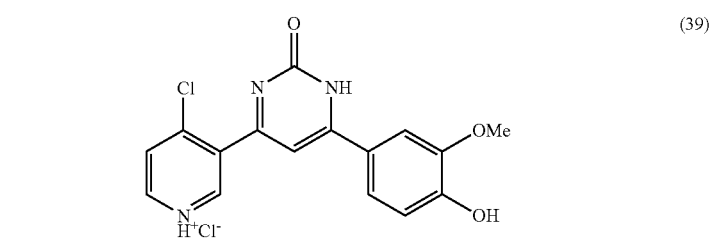
(39)
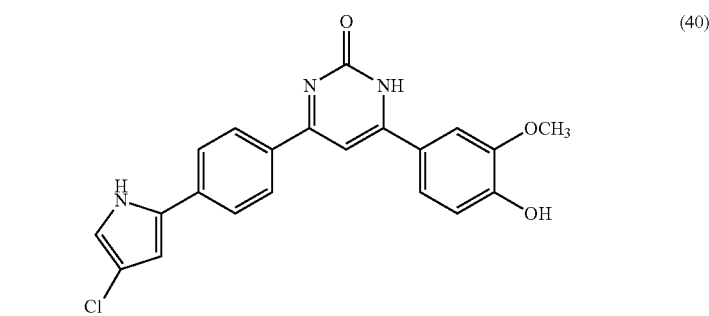
(40)
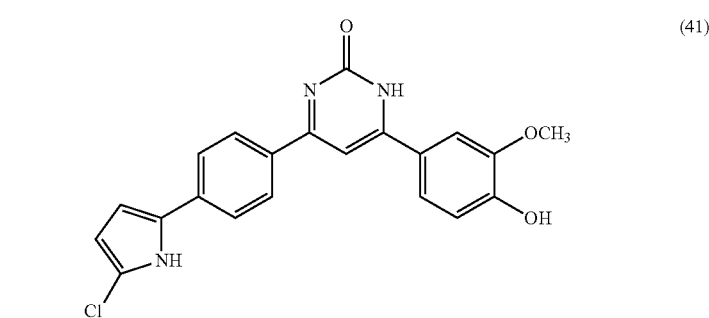
(41)
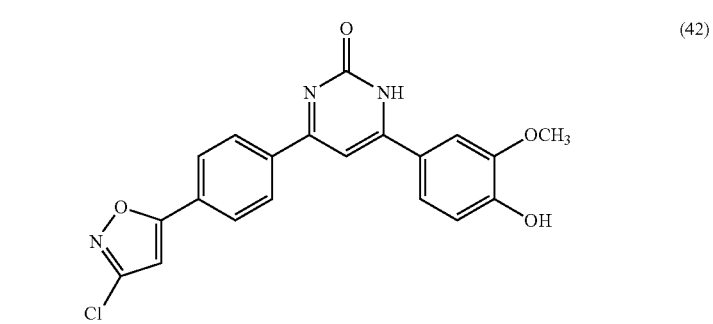
(42)

TABLE 1-continued
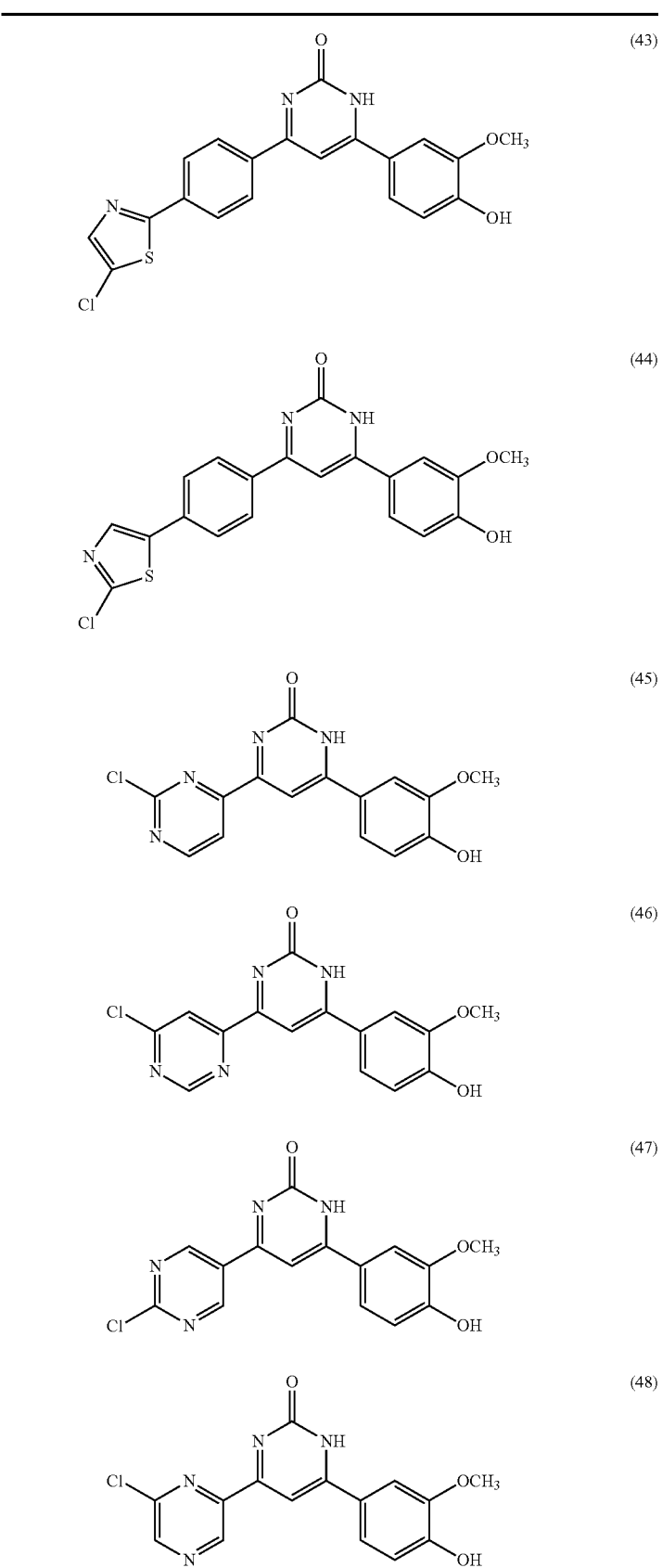

TABLE 1-continued
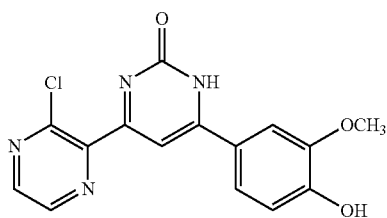 [SMILES: COc1cc(-c2cc(-c3nccnc3Cl)nc(=O)[nH]2)ccc1O]
(49)
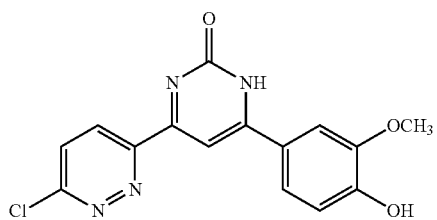 [SMILES: COc1cc(-c2cc(-c3ccc(Cl)nn3)nc(=O)[nH]2)ccc1O]
(50)
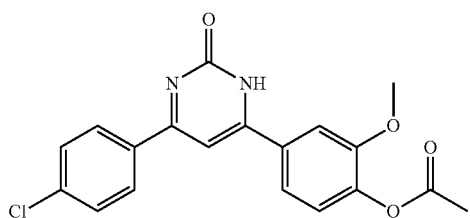 [SMILES: COc1cc(-c2cc(-c3ccc(Cl)cc3)nc(=O)[nH]2)ccc1OC(C)=O]
(51)
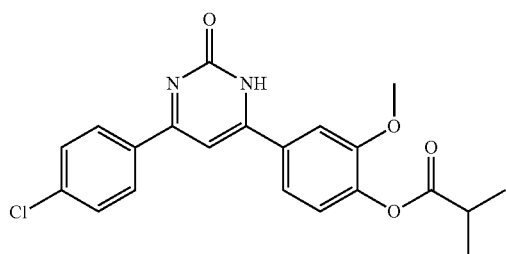 [SMILES: COc1cc(-c2cc(-c3ccc(Cl)cc3)nc(=O)[nH]2)ccc1OC(=O)C(C)C]
(52)
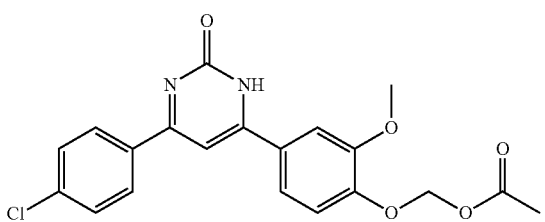 [SMILES: COc1cc(-c2cc(-c3ccc(Cl)cc3)nc(=O)[nH]2)ccc1OCOC(C)=O]
(53)
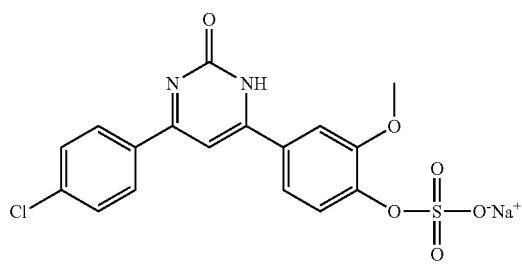
(54)

TABLE 1-continued
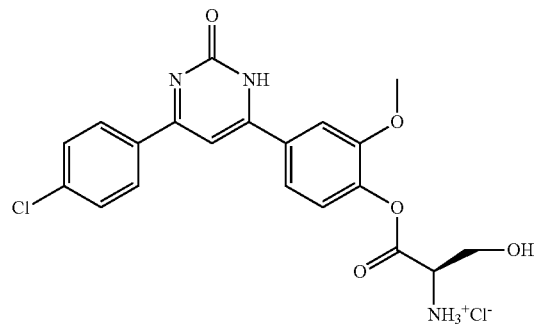 (55)
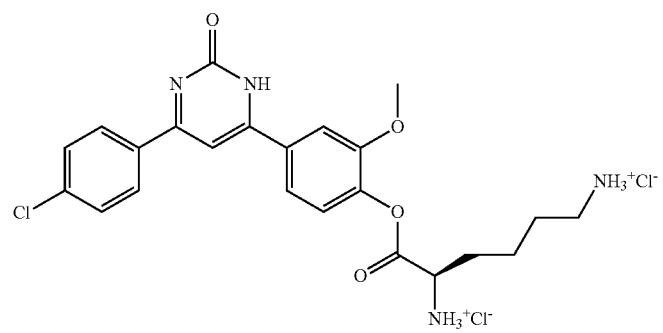 (56)
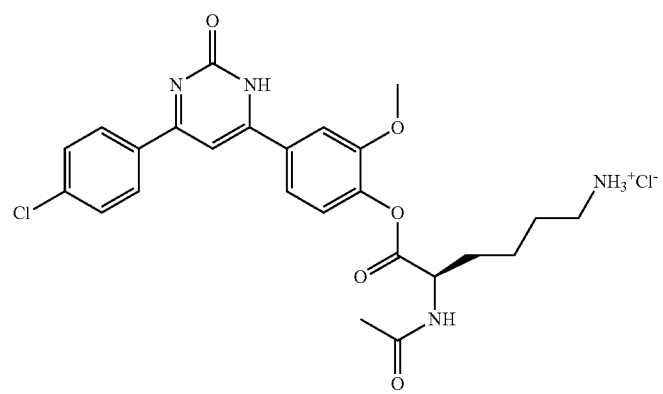 (57)
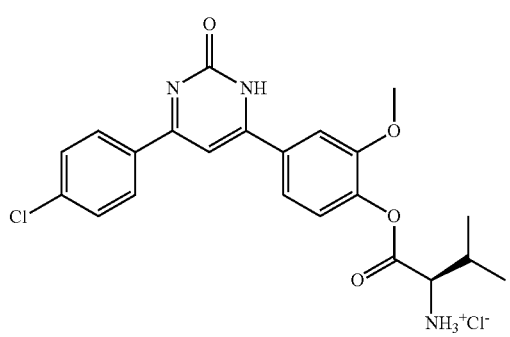 (58)
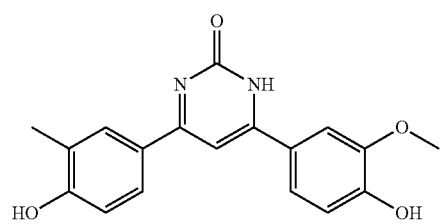 [SMILES: COc1cc(-c2cc(-c3ccc(O)c(C)c3)nc(=O)[nH]2)ccc1O] (59)

TABLE 1-continued

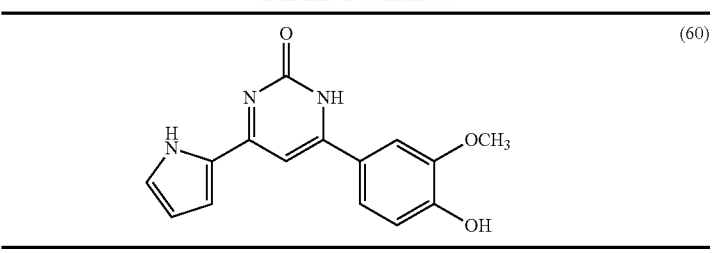

(60)

According to a particular embodiment of the invention, compounds of formula (I) are selected in the group consisting of compounds (1), (2), (3), (5), (7), (8), (9) and their mixtures.

According to another particular embodiment of the invention, compounds of formula (I) are selected in the group consisting of compounds (1), (2) and (7).

The tautomeric forms of compound (1) are the following:

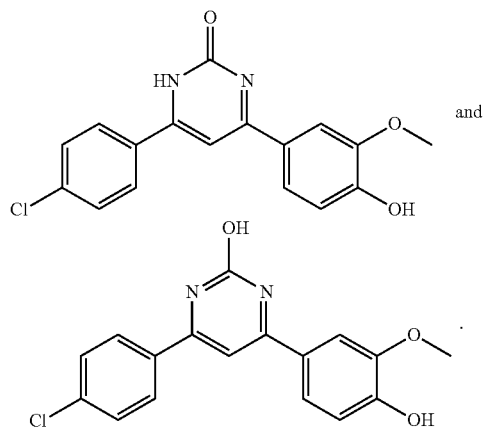

Compound (1) is particularly preferred since it presents improved physicochemical properties, in particular in view of "chalcone-4" described in the state of the art[5,6,7,8,9]. In particular, its solubility is better than the solubility of "chalcone-4".

A subject of the invention is also a compound of general formula (I) as defined above, a pharmaceutically acceptable salt thereof or a tautomeric form thereof, for use as a medicament.

According to an advantageous embodiment, the invention relates to compound of general formula (I) as defined above, a pharmaceutically acceptable salt thereof or a tautomeric form thereof, for use for inhibiting the biological activity of chemokine CXCL12.

According to another advantageous embodiment, the invention relates to compound of general formula (I) as defined above, a pharmaceutically acceptable salt thereof or a tautomeric form thereof, for the prevention and/or treatment of inflammation and inflammatory diseases, immune and auto-immune diseases, pain-related diseases, genetic diseases and/or cancer.

Another subject of the invention is a composition comprising at least a compound of formula (I), a pharmaceutically acceptable salt thereof or a tautomeric form thereof, as defined above and optionally a pharmaceutically acceptable excipient or carrier.

The compound of formula (I), a pharmaceutically acceptable salt thereof or a tautomeric form thereof, is a neutralizing agent of CXCL12, and acts as an active agent in the pharmaceutical composition of the invention.

The compounds or the compositions of the invention can also be used as a pharmacological tool. The term "pharmacological tool" refers to a compound which functional properties allow to study how drugs interact with living organisms to produce a change in functions of interest, thereby allowing to study new drug composition and properties, interactions, toxicology, therapy, medical applications and antipathogenic capabilities. Furthermore, the term refers to a compound which may be used to characterize potential targets for the development of novel medicines, e.g. characterize their native composition, activation mechanisms, physiological functions, and roles in patho-physiology and disease.

Another subject of the invention is a composition as defined above for use for inhibiting the biological activity of chemokine CXCL12.

The present invention also relates to a composition as defined above, for use as a medicament.

In other embodiments, the pharmaceutical composition further comprises one or more biologically active agents. Examples of suitable biologically active agents include, but are not limited to, therapeutic agents such as anti-viral agents, anti-inflammatory agents, immunomodulatory agents, analgesics, antimicrobial agents, kinase inhibitors, signalling inhibitors, antibacterial agents, antibiotics, antioxidants, antiseptic agents, and combinations thereof.

It is also possible, according to the invention, to include at least one other active agent into the pharmaceutical composition of the invention. In such pharmaceutical compositions, the compound of formula (I) may be combined in one or more preparations for simultaneous, separate or sequential administration of the compound of formula (I) and the other active agent(s). More specifically, an inventive composition may be formulated in such a way that the compound of formula (I) and the other active agent(s) can be administered together or independently from each other. For example, a compound of formula (I) and the other active agent can be formulated together in a single composition. Alternatively, they may be maintained (e.g., in different compositions and/or containers) and administered separately.

Examples of active agents which can be used in combination with compound (I) of the invention are:

Bronchodilators:
beta 2 receptor agonists including non exclusively: SABA (short acting beta2 agonists): albuterol, levalbuterol, salbutamol, levosalbutamol, terbutaline, pirbuterol, procaterol, clinbuterol, fenoterol, metaproterenol, bitolterol mesylate, ritodrine, isoprenaline, LABA (long acting beta2 agonists), salmeterol, formoterol, indacaterol, bambuterol, olodaterol, vilanterol, arformoterol etc . . . , muscarinic antagonists: anticholinergics like ipratropium, diphenhydramine, aclidinium bromide, LAMA (long acting muscarinic antagonists) including non exclusively tiotropium bromide, aclidinium etc . . . , Anti-inflammatory corticosteroids (oral, inhaled, topical) including non exclusively beclomethasone, budesonide, ciclesonide, flunisolide, fluticasone, mometasone, etc, or oral like cortisol, cortisone, prednisone, prednisolone, methylprednisolone, hydrocortisone, dexamethasone, betamethasone, triamcinolone, beclomethasone, fludrocortisone, etc . . . , Antihistamines (oral or topical) including non exclusively hydroxyzine, diphenhydramine, chlorpheniramine, ketotifen, olopatadine, cetirizine, levocetirizine, ebastine, azelastine, fexofenadine, loratadine, desloratadine, mizolastine, etc . . . , Immunomodulators including non exclusively tacrolimus, pimecrolimus, everolimus, methotrexate, azathioprine, cyclosporine, mycophenolate mofetil, leflunomide, cyclophosphamide etc . . . , Bio-actives including non exclusively omalizumab and anti-IgE antibodies, mepolizumab and anti-IL-5 antibodies, dupilumab and anti-IL-4 and anti-IL-13 treatments, belimumab and anti-BLyS agents, etc . . . , Mast cell stabilizers including non exclusively nedocromil sodium, sodium cromoglycate, lodoxamide, etc . . . , Kinase inhibitors including non exclusively imatinib, masatinib, etc . . . , Nonsteroidal anti-inflammatory drugs including non exclusively ibuprofen, naproxen, aspirine, acetaminophen, indomethacin, nabumetone, celecoxib, etc . . . , Phosphodiesterase inhibitors including non exclusively roflumilast, theophylline and derivatives (aminophylline . . . ), etc . . . , Actives for pulmonary hypertension including non exclusively epoprostenol, bosentan, macitentan, iloprost, sildenafil, treprostinil, etc . . . , Actives for lupus including non exclusively antimalarial agents, such as hydroxychloroquine, chloroquine, corticosteroids such as prednisone, and immunosuppressant such as methotrexate, azathioprine, cyclophosphamide, mycophenolic acid, etc . . . , Actives for hyperalgesia and pain including non exclusively drugs such as selective serotonin-reuptake inhibitors or tricyclic antidepressants, gabapentin, pregabalin, NMDA antagonists, atypical opioids such as tramadol, etc . . . .

For instance, the compounds, compositions and methods of the present invention can be used to treat inflammatory diseases or conditions or inflammations associated with:

an allergic disease including hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy, allergic rhinitis, food allergy, etc;

a respiratory system disease including chronic lung disease, asthma, chronic obstructive pulmonary disease, chronic bronchitis rhinitis, pulmonary arterial hypertension (PAH), rare diseases associated with hypereosinophilia (such as hypereosinophilic syndromes, eosinophilic bronchiolitis, Churg-Strauss syndrome or eosinophilic granulomatosis with polyangeiitis), obliterative bronchiolitis and chronic lung allograft dysfunction, etc;

a central or peripheral nervous system disease;

a pain-related disorder including neuropathic or neurological pain, chronic pain, acute pain, migraine, headache inflammatory pain, post-operative pain, pain due to multiple sclerosis, Parkinson's disease or other neurological or autoimmune disorder, hyperalgesia induced by stress or by opioids or other;

an auto-immune disease including eosinophilic granulomatosis with polyangiitis or polyarteritis nodosa asthma, hypersensitivity pneumonitis, interstitial lung disease, sarcoidosis, idiopathic pulmonary fibrosis, lupus, Sjögren disease, non-limiting examples of auto-immune renal diseases including antibody mediated glomerulopathy as acute glomerulonephritis, nephritis associated with systemic lupus erythematosus, nephritis associated with other systemic diseases, non-limiting examples of auto-immune gastrointestinal diseases including Crohn's Disease, ulcerative colitis, coeliac disease, Whipple's disease, non-limiting examples of auto-immune hepatobiliary diseases including auto-immune hepatitis, alcohol-induced hepatitis, non-limiting examples of auto-immune skin diseases including psoriasis, atopic dermatitis, eczema, allergic skin disease, progressive systemic sclerosis (scleroderma), exfoliating dermatitis, pemphigus vulgaris, multiple sclerosis, etc.

More particularly, the compound of formula (I) and the composition of the invention can be used for prevention and/or treatment of a disease chosen in the group comprising asthma, atopic dermatitis, allergic rhinitis, atopic conjunctivitis, rhinoconjunctivitis, chronic obstructive pulmonary disease (COPD), lupus, Sjögren syndrome, hyperalgesia/pain, pulmonary hypertension (PH), obliterative bronchiolitis and chronic lung allograft dysfunction, chronic inflammatory diseases (such as rhumatoid arthritis), inflammatory bowel disease, WHIM syndrome (Warts, Hypogammaglobulinemia, Immunodeficiency and Myelokathexis syndrome) and rare diseases associated with hypereosinophilia (such as hypereosinophilic syndromes, eosinophilic bronchiolitis, Churg-Strauss syndrome or eosinophilic granulomatosis with polyangeiitis).

The present invention also relates to a method of treating a disease or a condition that involves CXCL12, comprising administering to a patient, in need of said treatment, a compound according to formula (I), a pharmaceutically acceptable salt thereof or a tautomeric form thereof, or a pharmaceutical composition comprising a compound of formula (I), a salt thereof or a tautomeric form thereof, in a therapeutically effective amount.

As used herein, the term "treatment" and the related terms "treat" and "treating" are used herein to characterize a method or process that is aimed at (1) delaying or preventing the onset of a disease, disorder or condition; (2) slowing down or stopping the progression, aggravator deterioration of the disease, disorder or condition; (3) bringing about amelioration of the symptoms of the disease, disorder or condition; or (4) curing the disease, disorder or condition.

The term refers to both prophylactic or preventive treatment as well as curative or palliative treatment. Thus, the term encompasses situations where disease, disorder or condition is already being experienced by a subject or patient, as well as situations where disease, disorder or condition is not currently being experienced but is expected to arise.

The term "patient" refers to a warm-blood animal, preferably a human being, i.e. a subject of any gender and at any stage development (i.e. neonate, infant, juvenile, adolescent, adult).

Administration of the compounds of formula (I) of the invention, pharmaceutically acceptable salts thereof or tautomeric forms thereof, in pure form or in an appropriate pharmaceutical composition, can be carried out via any of the accepted modes of administration or agents for serving similar utilities.

Thus, administration can be, for example, by the oral, sublingual, nasal, parenteral (intravenous, intramuscular, or subcutaneous), topical, transdermal, intravaginal, intravesical, or rectal routes, in the form of solid, semi-solid, lyophilized powder or liquid dosage forms, such as for example, tablets, suppositories, pills, soft elastic and hard gelatin capsules, powders, solutions, suspensions, sirup, nebulizations, aerosols or the like, preferably in unit dosage forms suitable for simple administration of precise dosages.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge.

Compounds of formula (I) can be prepared using art recognized methods.

In particular, the following general procedures A, B and C can be used.

General Procedure A

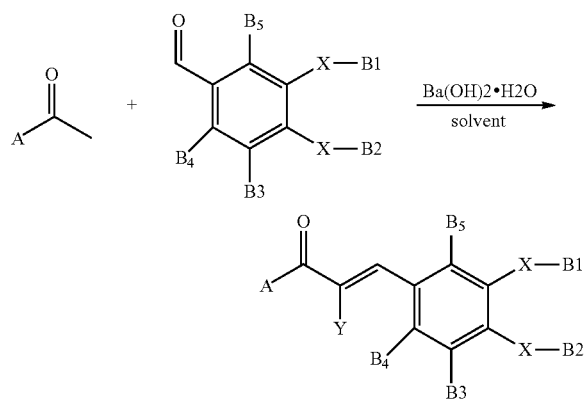

General Procedure B

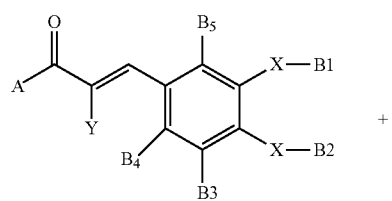

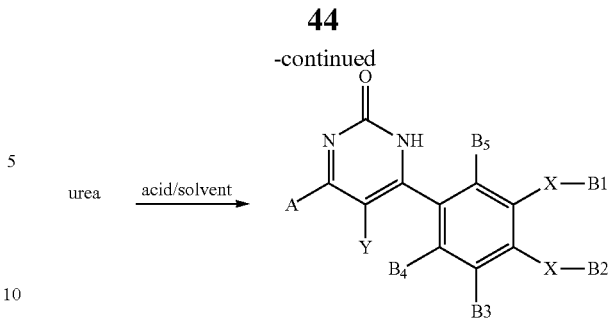

General procedure C

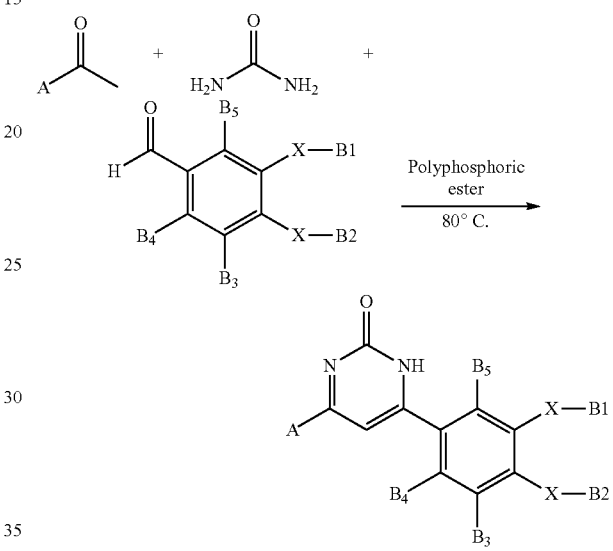

Further aspects and advantages of this invention will be disclosed in the following figures and examples, which should be regarded as illustrative and not limiting the scope of this application.

Figure 1:
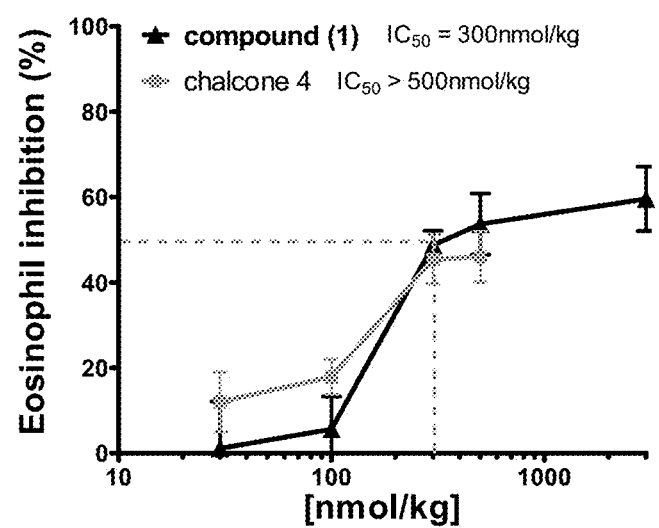
FIG. 1: Asthma

In vivo dose-response effect of a topical treatment with chalcone-4 and compound (1) of formula (I) in an 8-day mouse model of allergic eosinophilic airway inflammation. Balb/c mice were sensitized to ovalbumin (OVA, 50 μg) in the presence of 2 mg alum (IP. injection on days 0, 1 and 2) and challenged with OVA (10 μg) or saline (IN.) on days 6, 7 and 8. Increasing doses of chalcone-4 (gray line) or compound (1) (black line) solubilized in 10% hydroxypropyl-B-cyclodextrine (Cdx) were administered by the intranasal route 2 h before each challenge. Bronchoalveolar lavage was performed 24 h after the last challenge, and inflammatory cells including eosinophils counted. The percentage of inhibition of eosinophil recruitment is shown. Data points are means and bars are S.E.M. values of n=6 determinations.

FIG. 2: Atopic dermatitis

Figure 2A:
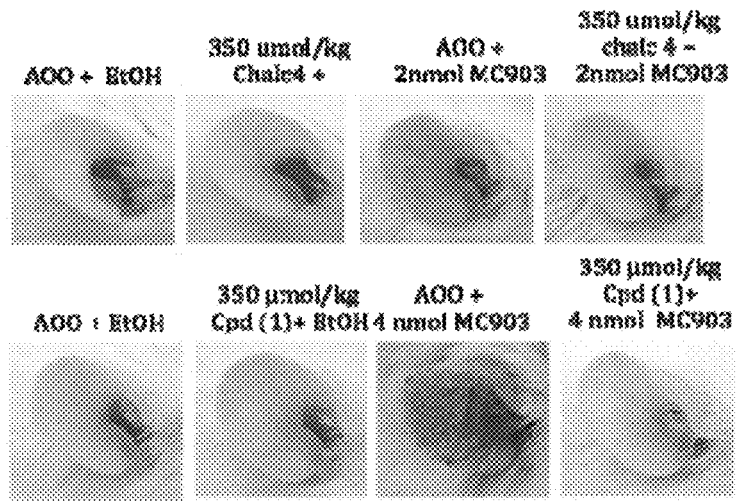

FIG. 2A. In vivo effect of a topical treatment with chalcone 4 and compound (1). Mouse ears were treated with MC903 (calcipotriol, 2 nmol/ear or 4 nmol/ear) or its solvent (ethanol EtOH) together with 350 μmol/kg chalcone 4 (upper row of images) or compound (1) (lower row of images) or solvent (acetone/olive oil 50/50, AOO). Chalcone 4 and compound (1) were dissolved in AOO and administered topically 2 h before each MC903 application. MC903 was dissolved in EtOH and topically applied.

Figure 2B:
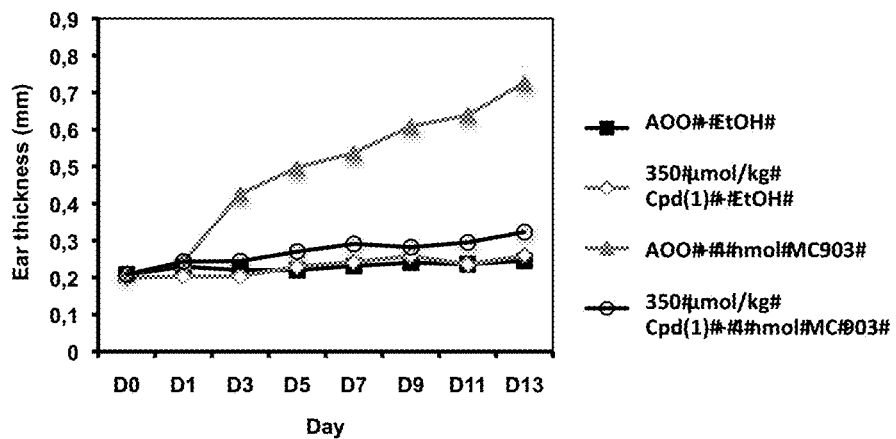

FIG. 2B. Increase in ear thickness over time (D1-D13) was determined with a caliper on animals treated with MC903 or solvent (EtOH), and compound (1) or solvent (AOO) as described for FIG. 2A. Data points are means and bars are S.E.M. values of n=6 determinations. Compound (1) inhibits atopic dermatitis induced by MC903 in this murine model.

Figure 2C:
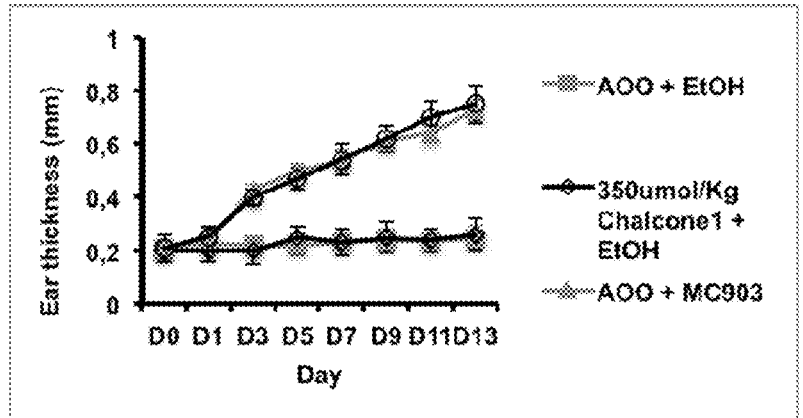

FIG. 2C. Increase in ear thickness over time (D1-D13) was determined with a caliper on animals treated with MC903 or solvent (EtOH) and Chalcone 1 or solvent (AOO). Data points are means and bars are S.E.M. values of n=6 determinations. Chalcone 1 is the inactive analogue of chalcone 4. It does not inhibit atopic dermatitis induced by MC903 in this murine model.

FIG. 3: COPD

In vivo effect of a systemic treatment with chalcone-4 or compound (1) in a LPS-induced mouse model of neutrophilic airway inflammation. Balb/c mice were administered intranasally with LPS (1 µg, white block) or saline (control). Chalcone-4 (gray block) or compound (1) (black block) (350 µmol/kg each) suspended in 1% CMC or solvent (CMC alone) were administered intraperitoneally 2 h before LPS. Neutrophil recruitment is shown, inhibited by chalcone 4 and compound (1). Data points are means and bars are S.E.M. values of n=6 determinations.

FIG. 4: Lupus

Effect of compound (1) and classical anti-inflammatory drugs on peripheral hypercellularity in MRL/lpr mice. MRL/lpr mice (11-13 week-old) received intravenously a single administration of either compound (1) or chalcone 4-Phosphate or indicated molecules in saline (100 µg/mouse of each). The control group received saline only. The number of white blood cells (WBCs)/mL was evaluated by counting cells five days later. The results are expressed as the mean reduction of peripheral WBCs percentage+/−SEM. Statistical significance was assessed using the unpaired t-test. n=number of mice/group; ns=non-significant.

Figure 5:
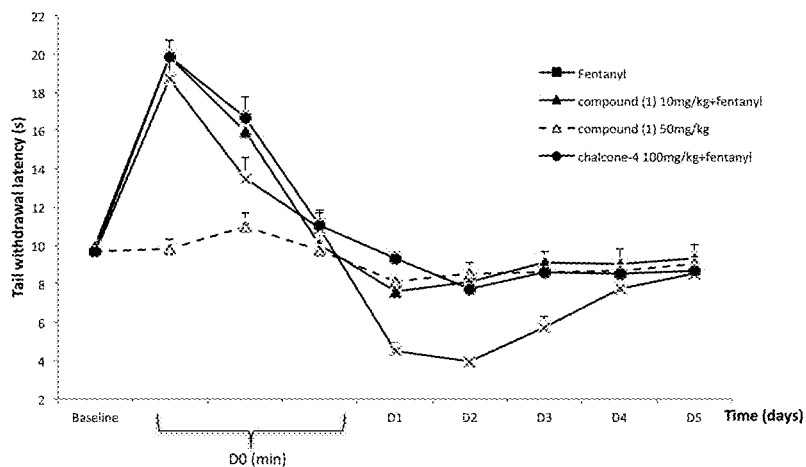

FIG. 5: Hyperalgesia

In vivo effect of compound (1) or chalcone-4 in the model of fentanyl-induced hyperalgesia in mice. Fentanyl was administered on day 0 (240 µg, s.c.) alone (closed squares) or in combination with compound (1) (10 mg/kg, i.p., closed triangles) or chalcone-4 (100 mg/kg, i.p., closed circles). Compound (1) was also tested alone at 50 mg/kg (i.p.) (open triangles). Chalcone-4 and compound (1) were suspended in 1% CMC and administered intraperitoneally 20 min before fentanyl administration. The nociceptive threshold was measured in the tail immersion test on day 0 at 60, 120 and 180 min after fentanyl administration and once a day (D1 to D5) until nociceptive values returned back to basal values of naive animals (D5). In the absence of any nociceptive reaction, a cut-off of 25 sec was set to prevent tissue damage. Values are represented as means S.E.M. (n=9 per group). Results were stastistically compared to the fentanyl group treated with solvent.

FIG. 6: Pulmonary hypertension (PH)

Figure 6A:
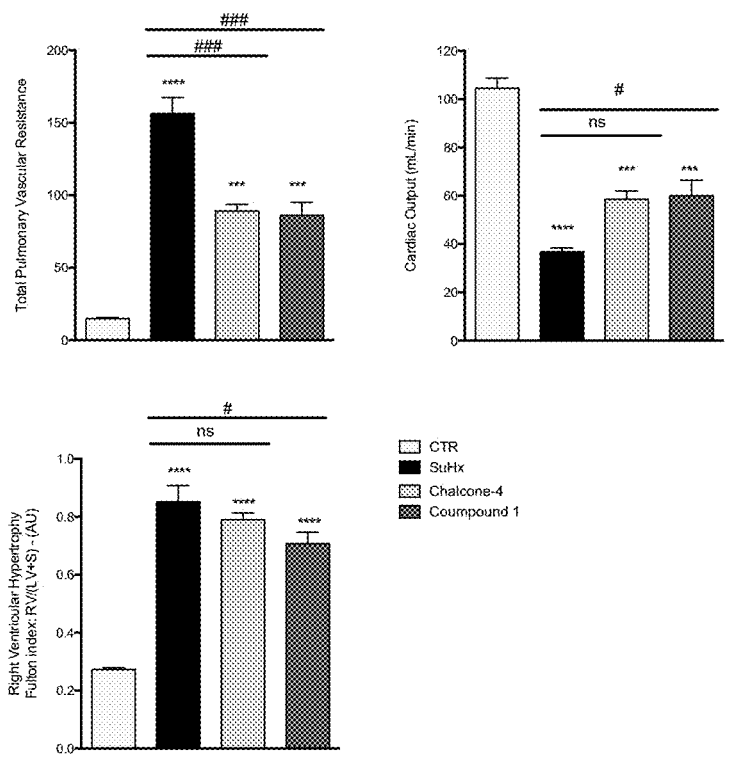

FIG. 6A: In vivo effect of chalcone-4 and compound (1) in the SU-5416 (20 mg/kg)/Hypoxia (SuHx) rat model of PH on total pulmonary vascular resistance, cardiac output and right ventricular hypertrophy. Male Wistar rats (100 g upon arrival in the laboratory; Janvier Labs, France) served as experimental subjects. SU-5416 (20 mg/kg) was injected subcutaneously and the rats were placed in normobaric hypoxia (10% $FiO_2$) for 3 weeks for PH to develop, and were then left for 2 weeks in normoxia. Rats were treated either with chalcone-4 or compound (1) at a dose of 100 mg/kg i.p. as compared with vehicle-treated SuHx rats. In addition, a group of healthy rats with no PH were used as the control group (CTR). The total pulmonary vascular resistance (TPVR), cardiac output (CO), right ventricular hypertrophy (RVH) assessed by the Fulton index [right/(left+septum) ventricular weight] were obtained in CTR and SuHx rats treated with chalcone-4 and compound (1). The bar graph represents means SEM. * p-value <0.001, ** p-value <0.0001 versus CTR rats. # p-value <0.05,### p-value <0.001 versus vehicle-treated SuHx rats.

Figure 6B:
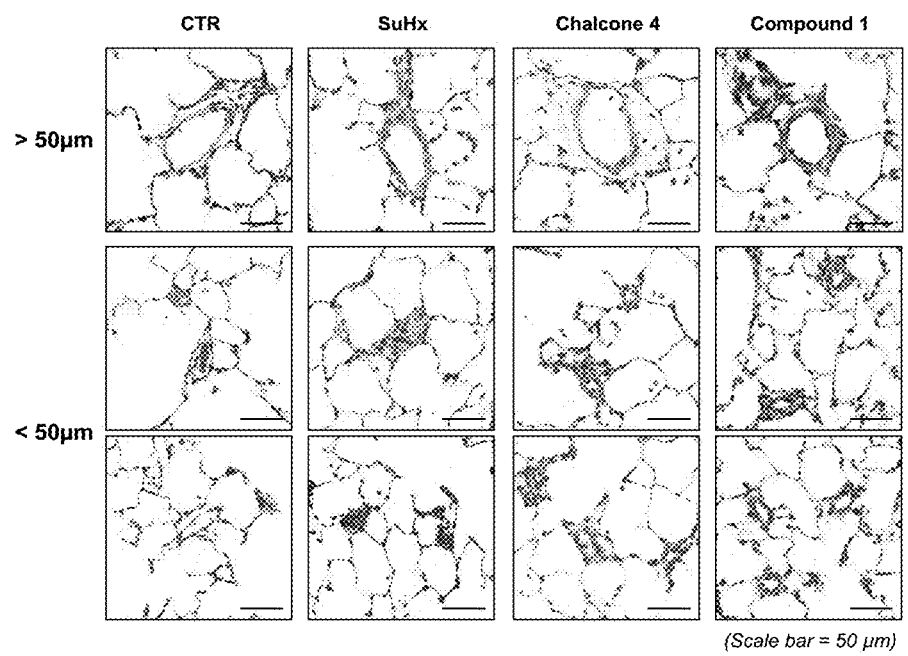

FIG. 6B: Representative photographs of hematoxylin-eosin (H&E) staining of lung paraffin-sections of SuHx rats treated with chalcone-4 and compound (1) when compared with the SuHx rats treated with vehicle. CTR: control rats with no PH. Scale Bar: 50 m.

Figure 6C:
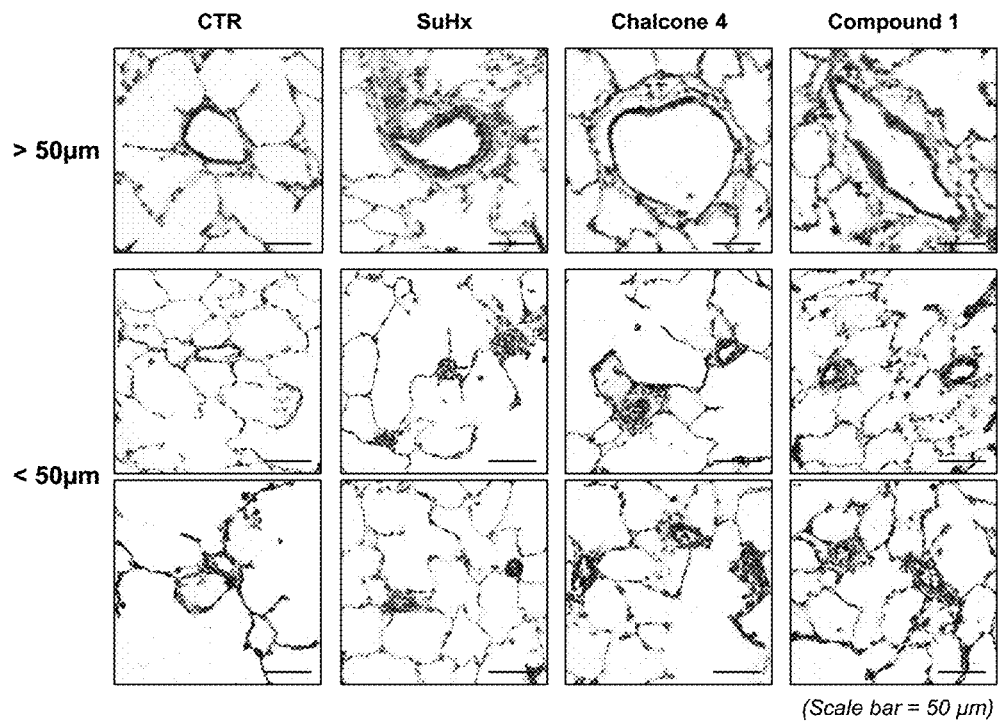

FIG. 6C: Representative photographs of alpha smooth muscle-actin (uSMA) staining of lung paraffin-sections of SuHx rats treated with chalcone-4 and compound (1) when compared with the SuHx rats treated with vehicle. CTR: control rats with no PH. Scale Bar: 50 m.

EXAMPLES

Example 1: General Synthesis Protocol of Compounds of General Formula (I)

General Methods

Reagents were obtained from commercial sources and used without any further purification. Thin-layer chromatography was performed on silica gel 60F254 plates. Flash chromatography was performed on silica gel cartridges (SiliaSep Flash cartridges silica, 40-63 µm) or RP18 prepacked columns (PuriFlash® 30 µm, Interchim) prepacked columns using a Spot II Ultimate apparatus from Armen Instrument. Semi-preparative RP-HPLC were performed on one of the following columns: SunFire™ C18 OBD™ (5 µm, 19×150 mm, Waters®) or SymmetryShield™ RP 18 (7 µm, 19×300 mm, Waters®) on PLC2020 from Gilson® using MeCN-0.1% TFA/water-0.1% TFA gradient (flow rate: 15 mL/min) unless otherwise specified.

$^1$H and $^{13}$C NMR spectra were recorded on a Bruker 400 MHz/100 MHz, 300 MHz/75 MHz and 200 MHz/50 MHz spectrometer. Conditions are specified for each spectrum (temperature 25° C. unless specified). Chemical shifts are reported in parts per million (ppm) relative to residual solvent and coupling constants (J) are reported in hertz (Hz). Signals are described as s (singlet), d (doublet), t (triplet), q (quartet), m (multiplet), dd (doublet of doublets), dt (doublet of triplets), dq (doublet of quadruplets) and br s (broad singlet).

Analytical HPLC analyses were performed on an Agilent 1000 series apparatus, equipped with an Ascentis Express C18 column (2.7 µm, 4.6×7.5 mm, Waters®) using MeCN-0.1% TFA/water-0.1% TFA gradient (flow rate: 1.6 mL/min). For each compound, HPLC purity was ≥97%. LC/MS spectra were obtained on an Agilent HPLC single quadrupole spectrometer (1200RRLC/1956b-SL) equipped with a THERMO Hypersyl column (1.9 µm, 1×30 mm) using an Agilent Multimode ion source. HRMS spectra were obtained on an Accurate-Mass Q-TOF spectrometer from Agilent using electrospray ionisation (ESI).

General Procedures

Chalcone Synthesis Under Basic Conditions—General Procedure A

To a solution of the desired substituted benzaldehyde (2.00 mmol, 1 equiv) and acetophenone (2.00 mmol, 1 equiv) derivatives in EtOH (5 mL), was added Ba(OH)$_2$.H$_2$O (4.000 mmol, 2 equiv). The reaction was stirred at room temperature (rt). After completion of the reaction, the mixture was evaporated under reduced pressure. Water was added to the residue and the mixture was extracted three times with EtOAc or CH$_2$Cl$_2$. The combined organic layers were dried over anhydrous sodium Na$_2$SO$_4$, filtered and concentrated. Purification on a silica gel column or semi-preparative HPLC afforded the desired product.

4,6-diaryl pyrimidin-2(1H)-one synthesis—General Procedure B

To a solution of chalcone (1 equiv) in EtOH was added urea (10 equiv) and HCl 4M in dioxane. The mixture was allowed to reflux for 2 h. The reaction was then concentrated and the residue was purified on a silica gel column eluting with 0-10% MeOH in CH$_2$Cl$_2$ to afford after freeze-drying a powder.

Application to the Synthesis of Compound (1) of Formula (I)

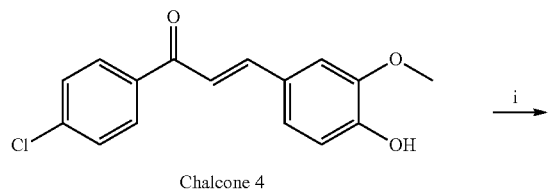

Chalcone 4

Reagents and conditions: (i) urea, HCl, dioxane/EtOH, 100° C., 2 h, 43%.

One Pot 4,6-Diaryl Pyrimidin-2(1H)-One Synthesis—General Procedure C

In a sealed tube was added acetophenone (1 equiv), urea (1.5 equiv), vanillin (1 equiv) and polyphosphoric ester (0.3 equiv) in EtOH. The reaction mixture was stirred overnight at 80° C. The reaction was then concentrated and the residue was purified either on a silica gel column eluting with 0-10% MeOH in CH$_2$Cl$_2$ or on a reverse phase column eluting with 5-95% CH$_3$CN in H$_2$O to afford after freeze-drying a powder.

(E)-1-(4-Chlorophenyl)-3-(4-hydroxy-3-methoxyphenyl)prop-2-en-1-one (Chalcone-4)

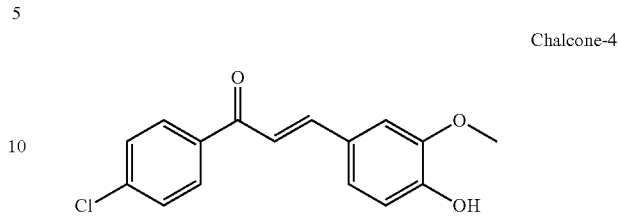

Chalcone-4

To a solution of 4-hydroxy-3-methoxybenzaldehyde (4.920 g, 32.34 mmol) and 1-(4-chlorophenyl)ethan-1-one (5.000 g, 32.34 mmol) in EtOH (16 mL) at 0° C., was slowly added SOCl$_2$ (1.650 mL, 22.75 mmol). The mixture was allowed to warm to room temperature and was stirred overnight. Water was added to the solution and the mixture was extracted 2 times with CH$_2$Cl$_2$. The combined organic layers were dried over anhydrous Na$_2$SO$_4$, filtered and concentrated. The solid was recrystallized from EtOH to give a yellow solid (7.368 g, 25.49 mmol, 79%).

$^1$H NMR (400 MHz, CDCl$_3$) δ 7.88 (d, J=8.6 Hz, 2H), 7.66 (d, J=15.5 Hz, 1H), 7.41 (d, J=8.6 Hz, 2H), 7.25 (d, J=15.5 Hz, 1H), 7.21 (dd, J=8.2 Hz, J=1.9 Hz, 1H), 7.17 (d, J=1.9 Hz, 1H), 6.93 (d, J=8.2 Hz, 1H), 5.89 (s, 1H), 3.95 (s, 3H); $^{13}$C NMR (100 MHz, CDCl$_3$) δ 189.5, 148.7, 147.0, 145.9, 139.1, 137.0, 130.0, 129.0, 127.5, 123.8, 119.4, 115.1, 110.3, 56.2; HRMS (ESI-TOF): calcd for C$_{16}$H$_{14}$ClO$_3$ [M+H]$^+$: 289.0632, found: 289.0636.

4-(4-Chlorophenyl)-6-(4-hydroxy-3-methoxyphenyl)pyrimidin-2(1H)-one (1)

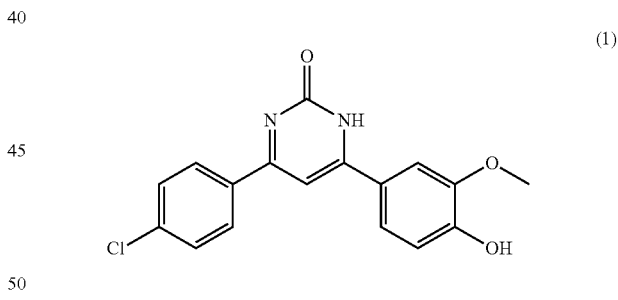

(1)

To a solution of (E)-1-(4-chlorophenyl)-3-(4-hydroxy-3-methoxyphenyl)prop-2-en-1-one (Chalcone-4) (100 mg, 0.34 mmol, 1 equiv) in EtOH (1.240 mL) was added urea (204 mg, 3.40 mmol, 10 equiv) and HCl in dioxane (840 μL, 4M). The mixture was allowed to reflux for 2 h. The reaction was then concentrated and the residue was purified on a silica gel column eluting with 0-10% MeOH in CH$_2$Cl$_2$ to afford after freeze-drying an orange powder (48 mg, 0.15 mmol, 43%).

$^1$H NMR (400 MHz, DMSO-d$_6$) δ 9.98 (br s, 1H), 8.18 (d, J=8.7 Hz, 2H), 7.73 (d, J=6.2 Hz, 1H), 7.71 (s, 1H), 7.64 (d, J=8.7 Hz, 2H), 7.51 (br s, 1H), 6.93 (d, J=6.2 Hz, 1H), 3.90 (s, 3H); $^{13}$C NMR (100 MHz, DMSO-d$_6$) δ 163.7, 163.2, 160.6, 152.8, 148.2, 137.8, 131.1, 130.4, 129.2, 123.8, 121.6, 116.0, 112.1, δ 99.8, 56.1; HRMS (ESI-TOF): calcd for C$_{17}$H$_{13}$ClN$_2$O$_3$ [M+H]$^+$: 329.0693, found: 329.0688.

(E)-3-(4-hydroxy-3-methoxyphenyl)-1-(4-methoxyphenyl)prop-2-en-1-one "2a"

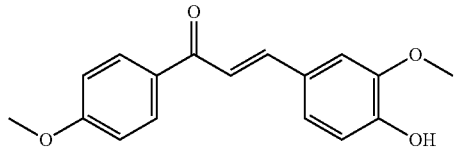

Synthesis was performed following general procedure A, from 4'-methoxyacetophenone (1.00 g, 6.66 mmol) and vanillin (1.01 g, 6.66 mmol). The residue was recrystallized from EtOH to afford the desired product (1.15 g, 4.05 mmol, 61%) as an orange solid.

$^1$H NMR (400 MHz, DMSO-d$_6$) δ 9.66 (s, 1H), 8.16 (d, J=9.0 Hz, 2H), 7.72 (ABq, Δδ$_{AB}$=0.102, J$_{AB}$=15.3 Hz, 2H), 7.52 (d, J=2.0 Hz, 1H), 7.28 (dd, J=8.3 Hz, 2.01 Hz, 1H), 7.08 (d, J=9.0 Hz, 2H), 6.86 (d, J=8.3 Hz, 1H), 3.89 (s, 3H), 3.86 (s, 3H); $^{13}$C NMR (101 MHz, DMSO-d$_6$) δ 187.8, 163.5, 150.0, 148.5, 144.5, 131.3, 131.2, 126.9, 124.4, 119.2, 116.1, 114.4, 112.2, 56.3, 56.0; RT: 4.53 min.

(E)-3-(4-hydroxy-3-methoxyphenyl)-1-(4-hydroxyphenyl)prop-2-en-1-one "3a"

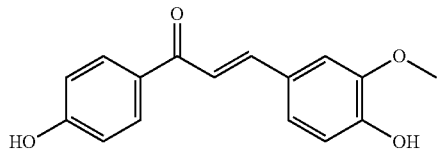

Synthesis was performed following general procedure A, from 4'-hydroxyacetophenone (2.00 g, 14.69 mmol) and vanillin (2.23 g, 14.69 mmol). The residue was recrystallized from EtOH/H$_2$O to afford the desired product (1.11 g, 4.11 mmol, 28%) as an orange solid.

$^1$H NMR (400 MHz, DMSO-d$_6$) δ 10.34 (s, 1H), 9.62 (s, 1H), 8.06 (d, J=7.9 Hz, 2H), 7.67 (ABq, Δδ$_{AB}$=0.032, J$_{AB}$=15.5 Hz, 2H), 7.49 (d, J=2.0 Hz, 1H), 7.24 (dd, J=8.4, 1.9 Hz, 1H), 6.89 (d, J=4.8 Hz, 2H), 6.82 (d, J=8.0 Hz, 1H), 3.87 (s, 3H); $^{13}$C NMR (101 MHz, DMSO-d$_6$) δ 187.0, 161.8, 149.3, 147.9, 143.5, 130.9, 129.4, 126.4, 123.7, 118.7, 115.5, 115.2, 111.5, 55.8; RT: 3.67 min.

(E)-3-(4-hydroxy-3-methoxyphenyl)-1-(4-isopropylphenyl)prop-2-en-1-one "4a"

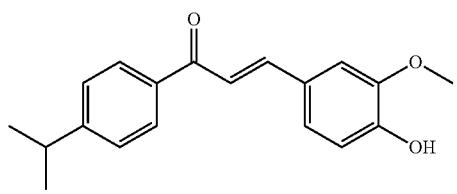

Synthesis was performed following general procedure A, from 4'-isopropylacetophenone (1.94 g, 11.96 mmol) and vanillin (1.82 g, 11.96 mmol). The residue was purified on silica gel (30% EtOAc in n-heptane) to afford the desired product (2.47 g, 8.33 mmol, 70%) as an orange oil.

$^1$H NMR (400 MHz, CDCl$_3$) δ 7.86 (m, 2H), 7.64 (d, J=15 Hz, 1H), 7.28 (d, J=15 Hz, 1H), 7.23 (m, J=6 Hz, 2H), 7.09 (dd, J=8, 2 Hz, 1H), 7.02 (d, J=2 Hz, 1H), 6.85 (d, J=8 Hz, 1H), 6.24 (bs, 1H), 3.81 (s, 3H), 2.87 (sp, J=7 Hz, 1H), 1.18 (d, J=7 Hz, 6H); $^{13}$C NMR (101 MHz, CDCl$_3$) δ 144.9, 128.7, 126.7, 123.3, 119.8, 115.0, 110.2, 56.0, 34.3, 23.7; RT: 5.55 min.

(E)-1-(4-fluorophenyl)-3-(4-hydroxy-3-methoxyphenyl)prop-2-en-1-one "5a"

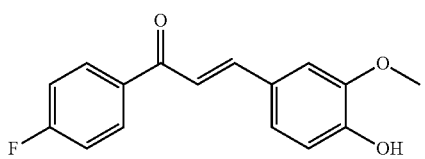

Synthesis was performed following general procedure A, from 4'-fluoroacetophenone (2.00 g, 14.48 mmol) and vanillin (2.20 g, 14.48 mmol). The residue was purified on silica gel (40% EtOAc in n-heptane) to afford the desired product (3.43 g, 12.59 mmol, 87%) as a yellow solid.

$^1$H NMR (400 MHz, CDCl$_3$) δ 7.98-7.94 (m, 2H), 7.67 (d, J=15 Hz, 1H), 7.26 (d, J=15 Hz, 1H), 7.18-7.04 (m, 4H), 6.87 (d, J=8 Hz, 1H), 5.98 (s, 1H), 3.87 (s, 3H); $^{13}$C NMR (101 MHz, CDCl$_3$) δ 145.5, 130.9, 119.3, 115.8, 115.6, 114.9, 110.1, 56.0 RT: 4.73 min.

(E)-3-(4-hydroxy-3-methoxyphenyl)-1-(4-iodophenyl)prop-2-en-1-one "6a"

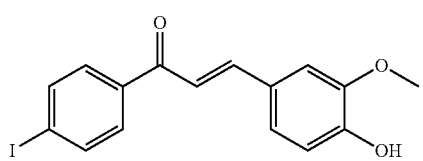

Synthesis was performed following general procedure A, from 4-iodoacetophenone (2.00 g, 8.13 mmol) and vanillin (1.24 g, 8.13 mmol). The residue was recrystallized from EtOH to afford the desired product (2.61 g, 6.86 mmol, 84%) as an orange solid.

$^1$H NMR (400 MHz, CDCl$_3$) δ 7.79-7.77 (m, 2H), 7.69-7.63 (m, 3H), 7.22 (d, J=15 Hz, 1H), 7.13 (dd, J=8, 2 Hz, 1H), 7.04 (d, J=2 Hz, 1H), 6.88 (d, J=8 Hz, 1H), 3.88 (s, 3H); $^{13}$C NMR (101 MHz, CDCl$_3$) δ 145.8, 137.9, 129.9, 123.5, 119.2, 114.9, 110.1, 56.1; RT: 5.45 min.

(E)-1-(2-chlorophenyl)-3-(4-hydroxy-3-methoxyphenyl)prop-2-en-1-one "7a"

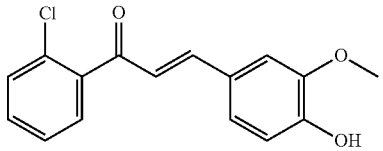

7a

Synthesis was performed following general procedure A, from 2'-chloroacetophenone (2.00 g, 12.94 mmol) and vanillin (1.97 g, 12.94 mmol). The residue was purified on silica gel (30% EtOAc in n-heptane) to afford the desired product (1.87 g, 6.48 mmol, 50%) as a brown oil.

$^1$H NMR (400 MHz, DMSO-$d_6$) δ 9.78 (s, 1H), 7.59-7.46 (m, 4H), 7.36 (d, J=1.8 Hz, 1H), 7.18 (ABq, Δδ$_{AB}$=0.066, J$_{AB}$=16.1 Hz, 2H), 7.16 (dd, J=8.4 Hz, 1.9 Hz, 1H), 6.80 (d, J=8.3 Hz, 1H), 3.81 (s, 3H); $^{13}$C NMR (101 MHz, DMSO-$d_6$) δ 193.2, 150.1, 148.0, 147.4, 139.1, 131.3, 129.9, 129.7, 128.9, 127.2, 125.5, 123.9, 123.3, 115.6, 111.8, 55.7; RT: 4.66 min.

(E)-3-(4-hydroxy-3-methoxyphenyl)-1-phenylprop-2-en-1-one "8a"

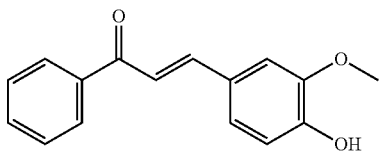

8a

Synthesis was performed following general procedure A, from acetophenone (1.00 g, 8.32 mmol) and vanillin (1.27 g, 8.32 mmol). The residue was purified on silica gel (30% EtOAc in n-heptane) to afford the desired product (1.68 g, 6.61 mmol, 79%) as a yellow solid.

$^1$H NMR (400 MHz, DMSO-$d_6$) δ 9.70 (s, 1H), 8.16-8.12 (m, 2H), 7.72 (ABq, Δδ$_{AB}$=0.017, J$_{AB}$=17.6 Hz, 2H), 7.67-7.63 (m, 1H), 7.59-7.54 (m, 2H), 7.52 (d, J=2.0 Hz, 1H), 7.28 (dd, J=8.3, 2.0 Hz, 1H), 6.84 (d, J=8.0 Hz, 1H), 3.87 (s, 3H); $^{13}$C NMR (101 MHz, DMSO-$d_6$) δ 189.0, 149.7, 148.0, 144.9, 138.0, 132.7, 128.6, 128.3, 126.2, 124.1, 118.7, 115.6, 111.7, 55.8; RT: 4.56 min.

(E)-1-(4-chlorophenyl)-3-(4-hydroxy-3-(trifluoromethoxy)phenyl)prop-2-en-1-one "9a"

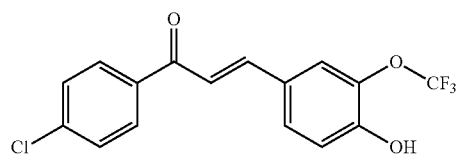

9a

Synthesis was performed following general procedure A, from 4'-chloroacetophenone (405 mg, 2.62 mmol) and 4-hydroxy-3-(trifluoromethoxy)benzaldehyde (540 mg, 2.62 mmol). The residue was purified on silica gel (30% EtOAc in n-heptane) to afford the desired product (785 mg, 2.29 mmol, 87%) as a yellow solid.

$^1$H NMR (400 MHz, CDCl$_3$) δ 7.87 (m, 2H), 7.64 (d, J=15.6 Hz, 1H), 7.41 (m, 2H), 7.34 (d, J=8.8 Hz, 1H), 7.27 (d, J=15.6 Hz, 1H), 7.01 (m, 2H); $^{13}$C NMR (101 MHz, CDCl$_3$) δ 144.1, 129.9, 129.6, 129.0, 128.7, 121.7, 120.6, 118.0; RT: 5.80 min.

(E)-1-(4-chlorophenyl)-3-(3-hydroxy-4-methoxyphenyl)prop-2-en-1-one "10a"

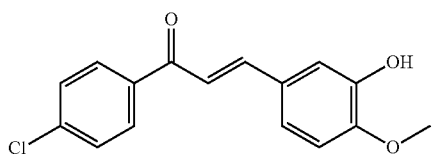

10a

Synthesis was performed following general procedure A, from 4'-chloroacetophenone (1.00 g, 6.47 mmol) and isovanilin (0.98 g, 6.47 mmol). The residue was purified on silica gel (30% EtOAc in n-heptane) to afford the desired product (1.73 g, 5.99 mmol, 93%) as a yellow solid.

$^1$H NMR (400 MHz, DMSO-$d_6$) δ 9.16 (s, 1H), 8.14 (d, J=8.8 Hz, 2H), 7.66 (d, J=4.0 Hz, 2H), 7.61 (d, J=7.7 Hz, 2H), 7.34 (d, J=2.3 Hz, 1H), 7.30 (dd, J=8.4, 2.1 Hz, 1H), 6.99 (d, J=8.5 Hz, 1H) 3.84 (s, 3H); $^{13}$C NMR (101 MHz, DMSO-$d_6$) δ 187.9, 150.4, 146.6, 145.0, 137.7, 136.5, 130.2, 128.8, 127.5, 122.2, 119.1, 114.9, 111.9, 55.7; RT: 5.17 min.

4-(4-methoxyphenyl)-6-(4-hydroxy-3-methoxyphenyl)-pyrimidin-2(1H)-one (2)

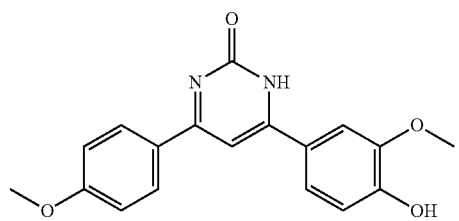

(2)

Synthesis was performed following general procedure B, from (E)-3-(4-hydroxy-3-methoxyphenyl)-1-(4-methoxyphenyl)prop-2-en-1-one (1.10 g, 3.87 mmol, 2a). The residue was purified on flash chromatography (5-50% MeCN in water) and evaporated to obtain the desired product (564 mg, 1.74 mmol, 45%) as an orange solid.

$^1$H NMR (400 MHz, DMSO-$d_6$) δ 9.81 (br s, 2H), 8.16 (br d, J=8.3 Hz, 2H), 7.77 (br d, J=8.5 Hz, 1H), 7.72 (s, 1H), 7.47 (s, 1H), 7.14 (br d, J=8.0 Hz, 2H), 6.99 (br d, J=8.3 Hz, 1H), 3.90 (s, 3H), 3.87 (s, 3H); $^{13}$C NMR (101 MHz, DMSO-$d_6$) δ 163.3, 163.0, 162.8, 158.4, 158.1, 152.3, 148.0, 130.5, 123.8, 123.4, 121.8, 115.9, 114.5, 111.8, 98.2, 56.0, 55.7; MS (ESI-TOF): m/z=325.0 [M+H]$^+$; RT: 3.05 min; mp: 271.2-273.2° C.

4-(4-hydroxyphenyl)-6-(4-hydroxy-3-methoxyphenyl)-pyrimidin-2(1H)-one (3)

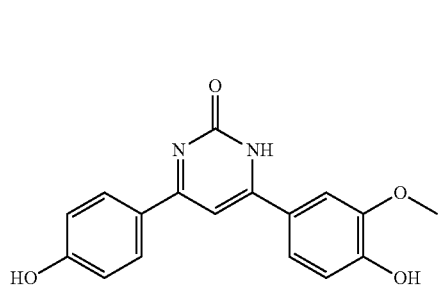

Synthesis was performed following general procedure B, from (2E)-3-(4-hydroxy-3-methoxyphenyl)-1-(4-hydroxyphenyl)prop-2-en-1-one (1.10 g, 4.07 mmol, 3a). The residue was recrystallized from EtOH to afford the desired product (429 mg, 1.38 mmol, 34%) as a red solid.

$^1$H NMR (400 MHz, DMSO-$d_6$) δ 11.10 (br s, 1H), 10.70 (br s, 1H), 8.13 (d, J=8.1 Hz, 2H), 7.83 (dd, J=8.5, 2.3 Hz, 1H), 7.75 (d, J=2.3 Hz, 1H), 7.53 (s, 1H), 7.09-7.03 (m, 3H), 3.92 (s, 3H); $^{13}$C NMR (101 MHz, DMSO-$d_6$) δ 163.8, 162.4, 162.4, 153.6, 150.1, 148.1, 131.6, 124.4, 119.8, 119.7, 116.3, 116.1, 112.4, 98.1, 56.1; MS (ESI-TOF): m/z=309.0 [M−H]$^−$; RT: 2.63 min; mp: 264.5-266.5° C.

4-(4-isopropylphenyl)-6-(4-hydroxy-3-methoxyphenyl)-pyrimidin-2(1H)-one (4)

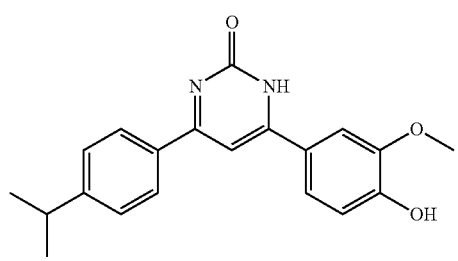

Synthesis was performed following general procedure B, from (E)-3-(4-hydroxy-3-methoxyphenyl)-1-(4-isopropylphenyl)prop-2-en-1-one (790 mg, 2.67 mmol, 4a). The residue was purified on flash chromatography (5-60% MeCN in water) and evaporated to obtain the desired product (100 mg, 0.30 mmol, 11%) as a yellow solid.

$^1$H NMR (400 MHz, DMSO-$d_6$) δ 11.80 (bs, 1H), 9.77 (bs, 1H), 8.05 (m, 2H), 7.70 (m, 2H), 7.42 (m, 3H), 6.91 (d, J=8.0 Hz, 1H), 3.90 (s, 3H), 2.99 (m, 1H), 1.25 (d, J=6.8 Hz, 6H); $^{13}$C NMR (101 MHz, DMSO-$d_6$) δ 128.1, 127.1, 121.9, 116.0, 111.5, 56.3, 33.8, 23.9; MS (ESI-TOF): m/z=337.0 [M+H]$^+$; RT: 3.80 min; mp: 261.8-263.0° C.

4-(4-fluorophenyl)-6-(4-hydroxy-3-methoxyphenyl) pyrimidin-2(1H)-one (5)

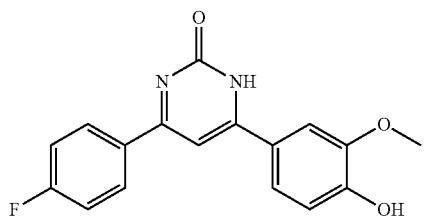

Synthesis was performed following general procedure B, from (E)-1-(4-fluorophenyl)-3-(4-hydroxy-3-methoxyphenyl)prop-2-en-1-one (1.50 g, 5.51 mmol, 5a). The residue was purified on flash chromatography (5-60% MeCN in water) and evaporated to obtain the desired product (147 mg, 0.47 mmol, 9%) as an orange solid.

$^1$H RMN (400 MHz, DMSO-$d_6$) δ 8.23 (t, J=5.5 Hz, 2H), 7.70 (m, 2H), 7.46 (s, 1H), 7.38 (t, J=8.5 Hz, 2H), 6.94 (d, J=8.5 Hz, 1H), 3.90 (s, 3H); $^{13}$C NMR (101 MHz, DMSO-$d_6$) δ 128.8, 128.7, 120.3, 114.2, 114.0, 109.7, 97.1, 54.2; MS (ESI-TOF): m/z=313.0 [M+H]$^+$; RT: 3.05 min; mp: 294.7-295.8° C.

4-(4-iodophenyl)-6-(4-hydroxy-3-methoxyphenyl)-pyrimidin-2(1H)-one (6)

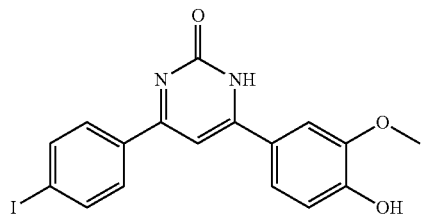

Synthesis was performed following general procedure B, from (E)-3-(4-hydroxy-3-methoxyphenyl)-1-(4-iodophenyl)prop-2-en-1-one (1.50 g, 3.95 mmol, 6a). The residue was purified on flash chromatography (5-60% MeCN in water) and evaporated to obtain the desired product (20 mg, 0.05 mmol, 1%) as an orange solid.

$^1$H NMR (400 MHz, DMSO-$d_6$) δ 7.95 (m, 4H), 7.69 (m, 2H), 7.48 (s, 1H), 6.92 (d, J=8.0 Hz, 1H), 3.90 (s, 3H); $^{13}$C NMR (101 MHz, DMSO-$d_6$) δ 138.1, 130.0, 122.2, 116.1, 111.7, 56.4; MS (ESI-TOF): m/z=420.0 [M+H]$^+$; RT: 3.68 min; mp: 302.8-303.4° C.

4-(2-chlorophenyl)-6-(4-hydroxy-3-methoxyphenyl) pyrimidin-2(1H)-one (7)

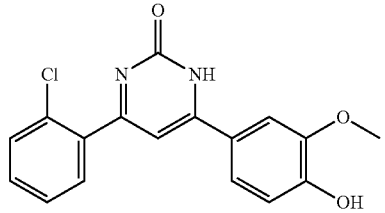

(7)

Synthesis was performed following general procedure B, from (2E)-1-(2-chlorophenyl)-3-(4-hydroxy-3-methoxyphenyl)prop-2-en-1-one (1.87 g, 6.48 mmol, 7a). The residue was purified on flash chromatography (5-50% MeCN in water) and evaporated to obtain the desired product (653 mg, 1.98 mmol, 31%) as a yellow solid.

$^1$H NMR (400 MHz, DMSO-$d_6$) δ 12.01 (br s, 1H), 9.83 (s, 1H), 7.70 (d, J=1.8 Hz, 1H), 7.67-7.59 (m, 3H), 7.57-7.47 (m, 2H), 7.12 (s, 1H), 6.89 (d, J=8.3 Hz, 1H), 3.86 (s, 3H); $^{13}$C NMR (101 MHz, DMSO-$d_6$) δ 150.5, 147.8, 131.4, 131.2, 130.9, 129.8, 127.4, 121.6, 115.5, 111.1, 55.7; MS (ESI-TOF): m/z=329.0 [M+H]$^+$; RT: 3.16 min; mp: 254.2-256.2° C.

4-(phenyl)-6-(4-hydroxy-3-methoxyphenyl)-pyrimidin-2(1H)-one (8)

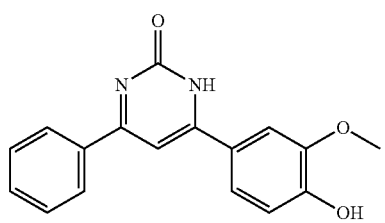

(8)

Synthesis was performed following general procedure B, from (2E)-3-(4-hydroxy-3-methoxyphenyl)-1-phenylprop-2-en-1-one (1.63 g, 6.41 mmol, 8a). The residue was purified on flash chromatography (5-50% MeCN in water) and evaporated to obtain the desired product (635 mg, 2.16 mmol, 34%) as a yellow solid.

$^1$H NMR (400 MHz, DMSO-$d_6$) δ 10.07 (br s, 1H), 8.13 (d, J=7.5 Hz, 2H), 7.76-7.71 (m, 2H), 7.65-7.55 (m, 3H), 7.48 (s, 1H), 6.96 (d, J=8.8 Hz, 1H), 5.52 (br s, 1H), 3.90 (s, 3H); $^{13}$C NMR (101 MHz, DMSO-$d_6$) δ 151.8, 148.4, 132.5, 129.4, 128.4, 122.9, 116.2, 111.9, 99.4, 56.4; MS (ESI-TOF): m/z=295.0 [M+H]$^+$; RT: 2.89 min; mp: 238.0-240.0° C.

4-(4-chlorophenyl)-6-(4-hydroxy-3-(trifluoromethoxy)phenyl)pyrimidin-2(1H)-one (9)

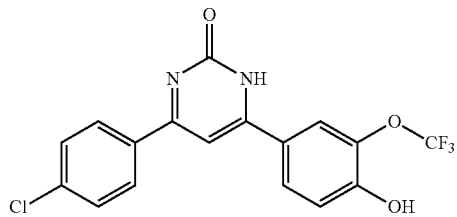

(9)

Synthesis was performed following general procedure B, from (E)-1-(4-chlorophenyl)-3-(4-hydroxy-3-(trifluoromethoxy)phenyl)prop-2-en-1-one (1.00 g, 2.92 mmol, 9a). The residue was purified on flash chromatography (5-60% MeCN in water) and evaporated to obtain the desired product (31 mg, 0.08 mmol, 3%) as a yellow solid.

$^1$H NMR (400 MHz, DMSO-$d_6$) δ 12.00 (bs, 1H), 11.00 (bs, 1H), 8.21-8.12 (m, 4H), 7.63 (m, 2H), 7.16 (d, J=8.4 Hz, 1H); $^{13}$C NMR (101 MHz, DMSO-$d_6$) δ 129.8, 129.3, 128.7, 123.0, 118.2; MS (ESI-TOF): m/z=483.0 [M+H]; RT: 4.28 min; mp: 283.5-285.2° C.

4-(4-chlorophenyl)-6-(3-hydroxy-4-methoxyphenyl) pyrimidin-2(1H)-one (10)

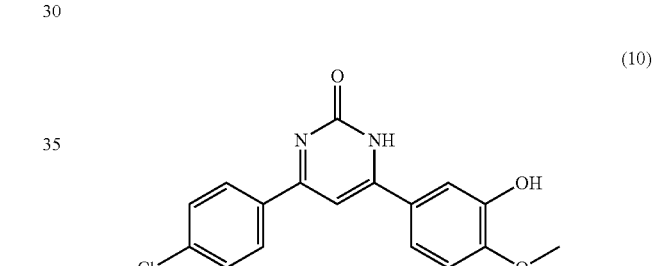

(10)

Synthesis was performed following general procedure B, from (2E)-1-(4-chlorophenyl)-3-(3-hydroxy-4-methoxyphenyl)prop-2-en-1-one (1.14 g, 3.95 mmol, 10a). The residue was recrystallized from EtOH/H$_2$O to afford the desired product (348 mg, 1.06 mmol, 27%) as an orange solid.

$^1$H NMR (400 MHz, DMSO-$d_6$) δ 8.69 (br s, 2H), 8.14 (br d, J=8.5 Hz, 2H), 7.77-7.72 (m, 1H), 7.67 (br d, J=8.0 Hz, 3H), 7.50 (s, 1H), 7.13 (br d, J=8.5 Hz, 1H), 3.89 (s, 3H); $^{13}$C NMR (101 MHz, DMSO-$d_6$) δ 164.4, 162.8, 161.7, 153.1, 147.0, 138.2, 130.6, 130.1, 129.1, 122.8, 122.0, 115.6, 112.1, 100.4, 56.1; MS (ESI-TOF): m/z=329.0 [M+H]$^+$; RT: 3.46 min; mp 287.2-289.2° C.

(2E)-1-(2,4-dimethoxyphenyl)-3-(4-hydroxy-3-methoxyphenyl)prop-2-en-1-one "11a"

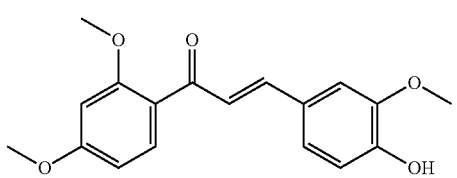

11a

Compound 11a was obtained following procedure A.

Isolated yield 75%. Tr: 4.39 min. ¹H NMR (400 MHz, CDCl₃) δ ppm 7.65 (d, J=8.5 Hz, 1H), 7.52 (d, J=15.5 Hz, 1H), 7.26 (d, J=15.5 Hz, 2H), 7.08 (d, J=8.1 Hz, 1H), 7.00 (s, 1H), 6.85 (d, J=8.1 Hz, 1H), 6.48 (dd, J=8.5, 1.26 Hz, 1H), 6.43 (s, 1H), 5.95 (s, 1H), 3.85 (s, 3H), 3.82 (s, 3H), 3.79 (s, 3H) ¹³C NMR (101 MHz, CDCl₃) δ ppm 190.8, 163.9, 160.2, 147.8, 146.7, 142.7, 132.6, 128.0, 125.0, 122.8, 122.5, 114.8, 114.4, 110.2, 105.1, 98.7, 55.9, 55.7, 55.5.

4-(2,4-dimethoxyphenyl)-6-(4-hydroxy-3-methoxyphenyl)-1,2-dihydropyrimidin-2-one (11)

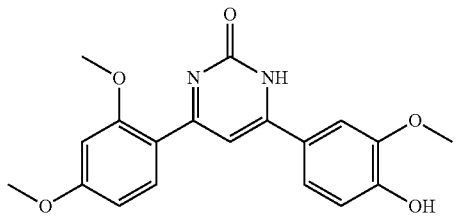

(11)

Compound (11) is obtained from compound 11a following general procedure B.

Isolated yield: 21%. rt: 3.21 min. ¹H NMR (400 MHz, DMSO-d₆) δ ppm 7.66-7.76 (m, 3H), 7.33 (s, 1H), 6.98 (d, J=9.04 Hz, 1H), 6.73-6.80 (m, 2H), 3.92 (m, 3H), 3.89 (m, 6H). ¹³C NMR (101 MHz, DMSO-d₆) δ ppm: 132.9, 123.9, 116.40, 112.3, 106.8, 101.4, 100.0, 99.4, 56.7, 56.4, 56.4. LC/HRMS: calculated for C₁₉H₁₉N₂O₅ [M+H]⁺: 355, found 355.1. mp: 202.3° C.

(2E)-3-(4-hydroxy-3-methoxyphenyl)-1-[4-(trifluoromethoxy)phenyl]prop-2-en-1-one "12a"

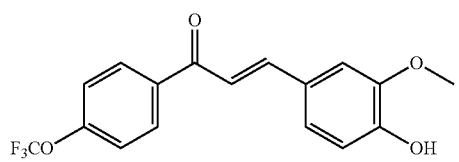

12a

Compound 12a was obtained following procedure A.

Isolated yield: 56%. rt: 5.42 min. ¹H NMR (400 MHz, CDCl₃-d) δ ppm 7.92-7.98 (m, 2H), 7.66 (d, J=15.5 Hz, 1H), 7.18-7.27 (m, 3H), 7.07-7.13 (m, 1H), 7.02 (s, 1H), 6.86 (d, J=8.03 Hz, 1H), 3.84 (br s, 3H). ¹³C NMR (101 MHz, CDCl₃-d) δ ppm 146.0, 130.4, 123.6, 120.4, 119.0, 115.0, 110.2, 56.0.

6-(4-hydroxy-3-methoxyphenyl)-4-[4-(trifluoromethoxy)phenyl]-1,2-dihydropyrimidin-2-one (12)

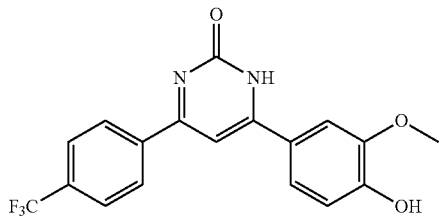

(12)

Compound (12) is obtained from compound 12a following general procedure B.

Isolated yield: 11%. Rt: 3.85 min. ¹H NMR (400 MHz, DMSO-d₆) δ ppm 8.30 (d, J=8.8 Hz, 2H), 7.77-7.65 (m, 2H), 7.58-7.34 (m, 3H), 6.93 (d, J=8.3 Hz, 1H), 3.91 (s, 3H) ¹³C NMR (101 MHz, DMSO-d₆) δ ppm 214.0, 150.1, 130.4, 128.6, 121.6, 116.1, 111.7, 56.8 LC/HRMS: pour C₁₈H₁₄F₃N₂O₄ [M+H]⁺: 379.0, found 379.0. Mp: 281.4° C.

(2E)-1-(4-ethoxyphenyl)-3-(4-hydroxy-3-methoxyphenyl)prop-2-en-1-one "13a"

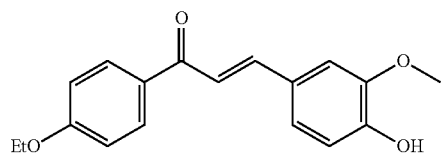

13a

Compound 13a was obtained following procedure A.

Isolated yield: 51%. Rt: 3.37 min. ¹H NMR (400 MHz, CDCl₃-d) δ ppm 8.05-7.82 (m, 2H), 7.65 (br d, J=15.6 Hz, 1H), 7.30 (br d, J=15.6 Hz, 1H), 7.10 (br d, J=7.8 Hz, 1H), 7.02 (br s, 1H), 6.94-6.82 (m, 3H), 6.14 (br s, 1H), 4.11-3.91 (m, 2H), 3.84 (br s, 3H), 1.47-1.25 (m, 3H) ¹³C NMR (101 MHz, CDCl₃-d) δ ppm 144.4, 130.8, 123.2, 119.5, 114.9, 114.3, 110.2, 63.8, 56.0, 14.7.

4-(4-ethoxyphenyl)-6-(4-hydroxy-3-methoxyphenyl)-1,2-dihydropyrimidin-2-one (13)

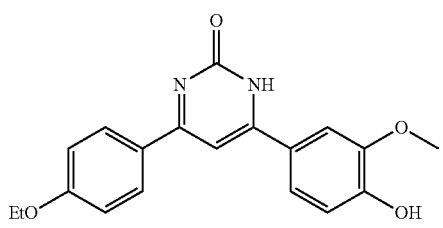

(13)

Compound (13) is obtained from compound 13a following general procedure B.

Isolated yield: 41%. Rt: 3.37 min. ¹H NMR (400 MHz, DMSO-d₆) δ ppm 10.70 (br s, 1H), 8.20 (br d, J=8.8 Hz, 2H), 7.84 (dd, J=8.5, 1.8 Hz, 1H), 7.80-7.72 (m, 1H), 7.56

(s, 1H), 7.17 (br d, J=8.8 Hz, 2H), 7.08 (d, J=8. Hz, 1H), 4.19 (q, J=6.9 Hz, 2H), 3.93 (s, 3H), 1.38 (t, J=6.9 Hz, 3H) $^{13}$C NMR (101 MHz, DMSO-d$_6$) δ ppm 131.6, 124.7, 116.5, 115.5, 112.7, 98.9, 64.4, 56.6, 14.9. LC/HRMS: pour C$_{19}$H$_{19}$N$_2$O$_4$ [M+H]$^+$: 339.0, found 339.1. Mp: 245.0° C.

6-(4-hydroxy-3-methoxyphenyl)-4-(2-methoxyphenyl)-1,2-dihydropyrimidin-2-one (14)

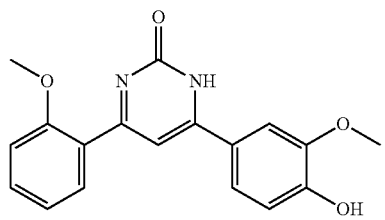

(14)

Compound (14) is obtained following general procedure C.

Isolated yield: 11%. Rt: 3.13 min. $^1$H NMR (400 MHz, DMSO-d$_6$) δ ppm 7.97-7.89 (m, 2H), 7.66-7.49 (m, 5H), 6.92 (d, J=8.28 Hz, 1H), 3.85 (s, 3H), 3.20 (s, 3H), 2.55 (s, 2H). $^{13}$C NMR (101 MHz, DMSO-d$_6$) δ ppm 133.3, 130.7, 129.7, 129.5, 129.0, 128.8, 123.5, 115.8, 113.4, 60.9, 56.1. LC/HRMS: pour C$_{18}$H$_{17}$N$_2$O$_4$ [M+H]$^+$: 324.3, found 324.0. Mp: 261.5° C.

4-[(2E)-3-(4-hydroxy-3-methoxyphenyl)prop-2-enoyl]benzonitrile "15a"

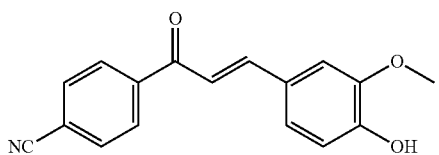

15a

Compound 15a was obtained following procedure A.

Isolated yield: 97%. Rt: 4.49 min. $^1$H NMR (400 MHz, DMSO-d$_6$) δ ppm 9.79 (br s, 1H), 8.33-8.17 (m, 2H), 8.16-7.94 (m, 2H), 7.75 (br s, 2H), 7.54 (br s, 1H), 7.43-7.26 (m, 1H), 6.86 (br d, J=6.78 Hz, 1H), 3.89 (br s, 3H) $^{13}$C NMR (101 MHz, DMSO-d$_6$) δ ppm 146.9, 133.2, 129.4, 129.2, 125.1, 118.8, 116.1, 112.4, 56.3.

4-[6-(4-hydroxy-3-methoxyphenyl)-2-oxo-1,2-dihydropyrimidin-4-yl]benzonitrile (15)

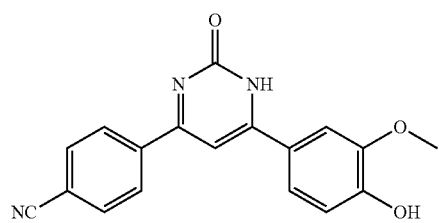

(15)

Compound 15 was obtained from compound 15a following procedure B.

Isolated yield: 76%. Rt: 3.10 min. $^1$H NMR (400 MHz, DMSO-d$_6$) δ ppm 8.35 (d, J=8.5 Hz, 2H), 8.04 (d, J=8.5 Hz, 2H), 7.81-7.68 (m, 2H), 7.62 (s, 1H), 6.94 (d, J=9.0 Hz, 1H), 3.91 (s, 3H) $^{13}$C NMR (101 MHz, DMSO-d$_6$) δ ppm 151.3, 148.4, 133.2, 128.9, 122.4, 118.9, 116.1, 114.1, 111.8, 56.4. LC/HRMS: pour C$_{18}$H$_{14}$N$_3$O$_3$ [M+H]$^+$: 318.0, found 318.0. Mp: 317.4° C.

4-(4-cyclohexylphenyl)-6-(4-hydroxy-3-methoxyphenyl)-1,2-dihydropyrimidin-2-one (16)

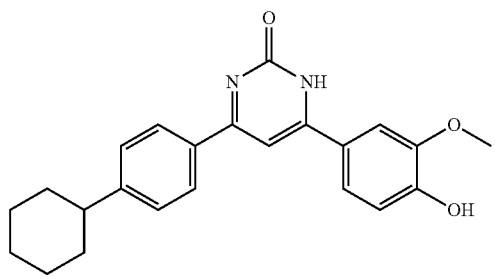

(16)

Compound (16) is obtained following general procedure C.

Isolated yield: 34%. Rt: 4.51 min. $^1$H NMR (400 MHz, DMSO-d$_6$) δ ppm: 11.8 (br s, 1H), 9.8 (br s, 1H), 8.0 (br d, J=7.8 Hz, 2H), 7.73-7.65 (m, 2H), 7.44-7.35 (m, 3H), 6.9 (d, J=8.3 Hz, 1H), 3.9 (s, 3H), 2.6 (br t, J=10.9 Hz, 1H), 1.85-1.77 (m, 4H), 1.7 (br d, J=12.5 Hz, 1H), 1.51-1.23 (m, 5H) $^{13}$C NMR (101 MHz, DMSO-d$_6$) δ ppm: 128.1, 127.6, 121.9, 116.0, 111.6, 56.3, 44.1, 34.2, 26.7. LC/HRMS: pour C$_{23}$H$_{25}$N$_2$O$_3$ [M+H]$^+$: 376.5, found 376.1. Mp: 339.6° C.

4-(4-chlorophenyl)-6-(4-hydroxy-3,5-dimethoxyphenyl)-1,2-dihydropyrimidin-2-one (17)

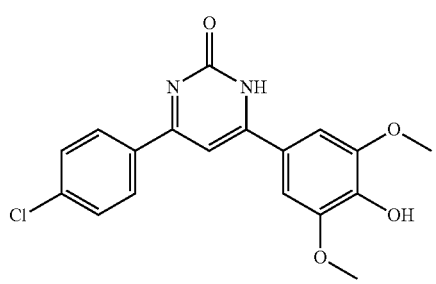

(17)

Compound (17) is obtained following general procedure C.

Isolated yield: 12%. Rt: 3.49 min. $^1$H NMR (400 MHz, DMSO-d$_6$) δ ppm 8.23 (br d, J=8.56 Hz, 1H), 7.63 (d, J=8.56 Hz, 1H), 7.46 (s, 2H), 3.90 (s, 3H), 3.18 (s, 1H). $^{13}$C NMR (101 MHz, DMSO-d$_6$) δ ppm 129.9, 129.3, 105.9, 56.8, 56.7, 49.1. LC/HRMS: pour C$_{18}$H$_{16}$ClN$_2$O$_4$ [M+H]$^+$: 358.8, found 358.1. Mp: 314.4° C.

6-(4-hydroxy-3-methoxyphenyl)-4-[4-(2H-1,2,3,4-tetrazol-5-yl)phenyl]-1,2-dihydropyrimidin-2-one (18)

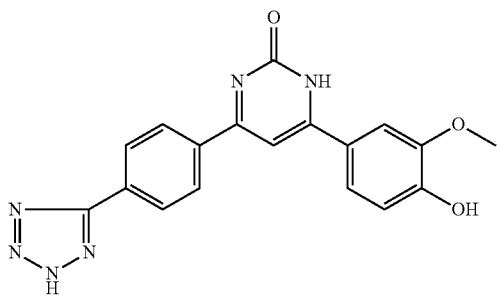

(18)

Compound (18) is obtained following general procedure C.

Isolated yield: 27%. Rt: 2.74 min. $^1$H NMR (400 MHz, DMSO-d$_6$) δ ppm 8.17-8.54 (m, 4H), 7.53-7.87 (m, 3H), 6.94 (br d, J=7.8 Hz, 1H), 3.92 (br s, 3H) $^{13}$C NMR (101 MHz, DMSO-d$_6$) δ ppm 128.90, 127.50, 122.05, 116.06, 111.62, 56.35. LC/HRMS pour C$_{18}$H$_{15}$N$_6$O$_3$ [M+H]$^+$: 362.3, found 363.1. Mp: 328.2° C.

(2E)-3-(4-hydroxy-3-methoxyphenyl)-1-[4-(morpholin-4-yl)phenyl]prop-2-en-1-one "19a"

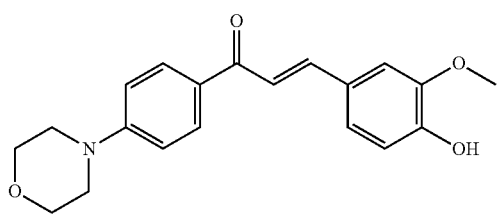

19a

Compound 19a was obtained following procedure A.

Isolated yield: 49%. Rt: 4.24 min. $^1$H NMR (400 MHz, CDCl$_3$-d) δ ppm 8.00 (d, J=9.0 Hz, 2H), 7.73 (d, J=15.6 Hz, 1H), 7.40 (d, J=15.56 Hz, 1H), 7.22 (dd, J=8.2, 1.9 Hz, 1H), 7.12 (d, J=2.0 Hz, 1H), 6.93 (dd, J=11.3, 8.5 Hz, 3H), 5.92 (s, 1H), 3.96 (s, 3H), 3.90-3.85 (m, 4H), 3.36-3.30 (m, 4H).

6-(4-hydroxy-3-methoxyphenyl)-4-[4-(morpholin-4-yl)phenyl]-1,2-dihydropyrimidin-2-one (19)

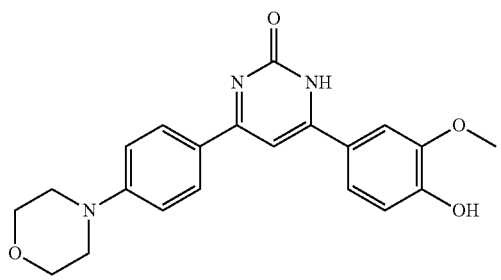

(19)

Compound (19) is obtained from compound 19a following general procedure B.

Isolated yield: 34%; Rt: 3.10 min. $^1$H NMR (400 MHz, DMSO-d$_6$) δ ppm 8.17 (m, J=9.3 Hz, 2H), 7.78 (dd, J=8.5, 2.26 Hz, 1H), 7.70 (d, J=2.26 Hz, 1H), 7.49 (s, 1H), 7.12 (m, J=9.3 Hz, 2H), 7.00 (d, J=8.5 Hz, 1H), 3.92 (s, 3H), 3.77-3.74 (t, 4H, J=4.0 Hz), 3.49-3.43 (t, 4H, J=4.0 Hz). $^{13}$C NMR (101 MHz, DMSO-d$_6$) δ ppm 129.3, 122.0, 114.3, 111.7, 110.3, 95.6, 54.4. LC/HRMS pour C$_{21}$H$_{22}$N$_3$O$_4$ [M+H]$^+$: 379.4, found 379.0.

(E)-4-(3-(4-chlorophenyl)-3-oxoprop-1-en-1-yl)-2-methoxyphenyl diethyl phosphate "20a"

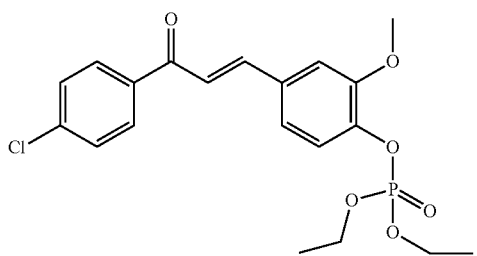

20a

To a solution of POCl$_3$ (5.1 eq., 2.71 g, 1.65 mL, 17.7 mmol) in anhydrous DCM at 0° C., was added anhydrous Et$_3$N (13 eq., 4.56 g, 6.26 mL, 45 mmol), then a solution of (2E)-1-(4-chlorophenyl)-3-(4-hydroxy-3-methoxyphenyl)prop-2-en-1-one (1 eq., 1 g, 3.46 mmol) in 3 ml of anhydrous DCM. The solution was stirred 1 h at 0° C. POCl3 in excess was evaporation. 40 ml of EtOH was added and the solution stirred for 10 min. After evaporation, the product was purified on silica gel (30% EtOAc in n-heptane), followed by recrystallization from EtOAc and heptane to afford the desired product (536 mg, 1.26 mmol, 36%) as a yellow solid.

$^1$H NMR (400 MHz, CDCl$_3$) δ 7.89-7.87 (m, 2H), 7.66 (d, J=15.6 Hz, 1H), 7.42-7.39 (m, 2H), 7.39-7.27 (m, 2H), 7.20-7.10 (m, 2H), 4.21-4.17 (m, 4H), 3.86 (s, 3H), 4.32-4.28 (td, J=7.5 Hz, J=0.8 Hz, 6H); $^{13}$C RMN (101 MHz, CDCl$_3$) δ 144.6, 129.9, 129.0, 121.7, 121.6, 121.5, 121.5, 112.3, 64.8, 64.7, 56.1, 16.1, 16.0; RT: 5.78 min.

4-(6-(4-chlorophenyl)-2-oxo-2,3-dihydropyrimidin-4-yl)-2-methoxyphenyl Ethyl Hydrogen Phosphate "20b"

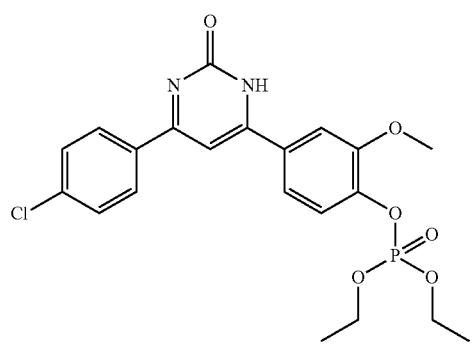

20b

Synthesis was performed following general procedure B, from 4-[(1E)-3-(4-chlorophenyl)-3-oxoprop-1-en-1-yl]-2-methoxyphenyl diethyl phosphate (1 eq., 536 mg, 1.26 mmol). The residue was purified on flash chromatography (5-60% MeCN in water) and evaporated to obtain the desired product (28 mg, 0.03 mmol, 5%) as a yellow solid. $^1$H NMR (400 MHz, DMSO-$d_6$) δ 8.23 (d, J=8.4 Hz, 2H), 7.79 (s, 1H), 7.75 (d, J=8.4 Hz, 1H), 7.65-7.62 (m, 3H), 7.43 (d, J=8.4 Hz, 1H), 4.07-3.99 (q, J=7.2 Hz, 2H) 3.93 (s, 3H), 1.22 (t, J=7.2 Hz, 3H); $^{13}$C RMN (101 MHz, DMSO-$d_6$) δ 129.9, 129.3, 121.1, 120.8, 112.2, 63.0, 56.5, 16.5; MS (ESI-TOF): m/z =437.0 [M+H]$^+$; RT: 3.12 min.

Sodium 4-(6-(4-chlorophenyl)-2-oxo-2,3-dihydropyrimidin-4-yl)-2-methoxyphenyl Phosphate (20)

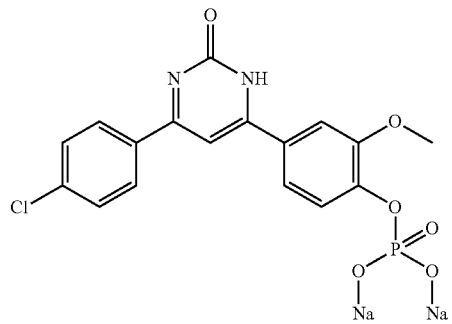

(20)

To a solution of 4-(6-(4-chlorophenyl)-2-oxo-2,3-dihydropyrimidin-4-yl)-2-methoxyphenyl ethyl hydrogen phosphate (1 eq., 28 mg, 0.06 mmol) in 400 μL of DCM, was added bromotrimethylsilane (6.5 eq., 55 μL, 0.42 mmol). The solution was stirred for 3 h at RT. A mixture of Et$_2$O/H$_2$O 10/1 was added. The organic phase was washed with water. The pH of the aqueous phase was basified until pH=8 with NaOH 1M. The reaction mixture was then concentrated under reduced pressure. The residue was purified on flash chromatography (5-60% MeCN in water) and evaporated to obtain the desired product (11 mg, 0.02 mmol, 38%) as a yellow solid. $^1$H NMR (400 MHz, D$_2$O) δ 7.83 (d, J=8.0 Hz, 2H), 7.52-7.46 (m, 5H), 7.21 (s, 1H), 3.89 (s, 3H); $^{13}$C RMN (101 MHz, D$_2$O) δ 129.0, 121.3, 119.9, 111.7, 101.7, 56.2; MS (ESI-TOF): m/z=408.0 [M−H]$^-$; RT: 2.72 min.

(E)-3-(4-hydroxy-3-methoxyphenyl)-1-(4-(piperazin-1-yl)phenyl)prop-2-en-1-one "21a"

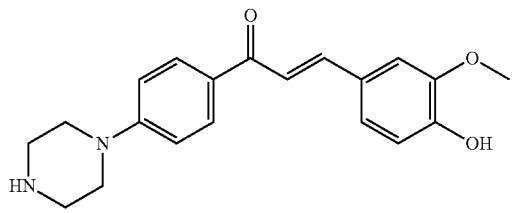

21a

A mixture of 4'-piperazinoacetophenone (0.885 g, 4.33 mmol, 1 equiv) and vanillin (0.659 g, 4.33 mmol, 1 equiv) was stirred in methanol (6.5 mL). An aqueous solution of 40% KOH (4.3 ml) was added. The reaction mixture was stirred overnight at room temperature. The reaction mixture was poured into ice and acidified with HC. The crude was purified by flash chromatography on silica gel column (CH$_2$Cl$_2$/MeOH 10:0 to 90:10 (v/v) in 30 min) to afford a brown solid (1.42 g, 4.19 mmol, 97%).

HPLC Purity=97%, tr=3.04 min; $^1$H NMR (400 MHz, DMSO-$d_6$) δ 9.24 (br s, 2H), 8.08 (d, J=8.8 Hz, 2H), 7.74 (d, J=15.6 Hz, 1H), 7.60 (d, J=15.6 Hz, 1H), 7.48 (s, 1H), 7.26 (d, J=8.2 Hz, 1H), 7.08 (d, J=8.8 Hz, 2H), 6.84 (d, J=8.2 Hz, 1H), 3.87 (s, 3H), 3.55-3.64 (br t, J=5.2 Hz, 4H), 3.22 (br s, 4H); $^{13}$C NMR (101 MHz, DMSO-$d_6$) δ 186.7, 152.8, 149.4, 147.9, 143.4, 130.4, 128.6, 126.5, 123.6, 118.7, 115.6, 113.9, 111.7, 55.8, 43.8, 42.2; MS (ESI$^+$): m/z=339 [M+H]$^+$.

6-(4-hydroxy-3-methoxyphenyl)-4-(4-(piperazin-1-yl)phenyl)pyrimidin-2(1H)-one Hydrochloride (21)

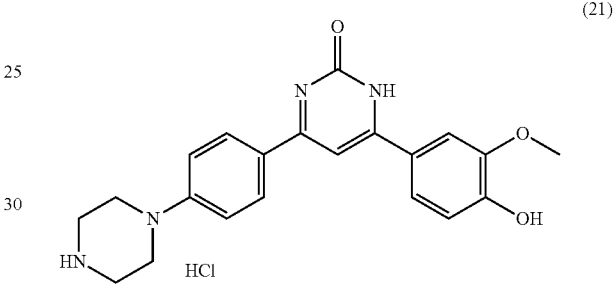

(21)

Compound (21) is obtained from compound 21a according to general procedure B.

Orange solid (22 mg, 0.0581 mmol, 3%). HPLC Purity=95%; tr=2.34 min; mp 117-124° C.; $^1$H NMR (400 MHz, DMSO-$d_6$) δ 9.99 (br s, 1H), 8.83 (br s, 1H), 8.13 (d, J=9.0 Hz, 2H), 7.72-7.65 (m, 2H), 7.36 (br s, 1H), 7.13 (d, J=9.0 Hz, 2H), 6.93 (d, J=8.0 Hz, 1H), 3.90 (s, 3H), 3.59 (br s, 4H), 3.25 (br s, 4H); $^{13}$C NMR (126 MHz, DMSO-$d_6$) δ 157.9, 157.6, 147.8, 129.5, 115.6, 114.5, 111.3, 55.9, 44.1, 42.5; HRMS (ESI-TOF): calcd for C$_{21}$H$_{23}$N$_4$O$_3$ [M+H]$^+$: 379.1770, found 379.1773.

Methyl 4-acetylbenzoate "22a"

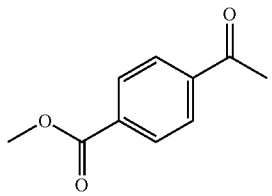

22a

To a stirred solution of 4-acetylbenzoic acid (511 mg, 3.11 mmol, 1 equiv) in methanol (5.1 mL) was added conc. sulfuric acid (0.382 mL, 7.16 mmol, 2.3 equiv) at room temperature, and the mixture was stirred for 4.5 h at 60° C. After being cooled to room temperature, the solvent was removed under vacuum and the residue was extracted with EtOAc. The extract was washed with saturated aqueous NaHCO$_3$ and brine, dried over Na$_2$SO$_4$, and concentrated under reduced pressure to give a white solid (532 mg, 2.99 mmol, 96%).

HPLC Purity=94%; tr=3.70 min; $^1$H NMR (400 MHz, CDCl$_3$) δ 8.14 (d, J=8.0 Hz, 2H), 8.02 (d, J=8.0 Hz, 2H), 3.96 (s, 3H), 2.65 (s, 3H); MS (ESI$^+$): m/z=179 [M+H]$^+$.

Ethyl (E)-4-(3-(4-hydroxy-3-methoxyphenyl)acryloyl)benzoate "22b"

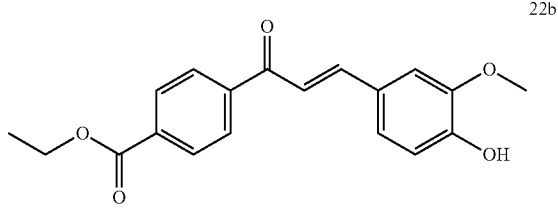 [SMILES: CCOC(=O)c1ccc(C(=O)/C=C/c2ccc(O)c(OC)c2)cc1]

To a solution of methyl 4-acetylbenzoate 22a (0.297 g, 1.67 mmol, 1 equiv) and vanillin (0.254 g, 1.67 mmol, 1 equiv) in EtOH (1.37 mL) was slowly added thionyl chloride (83 µL, 1.14 mmol, 0.7 equiv). The mixture was heated overnight at 75° C. The reaction mixture was concentrated under reduced pressure. The crude product was purified by flash chromatography on silica gel column (hexanes/EtOAc 10:0 to 10:10 (v/v) in 30 min) to afford a yellow solid (119 mg, 0.380 mmol, 22%).

HPLC Purity=83%; tr=5.05 min; $^1$H NMR (400 MHz, CDCl$_3$) δ 8.12-8.22 (d, J=8.6 Hz, 2H), 8.01-8.07 (m, J=8.6 Hz, 2H), 7.76 (d, J=15.8 Hz, 1H), 7.35 (d, J=15.8 Hz, 1H), 7.24 (dd, J=1.4, 8.2 Hz, 1H), 7.14 (d, J=1.4 Hz, 1H), 6.97 (d, J=8.2 Hz, 1H), 4.43 (q, J=7.1 Hz, 2H), 3.98 (s, 3H), 1.43 (t, J=7.1 Hz, 3H); $^{13}$C NMR (101 MHz, CDCl$_3$) δ 189.6, 165.2, 148.4, 146.6, 146.1, 141.9, 133.4, 129.7, 128.2, 126.9, 123.6, 119.7, 114.9, 110.1, 61.4, 56.1, 31.9, 14.3. MS (ESI$^+$): m/z=327 [M+H]$^+$.

Ethyl 4-(6-(4-hydroxy-3-methoxyphenyl)-2-oxo-1,2-dihydropyrimidin-4-yl)benzoate "22c"

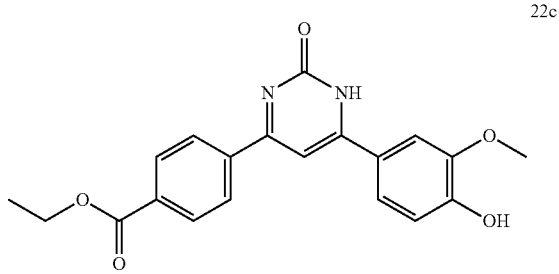 [SMILES: CCOC(=O)c1ccc(-c2cc(-c3ccc(O)c(OC)c3)[nH]c(=O)n2)cc1]

Compound 22c is obtained from compound 22b according to general procedure B.

Brown solid (25 mg, 0.068 mmol, 21%). HPLC Purity=100%; tr=3.55 min; mp 254-258° C.; $^1$H NMR (400 MHz, DMSO-d$_6$) δ 12.0 (br s, 1H), 9.84 (br s, 1H), 8.30 (d, J=7.5 Hz, 2H), 8.09 (d, J=8.5 Hz, 2H), 7.72-7.69 (m, 2H), 7.56 (s, 1H), 6.92 (d, J=8.5 Hz, 1H), 4.36 (q, J=7.0 Hz, 2H), 3.90 (s, 3H), 1.35 (t, J=7.0 Hz, 3H); $^{13}$C NMR (126 MHz, DMSO-d$_6$) 165.8, 150.9, 148.3, 132.4, 129.9, 128.4, 122.1, 116.1, 111.6, 61.5, 56.3, 14.6; HRMS (ESI-TOF): calcd for C$_{20}$H$_{19}$N$_2$O$_5$ [M+H]$^+$: 367.1294, found 367.1287.

4-(6-(4-hydroxy-3-methoxyphenyl)-2-oxo-1,2-dihydropyrimidin-4-yl)benzoic Acid (22)

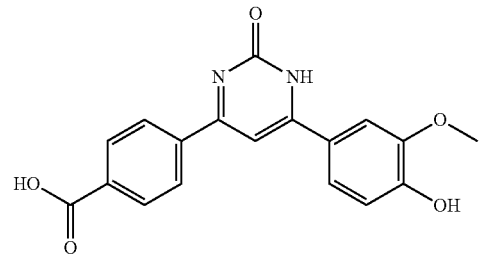

To a solution of ethyl 4-(6-(4-hydroxy-3-methoxyphenyl)-2-oxo-1,2-dihydropyrimidin-4-yl)benzoate 22c (20.7 mg, 56.5 µmol, 1 equiv) in EtOH (140 µL) and THF (279 µL) was added a 2M aq. NaOH solution (283 µL, 565 µmol, 10 equiv). The reaction mixture was stirred overnight at room temperature. An aq. 1N HCl solution (0.6 mL) was added to the reaction mixture and the precipitate was filtered and lyophilized to afford an orange solid (22 mg, 66.7 µmol, 100%).

HPLC Purity=100%; tr=2.68 min; mp 320-325° C.; $^1$H NMR (500 MHz, DMSO-d$_6$) δ 9.94 (br s, 1H), 8.27 (d, J=8.5 Hz, 2H), 8.08 (d, J=8.5 Hz, 2H), 7.73-7.72 (m, 2H), 7.57 (br s, 1H), 6.94 (d, J=8.5 Hz, 1H), 3.90 (s, 3H); $^{13}$C NMR (101 MHz, DMSO-d$_6$) δ 166.7, 163.6, 151.6, 148.0, 137.9, 133.5, 129.6, 128.2, 123.2, 122.6, 115.8, 111.6, 56.0; HRMS (ESI-TOF): calcd for C$_{18}$H$_{15}$N$_2$O$_5$ [M+H]$^+$: 339.0981, found 339.0972.

2-azidoethyl 4-methylbenzenesulfonate "23a"

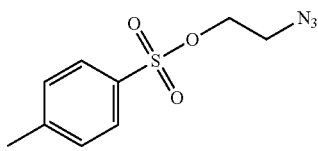

Under argon atmosphere, anhydrous pyridine (3.38 mL, 41.8 mmol, 2 equiv) was added to a solution of 2-azidoethan-1-ol (1.82 g, 20.9 mmol, 1 equiv) in CH$_2$Cl$_2$ (10 mL). At 0° C., tosyl chloride (4.38 g, 23 mmol, 1.1 equiv) in CH$_2$Cl$_2$ (10.4 mL) was added to the reaction mixture.

The reaction mixture was allowed to heat to room temperature and was stirred overnight. The reaction mixture was diluted with CH$_2$Cl$_2$ and extracted with an aq. 1N HCl solution. The organic phase was washed with water and brine, dried over Na$_2$SO$_4$ and concentrated under reduced pressure (3.48 g). The crude product was purified by flash chromatography on a 25 g silica gel column (hexanes/EtOAc 75:25 to 0:10 (v/v) in 30 min) to afford a colorless liquid (3.03 g, 12.6 mmol, 60%).

HPLC Purity=87%; tr=4.64 min; $^1$H NMR (400 MHz, CDCl$_3$) δ 7.83 (d, J=8.0 Hz, 2H), 7.38 (d, J=8.0 Hz, 2H), 4.15-4.20 (t, J=5.2 Hz, 2H), 3.49 (t, J=5.2 Hz, 2H). MS (ESI$^+$): m/z=264 [M+Na]$^+$.

3-(2-azidoethoxy)-4-hydroxybenzaldehyde "23b"

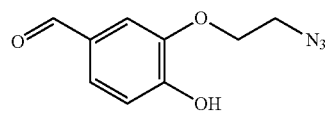

Under argon atmosphere, to a suspension of NaH (60% in oil, 0.98 g, 24.5 mmol, 2.2 equiv) in anhydrous DMSO (40 mL) at 20° C. was added dropwise a solution of 3,4-dihydroxybenzaldehyde (1.85 g, 13.4 mmol, 1.2 equiv) in anhydrous DMSO (6.6 mL). The reaction mixture was stirred for 1 h. A solution of 2-azidoethyl 4-methylbenzenesulfonate (23a) (2.69 g, 11.1 mmol, 1 equiv) in anhydrous DMSO (6.6 mL) was added dropwise to the reaction mixture. The reaction mixture was stirred overnight at room temperature. The reaction mixture was poured in a mixture of ice and water and extracted four times with EtOAc. The collected organic phases were dried over $Na_2SO_4$ and concentrated under reduced pressure. The crude product was purified by flash chromatography on a 25 g silica gel column (hexanes/EtOAc 10:0 to 10:10 (v/v) in 30 min) to afford a colorless oil (270 mg, 1.3 mmol, 12%).

HPLC Purity=98%; tr=3.24 min; $^1$H NMR (400 MHz, CDCl$_3$) δ 9.84 (s, 1H), 7.48 (dd, J=1.7, 8.1 Hz, 1H), 7.44 (d, J=1.7 Hz, 1H), 7.09 (d, J=8.1 Hz, 1H), 6.27 (br s, 1H), 4.33 (d, J=4.8 Hz, 2H), 3.72 (d, J=4.8 Hz, 2H); $^{13}$C NMR (101 MHz, CDCl$_3$) δ 190.6, 151.9, 145.8, 129.9, 128.2, 115.2, 110.4, 68.3, 50.1; MS (ESI$^+$): m/z=208 [M+H]$^+$.

3-(2-azidoethoxy)-4-(methoxymethoxy)benzaldehyde "23c"

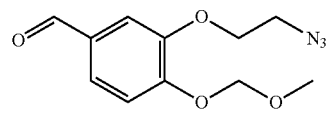

Under Ar, to a solution of 3-(2-azidoethoxy)-4-hydroxybenzaldehyde (23b) (265 mg, 1.28 mmol, 1 equiv) in acetone (4.3 mL) was added K$_2$CO$_3$ (530 mg, 3.84 mmol, 3 equiv). The reaction mixture was vigorously stirred for 5 min. Chloro(methoxy)methane (0.136 mL, 1.79 mmol, 1.4 equiv) was added dropwise to the reaction mixture. The reaction mixture was stirred overnight at room temperature. The reaction mixture was diluted with EtOAc and filtered. The filtrate was concentrated under reduced pressure. The crude product was purified by flash chromatography on silica gel column (hexanes/EtOAc 10:0 to 10:10 (v/v) in 30 min) to afford a colorless oil (237 mg, 0.943 mmol, 74%).

HPLC Purity=98%; tr=4.07 min; $^1$H NMR (400 MHz, CDCl$_3$) δ 9.69 (s, 1H), 7.30-7.26 (m, 2H), 7.10-7.08 (m, 1H), 5.13 (s, 2H), 4.09 (t, J=4.8 Hz, 2H), 3.5 (t, J=4.8 Hz, 2H), 3.34 (s, 3H); $^{13}$C NMR (101 MHz, CDCl$_3$) δ 190.7, 152.5, 149.0, 131.0, 127.0, 115.4, 111.6, 95.0, 68.1, 56.5, 50.1; MS (ESI$^+$): m/z=274 [M+Na]$^+$.

6-(3-(2-aminoethoxy)-4-hydroxyphenyl)-4-(4-chlorophenyl)pyrimidin-2(1H)-one Hydrochloride (23)

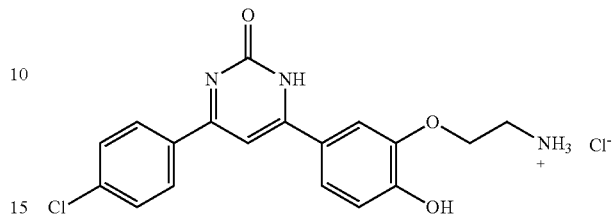

Compound (23) is obtained from compound (23c) according to general procedure C.

Orange solid (8 mg, 0.0224 mmol, 2%). HPLC Purity=100%; tr=2.95 min; mp 272-276° C.; $^1$H NMR (400 MHz, DMSO-d$_6$) δ 10.16 (br s, 1H), 8.54 (br s, 3H), 8.17 (d, J=8.2 Hz, 2H), 7.90 (d, J=8.2 Hz, 1H), 7.85 (s, 1H), 7.70 (d, J=8.2 Hz, 2H), 7.64 (s, 1H), 7.04 (d, J=8.2 Hz, 1H), 4.35 (br s, 2H), 3.29 (br s, 2H); $^{13}$C NMR (101 MHz, DMSO-d$_6$) δ 163.5, 162.9, 152.4, 146.2, 137.9, 130.7, 130.4, 129.1, 127.4, 124.6, 116.3, 112.6, 99.8, 65.2, 38.3; HRMS (ESI-TOF): calcd for $C_{18}H_{17}ClN_3O_3$ [M+H]$^+$: 358.0958, found 358.0948.

1-(4-(4-methylpiperazin-1-yl)phenyl)ethan-1-one "24a"

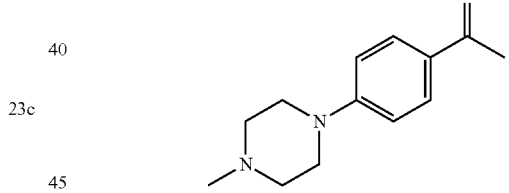

To a solution of 4'-fluoroacetophenone (5.51 mL, 45.1 mmol, 1 equiv) in DMSO (22.5 mL) was added at room temperature 1-methylpiperazine (5 mL, 45.1 mmol, 1 equiv). The reaction mixture was stirred at 100° C. for 16 h. The reaction mixture was cooled down to room temperature and quenched with a saturated aq. Na$_2$CO$_3$ solution (10 mL). The aqueous phase was extracted with EtOAc (3×20 mL) and the collected organic layers were dried over Na$_2$SO$_4$, filtered and concentrated under reduced pressure. The crude product was purified by flash chromatography on a 80 g silica gel column (CH$_2$Cl$_2$/MeOH 1:0 to 9:1 (v/v) in 60 min) to afford a pale yellow solid (6.72 g, 30.8 mmol, 68%).

HPLC Purity=98%; tr=1.93 min; $^1$H NMR (400 MHz, CDCl$_3$) δ 7.88 (d, J=9.2 Hz, 2H), 6.87 (d, J=9.2 Hz, 2H), 3.50-3.41 (m, 4H), 2.65-2.55 (m, 4H), 2.52 (s, 3H), 2.45 (s, 3H); $^{13}$C NMR (101 MHz, CDCl$_3$) δ 196.5, 153.8, 130.4, 128.1, 113.7, 54.4, 46.9, 45.6, 26.1; MS (ESI$^+$): m/z=219 [M+H]$^+$.

6-(4-hydroxy-3-methoxyphenyl)-4-(4-(4-methylpiperazin-1-yl)phenyl)pyrimidin-2(1H)-one Hydrochloride (24)

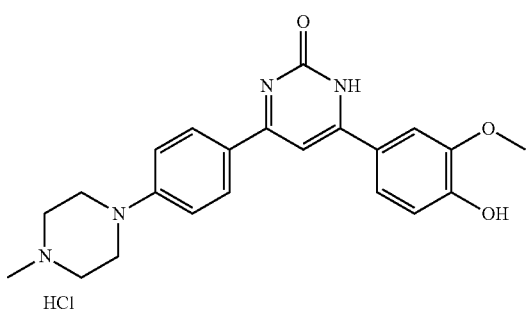

Compound (24) is obtained from compound 24a and vanillin according to general procedure C.

White solid (24 mg, 0.061 mmol, 3%). HPLC Purity=95%; tr=2.34 min; mp 300-303° C.; $^1$H NMR (400 MHz, DMSO-$d_6$) δ 11.6 (br s, 1H), 9.76 (br s, 1H), 8.03 (br s, 2H), 7.66 (br s, 2H), 7.27 (br s, 1H), 7.03 (br d, J=6.0 Hz, 2H), 6.90 (br s, 1H), 3.89 (s, 3H), 3.33 (br s, $H_2O$+4H), 2.31-2.25 (m, DMSO-$d_6$+4H), 2.23 (s, 3H). $^{13}$C NMR (126 MHz, DMSO-$d_6$) δ 159.5, 153.0, 150.1, 147.7, 128.8, 121.3, 115.5, 113.9, 111.0, 55.8, 54.3, 46.8, 45.7; HRMS (ESI-TOF): calcd for $C_{22}H_{25}N_4O_3$ [M+H]$^+$: 393.1927, found 393.1912.

3-hydroxy-4-(methoxymethoxy)benzaldehyde "25a"

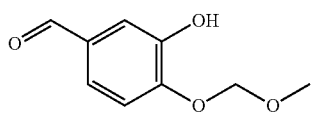

A suspension of 3,4-dihydroxybenzaldehyde (2.12 g, 15.3 mmol, 1 equiv) and $K_2CO_3$ (6.36 g, 46 mmol, , 3 equiv) in anhydrous $CH_3CN$ (23 mL) was vigorously stirred for 30 min at room temperature. Chloro(methoxy)methane (1.4 mL, 18.4 mmol, 1.2 equiv) was added in one portion. The reaction mixture was stirred for 2 h. Water was added and all phenols were extracted twice with 10% aq. NaOH. The combined aqueous layers were washed three times with EtOAc. The combined organic layers were extracted with 10% aq. NaOH. The combined aqueous layers were acidified with 2N aq. HCl to pH 9. The product was extracted three times with EtOAc. The combined organic layers were washed with a saturated aq. $Na_2CO_3$ solution, dried over $Na_2SO_4$, filtered and concentrated under reduced pressure to afford a brown oil (0.928 g, 5.09 mmol, 33%).

$^1$H NMR (400 MHz, CDCl$_3$) δ 9.87 (s, 1H), 7.47 (d, J=2.0 Hz, 1H), 7.41 (dd, J=8.0 and 2.0 Hz, 1H), 7.23 (d, J=8.0 Hz, 1H), 5.33 (s, 2H), 3.54 (s, 3H); $^{13}$C NMR (101 MHz, CDCl$_3$) δ 191.1, 149.4, 146.6, 131.7, 124.1, 115.0, 114.3, 95.4, 56.7.

4-(methoxymethoxy)-3-(2-morpholinoethoxy)benzaldehyde "25b"

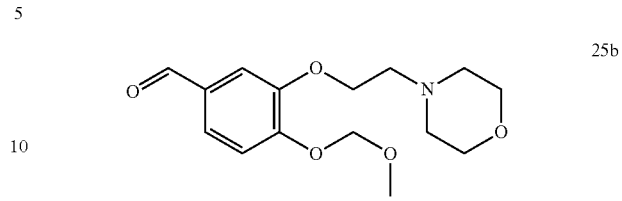

To a stirred solution of 3-hydroxy-4-(methoxymethoxy) benzaldehyde (compound 25a) (0.903 g, 4.96 mmol, 1 equiv) in acetone (19.8 mL) were added $K_2CO_3$ (2.19 g, 15.9 mmol, 3.2 equiv) and 4-(2-chloroethyl)morpholine hydrochloride (2.77 g, 14.9 mmol, 3 equiv). The resulting mixture was refluxed for 16 h. The reaction mixture was cooled down to room temperature and was filtered through celite. The filtrate was removed under reduced pressure. The residue was purified by flash chromatography on silica gel column (hexane/EtOAc 10:0 to 10:10 (v/v) in 30 min and $CH_2Cl_2$/MeOH 80:20) to afford an orange oil (1.02 g, 3.45 mmol, 70%).

HPLC Purity=90%; tr=2.37 min; $^1$H NMR (400 MHz, CDCl$_3$) δ 9.87 (s, 1H), 7.41-7.52 (m, 2H), 7.22-7.26 (m, 1H), 5.30 (s, 2H), 4.42 (br s, 2H), 3.91 (br s, 4H), 3.52 (s, 3H), 3.12 (br s, 2H), 2.93 (br s, 4H); $^{13}$C NMR (101 MHz, CDCl$_3$) δ 190.6, 152.4, 131.1, 126.9, 115.2, 95.0, 65.7, 56.9, 56.6, 53.5. MS (ESI$^+$): m/z=296 [M+H]$^+$.

4-(4-chlorophenyl)-6-(4-(methoxymethoxy)-3-(2-morpholinoethoxy)phenyl)pyrimidin-2(1H)-one "25c"

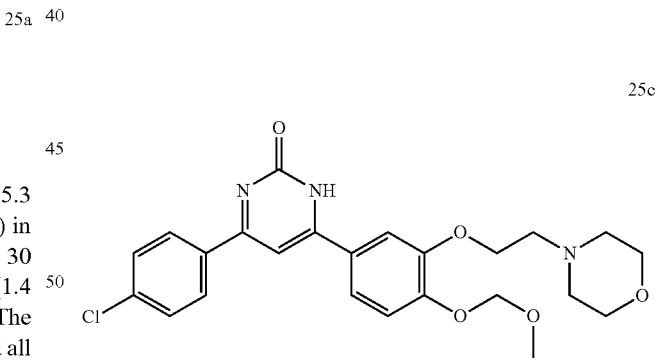

Compound 25c is obtained from compound 25b according to general procedure C.

Pale yellow solid (19 mg, 0.0403 mmol, 4%). $^1$H NMR (400 MHz, DMSO-$d_6$) δ 11.97 (br s, 1H), 8.21 (d, J=8.4 Hz, 2H), 7.83-7.68 (m, 2H), 7.62 (d, J=8.4 Hz, 2H), 7.55-7.53 (m, 1H), 7.21 (d, J=9.2 Hz, 2H), 5.28 (s, 2H), 4.24 (t, J=5.8 Hz, 2H), 3.58 (t, J=4.8 Hz, 4H), 3.42 (s, 3H), 2.75 (d, J=5.8 Hz, 2H), 2.50-2.53 (m, DMSO-$d_{6+4}$H); $^{13}$C NMR (101 MHz, DMSO-$d_6$) δ 159.7, 149.5, 137.2, 136.8, 129.9, 129.3, 121.5, 117.0, 113.0, 95.2, 67.0, 66.7, 57.5, 56.3, 54.1. MS (ESI$^+$): m/z=472 [M+H]$^+$.

4-(4-chlorophenyl)-6-(4-hydroxy-3-(2-morpholinoethoxy)phenyl)pyrimidin-2(1H)-one Hydrochloride (25)

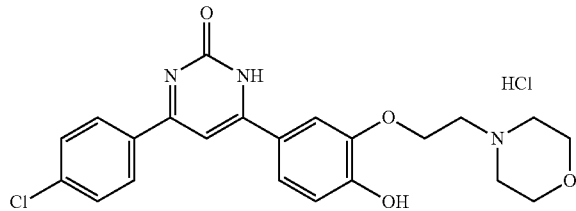

In a microwave vessel was added 4-(4-chlorophenyl)-6-(4-(methoxymethoxy)-3-(2-morpholinoethoxy)phenyl)pyrimidin-2(1H)-one (compound 25c) (17 mg, 0.036 mmol, 1 equiv) in THF (5 µL) and H$_2$O (40 µL). 6N HCl (99 µL, 0.594 mmol, 16.5 equiv) was added. The reaction mixture was stirred overnight at 80° C. The reaction mixture was diluted with a mixture of CH$_2$Cl$_2$/EtOH 9:1 (v/v) and the solid was filtered to afford a yellow solid (11 mg, 0.0257 mmol, 71%).

HPLC Purity=98%; tr=3.09 min; mp 326-330° C.; $^1$H NMR (400 MHz, TFA-di) δ 8.08 (s, 1H), 7.92 (d, J=7.6 Hz, 2H), 7.84 (d, J=8.7 Hz, 1H), 7.74 (br s, 1H), 7.63 (d, J=7.6 Hz, 2H), 7.58 (s, 1H), 7.23 (d, J=8.7 Hz, 1H), 4.66 (br s, 2H), 4.35-4.13 (m, 4H), 4.00-3.74 (m, 4H), 3.43 (br s, 2H); $^{13}$C NMR (126 MHz, TFA-di) δ 167.8, 132.5, 131.8, 129.0, 119.6, 114.2, 102.5, 65.3, 63.6, 57.9, 54.3; HRMS (ESI-TOF): calcd for C$_{22}$H$_{23}$ClN$_3$O$_4$ [M+H]$^+$: 428.1377, found 428.1354.

N-{4-[(1E)-3-(4-chlorophenyl)-3-oxoprop-1-en-1-yl]-2-methoxyphenyl}acetamide "26a"

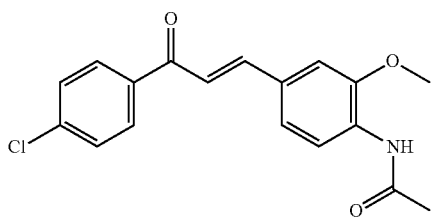

Compound 26a was obtained following procedure A.

Isolated yield: 25%. Rt: 5.23 min. $^1$H NMR (400 MHz, CDCl$_3$-d) δ ppm 8.64-8.56 (m, 1H), 8.17-8.01 (m, 3H), 7.9 (dd, J=15.5, 3.2 Hz, 1H), 7.67-7.51 (m, 3H), 7.49-7.40 (m, 1H), 7.3 (s, 1H), 4.1 (s, 3H), 2.4 (s, 2H).

N-{4-[6-(4-chlorophenyl)-2-oxo-2,3-dihydropyrimidin-4-yl]-2-methoxyphenyl}acetamide (26)

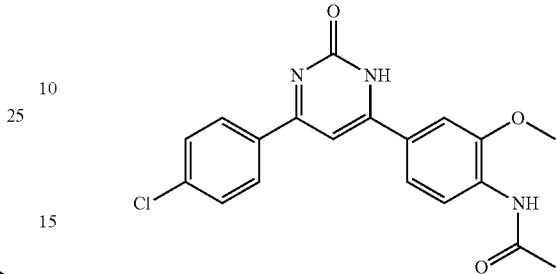

Compound (26) is obtained from compound 26a following general procedure B.

Isolated yield: 5%. Rt: 3.70 min. $^1$H NMR (400 MHz, DMSO-d$_6$) δ ppm 9.4 (s, 1H), 8.2 (br d, J=7.5 Hz, 3H), 7.8 (br s, 2H), 7.6 (br d, J=8.8 Hz, 3H), 5.8 (s, 1H), 4.0 (s, 3H), 2.2 (s, 3H). $^{13}$C NMR (101 MHz, DMSO-d$_6$) δ ppm 169.5, 149.4, 136.8, 129.9, 129.3, 121.1, 120.9, 110.2, 56.6, 24.6. LC/HRMS pour C$_9$H$_{17}$ClN$_3$O$_3$ [M+H]$^+$: 369.8, found 370.0. Mp: 275.1° C.

Methyl 2-methoxy-4-methylbenzoate "27a"

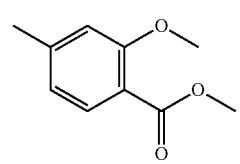

To a solution of 4-methylsalicylic acid (2.93 g, 19.1 mmol, 1 equiv) in acetone (34.8 mL) was added finely ground K$_2$CO$_3$ (7.9 g, 57.2 mmol, 3 equiv) and Me$_2$SO$_4$ (5.42 mL, 57.2 mmol, 3 equiv). The solution was stirred at rt for 18 h and under reflux for 1 h. The reaction mixture was filtered and concentrated under reduced pressure. The crude residue was dissolved in EtOAc (100 mL) and Et$_3$N (2.65 mL, 19.1 mmol, 1 equiv) was added. The reaction mixture was stirred at rt for 30 min. The reaction mixture was successively washed with water, 2N HCl, and brine. The organic phase was dried over Na$_2$SO$_4$, filtered and concentrated under reduced pressure. The crude product was purified by flash chromatography on silica gel column (hexane/EtOAc 10:0 to 10:10 (v/v) in 30 min) to afford a colorless liquid (3.37 g, 18.7 mmol, 98%).

HPLC Purity=99%; tr=4.02 min; $^1$H NMR (400 MHz, CDCl$_3$) δ 7.73 (d, J=8.4 Hz, 1H), 6.80-6.78 (m, 2H), 3.90 (s, 3H), 3.87 (s, 3H), 2.39 (s, 3H); $^{13}$C NMR (101 MHz, CDCl$_3$) δ 166.6, 159.3, 144.6, 131.8, 120.9, 116.9, 112.8, 55.9, 51.8, 21.9; MS (ESI$^+$): m/z=203 [M+Na]$^+$.

73

Methyl 4-(dibromomethyl)-2-methoxybenzoate "27b"

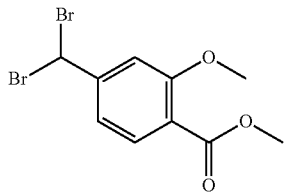

To a solution of methyl 2-methoxy-4-methylbenzoate (compound 27a) (3.37 g, 18.7 mmol, 1 equiv) in CCl$_4$ (187 mL) was added NBS (7.32 g, 41.1 mmol, 2.2 equiv) and benzoyl peroxide (0.181 g, 0.748 mmol, 0.04 equiv). The reaction mixture was refluxed for 5 h. The reaction mixture was cooled down to rt and filtered. The filtrate was collected, washed with water and twice with a saturated aq. Na$_2$S2O3 solution. The combined organic layers were dried over Na$_2$SO$_4$, filtered and concentrated under reduced pressure. The crude product was purified by flash chromatography on a 80 g silica gel column (heptane/CH$_2$Cl$_2$ 25:75 to 0:10 (v/v) in 45 min) to afford a colorless oil (5.2 g, 15.4 mmol, 82%). MS (ESI$^+$): m/z=339 [M+H]$^+$.

Methyl 4-formyl-2-methoxybenzoate "27c"

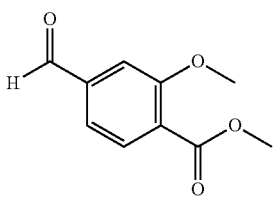

Methyl 4-(dibromomethyl)-2-methoxybenzoate (compound 27b) (3.84 g, 11.4 mmol, 1 equiv) was dissolved in acetone (27 mL) and H$_2$O (6.1 mL). Silver nitrate (4.52 g, 26.6 mmol, 2 equiv) was added. The flask was covered with aluminum foil and the reaction mixture was stirred at rt for 3 h. The reaction mixture was filtered through celite, diluted with EtOAc and a saturated aq. NaHCO$_3$ solution. The reaction mixture was extracted twice with EtOAc. The collected organic layers were washed with water and brine, dried over Na$_2$SO$_4$, filtered and concentrated under reduced pressure. The crude product was purified by flash chromatography on silica gel column (hexanes/EtOAc 10:0 to 10:10 (v/v) in 30 min) to afford a colorless liquid (0.70 g, 3.61 mmol, 32%).

HPLC Purity=95%; tr=3.30 min; $^1$H NMR (400 MHz, CDCl$_3$) δ 10.04 (s, 1H), 7.91 (d, J=8.03 Hz, 1H), 7.49-7.48 (m, 2H), 3.98 (s, 3H), 3.94 (s, 3H); $^{13}$C NMR (101 MHz, CDCl$_3$) δ 191.4, 166.0, 159.2, 139.8, 131.9, 125.8, 122.7, 110.7, 56.3, 52.5; MS (ESI$^+$): m/z=195 [M+H]$^+$.

74

Methyl (E)-4-(3-(4-chlorophenyl)-3-oxoprop-1-en-1-yl)-2-methoxybenzoate "27d"

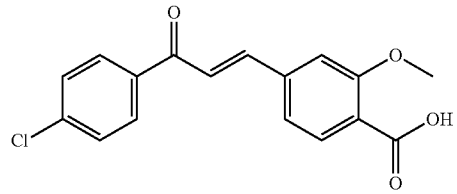

A mixture of 4'-chloroacetophenone (1.18 mL, 9.09 mmol, 1 equiv) and methyl 4-formyl-2-methoxybenzoate (compound 27c) (1.77 g, 9.09 mmol, 1 equiv) was stirred in methanol (47 mL). An aqueous solution of 8% KOH (1.1 ml) was added. The reaction mixture was stirred overnight at room temperature. The reaction mixture was poured into ice and acidified with HCl. The precipitate was filtered to afford a white solid which was purified by flash chromatography on silica gel column (hexanes/EtOAc 10:0 to 0:10 (v/v) in 30 min) to afford a white solid (0.367 g, 1.16 mmol, 13%).

HPLC Purity=100%; tr=5.01 min; $^1$H NMR (400 MHz, DMSO-d$_6$) δ 12.79 (br s, 1H), 8.20 (d, J=8.5 Hz, 2H), 8.03 (d, J=15.6 Hz, 1H), 7.76 (d, J=15.6 Hz, 1H), 7.69-7.63 (m, 4H), 7.52 (d, J=7.9 Hz, 1H), 3.91 (s, 3H); $^{13}$C NMR (101 MHz, DMSO-d$_6$) δ 188.6, 167.4, 158.8, 144.0, 139.4, 138.8, 136.5, 131.4, 131.0, 129.4, 124.1, 123.5, 121.3, 113.0, 56.6; MS (ESI$^+$): m/z=317 [M+H]$^+$.

4-(6-(4-chlorophenyl)-2-oxo-2,3-dihydropyrimidin-4-yl)-2-methoxybenzoic Acid (27)

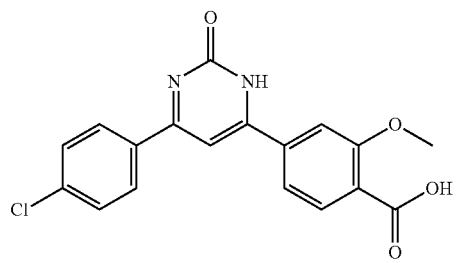

Compound (27) is obtained from compound 27d according general procedure B.

White solid (5 mg, 0.014 mmol, 2%). HPLC Purity=96%; tr=3.66 min; mp 257-261° C.; $^1$H NMR (500 MHz, DMSO-d$_6$) δ 8.17 (d, J=8.8 Hz, 2H), 7.62 (d, J=1.3 Hz, 1H), 7.55 (dd, J=1.3, 7.8 Hz, 1H), 7.48 (d, J=8.8 Hz, 2H), 7.23 (d, J=7.8 Hz, 1H), 7.13 (s, 1H), 3.81 (s, 3H); $^{13}$C NMR (126 MHz, DMSO-d$_6$) 170.6, 163.5, 155.5, 138.3, 135.5, 133.7, 128.5, 128.1, 127.6, 118.4, 109.8, 95.9, 55.4; HRMS (ESI-TOF): calcd for C$_{18}$H$_{14}$ClN$_2$O$_4$ [M+H]$^+$: 357.0642, found 357.0634.

4-(furan-2-yl)-6-(4-hydroxy-3-methoxyphenyl)pyrimidin-2(1H)-one (28)

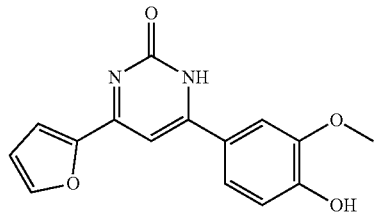
(28)

Synthesis was performed following general procedure C from 2-acetylfuran (0.48 mmol, 0.06 ml, 1 equiv). Hot EtOH was added to the reaction mixture and filtered to obtain the desired product as a yellow solid (36 mg, 0.12 mmol, 26%). $^1$H NMR (400 MHz, DMSO-$d_6$) δ 8.00-8.10 (m, 1H), 7.76-7.50 (m, 3H), 7.21 (br s, 1H), 6.91 (d, J=8.3 Hz, 1H), 6.77 (dd, J=3.5, 1.8 Hz, 1H), 3.89 (s, 3H); $^{13}$C NMR (101 MHz, DMSO-$d_6$) δ 147.1, 121.7, 116.1, 114.7, 113.4, 111.4, 56.3.; MS (ESI-TOF): m/z=285.0 [M+H]$^+$; RT: 2.50 min; mp: 143.5-146.2° C.

1-(3-methoxy-4-(methoxymethoxy)phenyl)ethanone "29a"

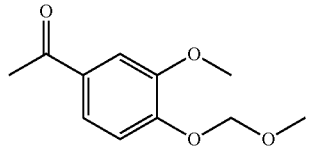
29a

To a solution of 4-hydroxy-3-methoxyacetophenone (2 g, 12 mmol) in anhydrous MeCN (2 mL), were added $K_2CO_3$ (5 g, 36 mmol) and methoxymethyl chloride (1.83 mL, 24 mmol). The mixture was stirred overnight at rt. After removal of the solvent under reduced pressure, water was added to the residue and the aqueous layer was extracted 3 times with EtOAc. The combined organic layers were dried over anhydrous $Na_2SO_4$, filtered and concentrated to affording 2.4 g (96% yield) of a clear oil.

$^1$H NMR (400 MHz, CDCl$_3$) δ 7.55-7.52 (m, 2H), 7.18 (dd, 1H, J=8.1, 2.5 Hz), 5.31 (s, 2H), 3.94 (s, 3H), 3.51 (s, 3H), 2.57 (s, 3H). $^{13}$C NMR (100 MHz, CDCl$_3$) δ 196.8, 150.8, 149.6, 131.7, 123.0, 114.7, 114.5, 110.6, 95.2, 95.1, 56.4, 56.0, 26.3.

1-(3-methoxy-4-(methoxymethoxy)phenyl)-3-(pyridin-3-yl)propane-1,3-dione "29b"

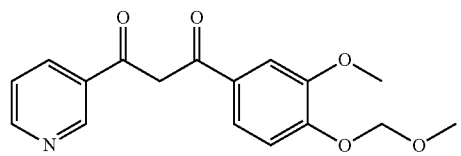
29b

NaH (60% w/w in mineral oil, 162 mg, 6.75 mmol) was suspended in anhydrous THF (5 mL) and cooled to 0° C., then methyl 1-(3-methoxy-4-(methoxymethoxy)phenyl) ethanone (474 mg, 2.25 mmol) in THF (1 mL) was added dropwise. The mixture was stirred during 45 min at 0° C. A solution of methyl niconate (340 mg, 2.48 mmol) in THF (1 mL) was then added. The mixture was stirred overnight at rt. The reaction was quenched by citric acid solution in water (10% w/w) and the mixture was extracted with EtOAc. The combined organic layers were washed twice with water, once with brine then dried over anhydrous $Na_2SO_4$. After evaporation of the solvent, the residue was purified by flash chromatography on silica gel eluting with 80% EtOAc in n-heptane+0.1% Et$_3$N, affording 223 mg (31% yield) of a yellow oil. $^1$H NMR (400 MHz, CDCl$_3$) δ 9.17 (s, 1H), 8.75 (d, H, J=4.8 Hz), 8.26-8.24 (m, 1H), 7.58-7.56 (m, 2H), 7.44 (dd, 1H, J=7.4, 4.5 Hz), 7.23 (d, 1H, J=8.2 Hz), 6.80 (s, 1H), 5.23 (s, 2H), 3.98 (s, 3H), 3.52 (s, 3H). $^{13}$C NMR (100 MHz, CDCl$_3$) δ 187.2, 181.2, 152.6, 150.9, 149.9, 148.3, 134.6, 131.3, 129.5, 123.7, 121.5, 115.1, 110.5, 95.5, 93.2, 56.6, 56.2; MS (ESI-TOF): m/z=316.1 [M+H]$^+$; RT: 3.69 min.

6-(4-hydroxy-3-methoxyphenyl)-4-(pyridin-3-yl)pyrimidin-2(1H)-one (29)

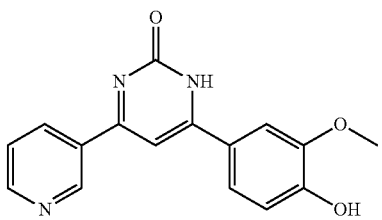
(29)

Synthesis was performed following general procedure B (at 120° C. overnight), from 1-(3-methoxy-4-(methoxymethoxy)phenyl)-3-(pyridin-3-yl)propane-1,3-dione (100 mg, 0.32 mmol). The residue was purified on flash chromatography (5-50% MeCN in water) and evaporated to obtain the desired product (25 mg, 0.085 mmol, 26%) as a yellow solid.

$^1$H NMR (400 MHz, (CD3)$_2$SO) 9.36 (s, 1H), 8.81 (d, 1H, J=3.2 Hz), 8.58 (d, 1H, J=8.4 Hz), 7.75-7.73 (m, 2H), 7.68 (dd, 1H, J=7.5, 4.6 Hz), 7.63 (s, 1H), 6.94 (d, 1H, J=8.8 Hz), 3.91 (s, 3H). $^{13}$C NMR (100 MHz, (CD3)$_2$SO) δ 163.6, 163.2, 151.2, 151.0, 148.0, 147.9, 136.1, 131.1, 131.0, 124.1, 122.1, 115.6, 111.3, 99.8, 55.9; HRMS (ES$^+$) m/z for $C_{16}H_{13}N_3O_3$ calc 295.09569, found 296.09525; RT: 2.13 min; mp: 153-155° C.

6-(4-hydroxy-3-methoxyphenyl)-4-(pyridin-3-yl)pyrimidin-2(1H)-one "30a"

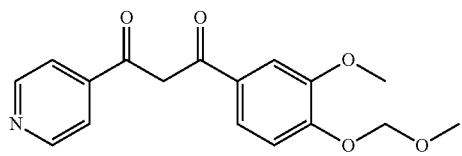
30a

NaH (60% w/w in mineral oil, 345 mg, 8.64 mmol) was suspended in anhydrous THF (6 mL) and cooled to 0° C., then methyl 1-(3-methoxy-4-(methoxymethoxy)phenyl) ethanone (666 mg, 3.17 mmol) in THF (2 mL) was added dropwise. The mixture was stirred during 45 min at 0° C. A solution of methyl isoniconate (500 mg, 2.88 mmol) in THF (2 mL) was then added. The mixture was stirred overnight at rt. The reaction was quenched by citric acid solution in water (10% w/w) and the mixture was extracted with EtOAc. The combined organic layers were washed twice with water, once with brine then dried over anhydrous $Na_2SO_4$. After evaporation of the solvent, the residue was purified by flash chromatography on silica gel eluting with 80% EtOAc in n-heptane+0.1% $Et_3N$, affording 297 mg (33% yield) of a yellow solid.

$^1$H NMR (400 MHz, $CDCl_3$) δ 8.79 (d, 2H, J=6.1 Hz), 7.78 (dd, 2H, J=4.6, 1.7 Hz), 7.61-7.57 (m, 2H), 7.24 (d, 1H, J=7.9 Hz), 6.84 (s, 1H), 5.33 (s, 2H), 3.99 (s, 3H), 3.53 (s, 3H). $^{13}$C NMR (100 MHz, $CDCl_3$) δ 188.9, 179.2, 151.2, 150.6, 150.0, 142.5, 129.7, 121.7, 120.5, 115.0, 110.6, 95.2, 93.8, 56.6, 56.3; MS (ESI-TOF): m/z=316.1 [M+H]$^+$; RT: 3.54 min; mp: 97-99° C.

6-(4-hydroxy-3-methoxyphenyl)-4-(pyridin-4-yl)pyrimidin-2(1H)-one (30)

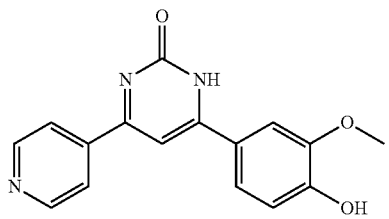

(30)

Synthesis was performed following general procedure B (at 120° C. overnight), from 1-(3-methoxy-4-(methoxymethoxy)phenyl)-3-(pyridin-3-yl)propane-1,3-dione (77 mg, 0.24 mmol). The residue was purified by flash chromatography (5-50% MeCN in water) and evaporated to obtain the desired product (9.2 mg, 0.03 mmol, 13%) as a yellow solid.

$^1$H NMR (400 MHz, (CD3)$_2$SO) 9.87 (s, 1H), 8.79 (d, 2H, J=4.7 Hz), 8.12 (d, 2H, J=5.8 Hz), 7.73-7.71 (m, 2H), 7.64 (s, 1H), 6.92 (d, 1H, J=9.3 Hz), 3.90 (s, 3H). $^{13}$C NMR (100 MHz, (CD3)$_2$SO) δ 177.8, 150.6, 150.2, 147.9, 121.7, 121.5, 115.6, 111.2, 76.8, 55.9. HRMS (ES$^+$) m/z for $C_{16}H_{13}N_3O_3$ calc 295.09569, found 296.09529; RT: 2.06 min; mp: 330-332° C.

6-(4-hydroxy-3-methoxyphenyl)-4-(thiazol-2-yl)pyrimidin-2(1H)-one (31)

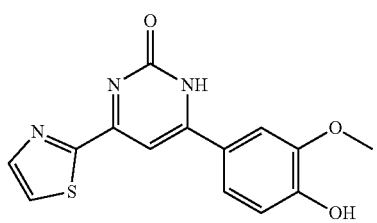

(31)

Synthesis was performed following general procedure C from 2-acetylthiazole (3.8 mmol, 488 mg, 1 equiv). Hot EtOH was added to the reaction mixture and filtered to obtain the desired product as a green solid (260 mg, 0.86 mmol, 22%).

$^1$H NMR (400 MHz, DMSO-$d_6$) δ 8.14 (d, J=3.14 Hz, 1H), 8.07 (d, J=3.14 Hz, 1H), 7.62 (s, 1H), 7.49-7.59 (m, 2H), 6.94 (d, J=8.41 Hz, 1H), 3.90 (s, 3H); $^{13}$C NMR (101 MHz, DMSO-$d_6$) δ 167.0, 166.9, 151.1, 148.4, 145.5, 125.9, 125.9, 125.9, 121.8, 116.3, 111.4, 109.3, 56.3; MS (ESI-TOF): m/z=302.4[M+H]$^+$; RT: 2.86 min; mp: 303° C.-305° C.

4-(4-chlorothiophen-2-yl)-6-(4-hydroxy-3-methoxyphenyl)pyrimidin-2(1H)-one (32)

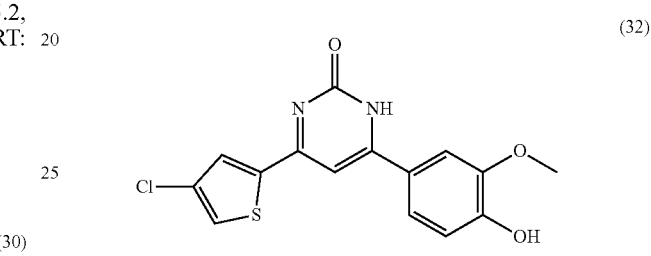

(32)

Synthesis was performed following general procedure C from 1-(4-chlorothiophen-2-yl)ethan-1-one (3.3 mmol, 0.4 ml, 1 equiv). Hot EtOH was added to the reaction mixture and filtered to obtain the desired product as a yellow solid (74 mg, 0.22 mmol, 7%).

$^1$H NMR (400 MHz, DMSO-$d_6$) δ 11.83 (br s, 1H), 9.18-10.81 (m, 1H), 8.27 (s, 1H), 7.87 (s, 1H), 7.85-7.90 (m, 1H), 7.57-7.66 (m, 2H), 7.50 (br s, 1H), 6.92 (d, J=8.16 Hz, 1H), 3.76-4.09 (m, 3H); $^{13}$C NMR (101 MHz, DMSO-$d_6$) δ 129.9, 127.3, 121.8, 116.1, 111.5, 56.4, 40.5, 40.3; MS (ESI-TOF): m/z=334.9 [M+H]$^+$; RT: 3.72 min; mp: 328° C.-330° C.

4-(5-chlorothiophen-2-yl)-6-(4-hydroxy-3-methoxyphenyl)pyrimidin-2(1H)-one (33)

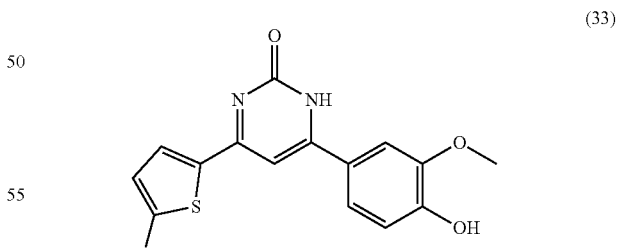

(33)

Synthesis was performed following general procedure C from 2-acetyl-5-chlorothiophene (2.49 mmol, 400 mg, 1 equiv). Hot EtOH was added to the reaction mixture and filtered to obtain the desired product as a yellow solid (74 mg, 0.22 mmol, 7%).

$^1$H NMR (400 MHz, DMSO-$d_6$) δ 8.13 (d, J=4.02 Hz, 1H), 7.54-7.65 (m, 2H), 7.44 (br s, 1H), 7.32 (d, J=4.02 Hz, 1H), 6.92 (d, J=8.28 Hz, 1H), 3.90 (s, 3H); $^{13}$C NMR (101

MHz, DMSO-$d_6$) δ 150.9, 148.3, 129.2, 121.8, 116.1, 111.5, 56.4; MS (ESI-TOF): m/z=334.9[M+H]$^+$; RT: 3.72 min; mp: 298° C.-300° C.

6-(4-hydroxy-3-methoxyphenyl)-4-(pyrazin-2-yl)pyrimidin-2(1H)-one (34)

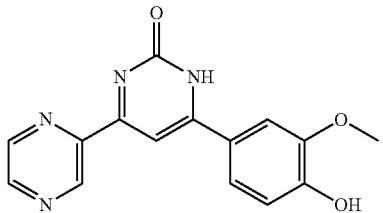

(34)

Synthesis was performed following general procedure C from acetylpyrazine (2.46 mmol, 300 mg, 1 equiv). Hot EtOH was added to the reaction mixture and filtered to obtain the desired product as a yellow solid (179 mg, 0.60 mmol, 25%).

$^1$H NMR (400 MHz, DMSO-$d_6$) δ 12.07 (br s, 1H), 9.91 (s, 1H), 9.50 (s, 1H), 8.82-8.88 (m, 2H), 7.78 (br s, 1H), 7.68 (s, 1H), 7.62 (br d, J=8.03 Hz, 1H), 6.94 (d, J=8.28 Hz, 1H), 3.90 (s, 3H); $^{13}$C NMR (101 MHz, DMSO-$d_6$) δ 147.3, 144.8, 143.7, 121.9, 116.2, 111.3, 56.2; MS (ESI-TOF): m/z=297.0[M+H]$^+$; RT: 2.54 min; mp: 340° C.-342° C.

6-(4-hydroxy-3-methoxyphenyl)-4-(thiazol-4-yl)pyrimidin-2(1H)-one (35)

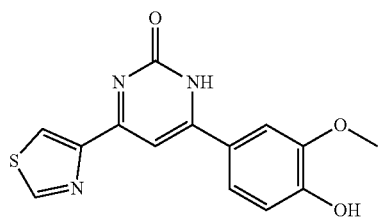

(35)

Synthesis was performed following general procedure C from 1-(1,3-thiazol-4-yl)ethan-1-one (2.36 mmol, 300 mg, 1 equiv). Hot EtOH was added to the reaction mixture and filtered to obtain the desired product as an orange solid (320 mg, 1.06 mmol, 45%).

$^1$H NMR 9.31 (s, 1H), 8.68 (br s, 1H), 7.66 (br s, 1H), 7.51-7.62 (m, 1H), 6.93 (br d, J=8.16 Hz, 1H), 3.90 (s, 3H); $^{13}$C NMR (101 MHz, DMSO-$d_6$) δ 156.2, 123.4, 121.8, 116.2, 111.3, 56.2, 40.3; MS (ESI-TOF): m/z=302.9[M+H]$^+$; RT: 2.46 min.

6-(4-hydroxy-3-methoxyphenyl)-4-(thiophen-2-yl)pyrimidin-2(1H)-one (36)

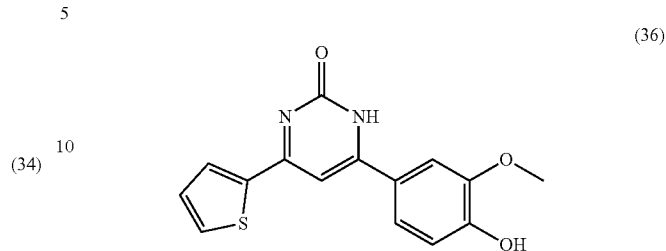

(36)

Synthesis was performed following general procedure C from 2-acetylthiophene (3.7 mmol, 0.4 mL, 1 equiv). Hot EtOH was added to the reaction mixture and filtered to obtain the desired product as a yellow solid (270 mg, 0.89 mmol, 24%).

$^1$H NMR (400 MHz, DMSO-$d_6$) δ 3.91 (s, 3H), 6.93 (d, J=8.31 Hz, 1H), 7.27 (t, J=4.56 Hz, 1H), 7.42 (s, 1H), 7.53-7.68 (m, 2H), 7.86 (d, J=4.89 Hz, 1H), 8.21 (d, J=3.42 Hz, 1H); $^{13}$C NMR (101 MHz, DMSO-$d_6$) δ 132.7, 130.7, 129.1, 121.7, 116.1, 111.5, 56.3; MS (ESI-TOF): m/z=301.9 [M+H]$^+$; RT: 2.88 min; mp: 269.4-271.1° C.

6-(4-hydroxy-3-methoxyphenyl)-4-(thiophen-3-yl)pyrimidin-2(1H)-one (37)

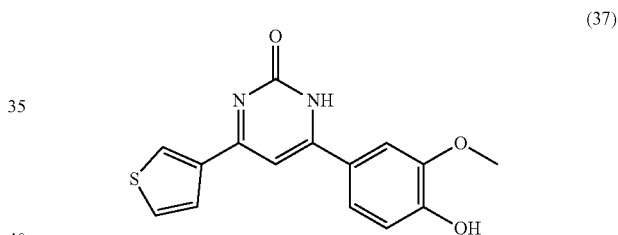

(37)

Synthesis was performed following general procedure C from 3-acetylthiophene (3.7 mmol, 463 mg, 1 equiv). Hot EtOH was added to the reaction mixture and filtered to obtain the desired product as a yellow solid (185 mg, 0.62 mmol, 17%).

$^1$H NMR (400 MHz, DMSO-$d_6$) δ 3.89 (s, 3H), 6.93 (br d, J=7.8 Hz, 1H), 7.39 (s, 1H), 7.61-7.81 (m, 3H), 7.91 (br d, J=4.6 Hz, 1H), 8.60 (br s, 1H); $^{13}$C NMR (101 MHz, DMSO-$d_6$) δ 129.3, 128.0, 122.0, 116.0, 111.5, 56.3; MS (ESI-TOF): m/z=301.1[M+H]; RT: 2.73 min; mp: 272.5-273.1° C.

(E)-1-(6-(dimethylamino)pyridin-3-yl)-3-(4-hydroxy-3-methoxyphenyl)prop-2-en-1-one "38a"

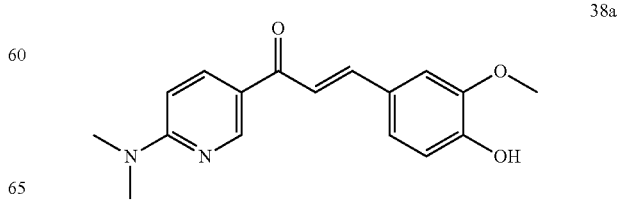

38a

Vanillin (131 mg, 0.862 mmol, 1.02 equiv) was added to DIMCARB (2.16 mL, 16.9 mmol, 20 equiv) in DCE (0.7 mL) at ambient temperature with stirring. 2-Chloro-5-acetylpyridine (131 mg, 0.845 mmol, 1 equiv) was added in a single portion to the reaction mixture. The reaction was stirred overnight at 50° C. The solvent was evaporated, and the crude solid was treated with 2N $H_2SO_4$ (neutralization of the remaining amine). The crude product was purified by flash chromatography on a 12 g silica gel column (hexanes/EtOAc 10:0 to 10:10 to 0:10 (v/v) in 30 min) to afford a yellow solid (190 mg, 0.637 mmol, 75%).

HPLC Purity=100%; tr=2.85 min; $^1$H NMR (400 MHz, CDCl$_3$) δ 8.93 (d, J=2.0 Hz, 1H), 8.26 (d, J=9.0 Hz, 1H), 7.78 (d, J=15.3 Hz, 1H), 7.34 (d, J=15.3 Hz, 1H), 7.20 (dd, J=8.0, 2.0 Hz, 1H), 7.15 (d, J=2.0 Hz, 1H), 6.96 (d, J=8.0 Hz, 1H), 6.69 (d, J=9.0 Hz, 1H), 6.02 (br s, 1H), 3.98 (s, 3H), 3.31 (s, 6H). MS (ESI$^+$): m/z=299 [M+H]$^+$.

4-(6-(dimethylamino)pyridin-3-yl)-6-(4-hydroxy-3-methoxyphenyl)pyrimidin-2(1H)-one Hydrochloride (38)

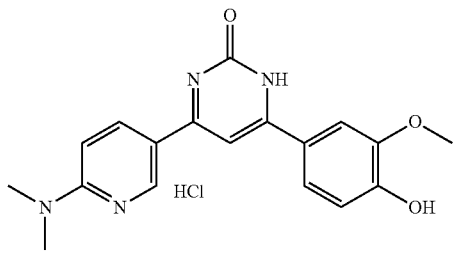

(38)

Compound (38) is obtained from compound 38a according to general procedure B.

Orange solid (60 mg, 0.177 mmol, 30%). HPLC Purity=97%; tr=2.42 min; mp 257-260° C.; $^1$H NMR (400 MHz, DMSO-d$_6$) δ 11.64 (br s, 1H), 9.76 (br s, 1H), 8.94 (s, 1H), 8.24 (s, 1H), 7.66-7.63 (m, 2H), 7.30 (s, 1H), 6.89 (d, J=8.8 Hz, 1H), 6.75 (d, J=8.8 Hz, 1H), 3.89 (s, 3H), 3.13 (s, 6H); $^{13}$C NMR (126 MHz, DMSO-d$_6$) δ 160.0, 159.5, 150.1, 147.7, 135.9, 115.5, 111.0, 105.2, 55.8, 37.6; HRMS (ESI-TOF): calcd for $C_{18}H_{19}N_4O_3$ [M+H]$^+$: 339.1457, found 339.1451.

(2E)-3-(4-hydroxy-3-methoxyphenyl)-1-(1H-pyrrol-2-yl)prop-2-en-1-one (60)

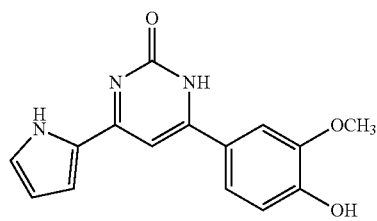

(60)

Step 1: synthesis of (2E)-3-(4-hydroxy-3-methoxyphenyl)-1-(1H-pyrrol-2-yl)prop-2-en-1-one ("60a")

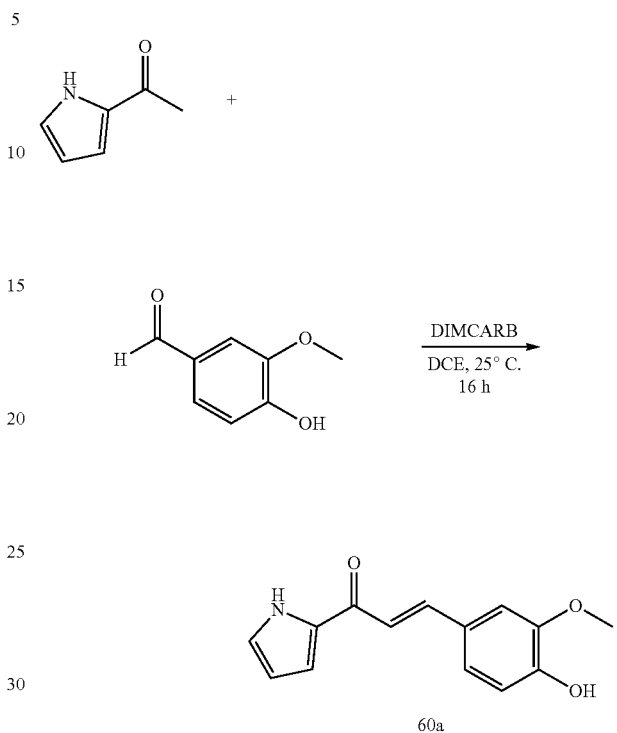

60a

Vanillin (1.02 eq., 711 mg, 0.671 mL, 4.67 mmol) was added to DIMCARB (15 eq., 9221 mg, 8.78 mL, 68.7 mmol) in DCE (3.63 mL) at ambient temperature with stirring. Gas was evolved. 2-acetyl pyrrole (1 eq., 500 mg, 4.58 mmol) was added in a single portion to the reaction mixture. The reaction was stirred overnight at 50° C. The residue was then purified by chromatography (AcOEt/hept 7:3) to obtain (2E)-3-(4-hydroxy-3-methoxyphenyl)-1-(1H-pyrrol-2-yl) prop-2-en-1-one as a yellow solid (213 mg, 0.88 mmol, 19%) Step 2: synthesis of (2E)-3-(4-hydroxy-3-methoxyphenyl)-1-(1H-pyrrol-2-yl)prop-2-en-1-one (60) Synthesis was performed following general procedure C from 60a. The residue was purified by flash chromatography on a C18 column (5-60% MeCN in water) and concentrated under vacuum to obtain the desired product (12 mg, 0.04 mmol, 5%) as a yellow solid.

$^1$H NMR (400 MHz, DMSO-d$_6$) δ ppm 12.46 (s, 1H), 10.37 (s, 1H), 7.59-7.73 (m, 3H), 7.54 (s, 1H), 7.43 (s, 1H), 7.01 (d, J=8.0 Hz, 1H), 6.44-6.59 (m, 1H), 3.92 (s, 3H); $^{13}$C NMR DEPT 135 (126 MHz, DMSO-d$_6$) δ ppm 158.5, 158.2, 148.5, 123.3, 123.3, 116.5, 112, 56.5 MS(ESI$^+$): m/z=284.1 [M+H]$^+$; RT: 2.60 min; mp=128-130° C.

Example 2: In Vitro Study of Compounds (1) to (10), (28), (33) (59) and 60 of General Formula (I)

The inhibition of the CXCR4-CXCL12 binding was studied with compounds (1) to (10) of general formula (I) and with three other compounds, named (A) to (C), having a structure close to formula (I) but which do not belong to formula (I).

Said three compounds (A) to (C) are respectively the following:

4-(4-chlorophenyl)-6-(4-hydroxyphenyl)pyrimidin-2(1H)-one (compound (A))

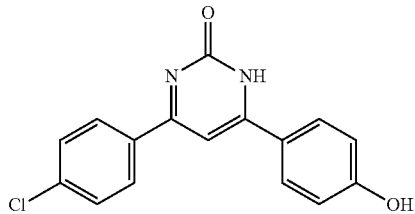

(A)

4-(4-chlorophenyl)-6-phenylpyrimidin-2(1H)-one (compound (B))

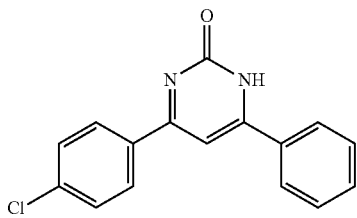

(B)

4-(4-chlorophenyl)-6-(3-methoxyphenyl)pyrimidin-2(1H)-one (compound (C))

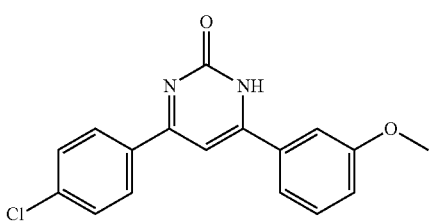

(C)

The compounds (1) to (10) of the invention respond to general formula (I) wherein:
A is a phenyl group having the following formula:

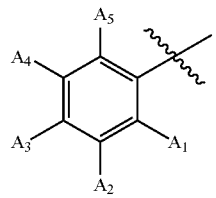

$A_1$, $A_2$, $A_4$, $B_3$, $B_4$, $B_5$ and Y represent H,
X represent O, and
$A_3$, $A_5$, $B_1$ and $B_2$ are defined in table 2 below.

General formula (I) of compounds (1) to (10) is thus represented by:

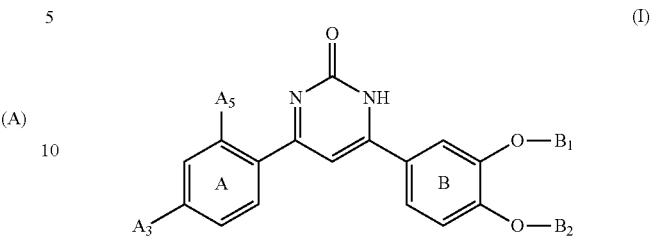

(I)

Neutraligand Characterization

Study of the changes of CXCR4-CXCL12 binding was achieved by the energy transfer technique[10,11].

Binding of Texas red-labelled CXCL12 with CXCR4-GFP fused receptor[11] induces fluorescence resonance energy transfer (FRET), which can be monitored by the reduction of GFP fluorescence emission. The characterization of CXCL12 neutraligands was evaluated in two conditions, differing by the sequence of addition of molecules. Reduction of GFP fluorescence emission was more important when neutraligands were preincubated (30 min) with the cells expressing CXCR4 receptor than when neutraligands were preincubated with CXCL12 prior to the addition to cells.

The compounds were tested at a concentration of $10 \times K_i$ (inhibition constant). The CXCR4 antagonist, T134 (20 µM) was used as a control in both incubation protocols. Data obtained were consistent with a binding to the chemokine and not to its receptor. Consequently, all selected compounds are indeed CXCL12 chemokine neutraligands and behave as chalcone-4. The neutralizing properties of the compounds are thus confirmed.

Results of the inhibition of CXCL12-TR binding obtained with compounds (1) to (10) of the invention and compounds (A) to (C) are summarized in Table 2 below.

TABLE 2

| Tested compounds | $A_3$ | $A_5$ | $B_1$ | $B_2$ | Inhibition of CXCL12-TR binding 10 µM, % |
|---|---|---|---|---|---|
| (1) | Cl | H | $CH_3$ | H | 92 ± 5 |
| (2) | $OCH_3$ | H | $CH_3$ | H | 96 ± 3 |
| (3) | OH | H | $CH_3$ | H | 53 ± 6 |
| (4) | iPr | H | $CH_3$ | H | 35 ± 4 |
| (5) | F | H | $CH_3$ | H | 46 ± 4 |
| (7) | H | Cl | $CH_3$ | H | 62 ± 5 |
| (8) | H | H | $CH_3$ | H | 46 ± 8 |
| (9) | Cl | H | $CF_3$ | H | 52 ± 10 |
| (10) | Cl | H | H | $CH_3$ | 39 ± 7 |
| (A) | Cl | H | —* | H | 4.3 ± 3 |
| (B) | Cl | H | —** | —** | 19 ± 7 |
| (C) | Cl | H | $CH_3$ | —*** | 10 ± 5 |

*in compound (A) the "O-$B_1$" group does not exist and is replaced by a hydrogen.
**in compound (B) the "O-$B_1$" group and the "O-$B_2$" group do not exist and are each replaced by a hydrogen.
***in compound (C) the "O-$B_2$" group does not exist and is replaced by a hydrogen.

In the same way, the inhibition of the CXCR4-CXCL12 binding was studied with compounds (1) and (59) of general formula (I) and with other compounds, named (D) and (E), having a structure close to formula (I) but which do not belong to formula (I), as well as with Chalcone-4).

The two compounds (D) and (E) are respectively the following:

4-(4-chlorophenyl)-6-(4-methoxy-3-methoxyphenyl) pyrimidin-2(1H)-one (D)

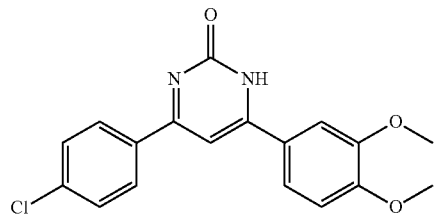

(D)

4-(4-hydroxy-3-methylphenyl)-6-(4-methoxy-3-methoxyphenyl)pyrimidin-2(1H)-one (E)

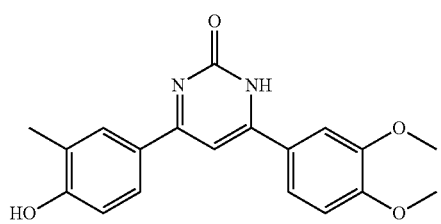

(E)

Results of the inhibition of CXCL12-TR binding are summarized in Table 3 below.

TABLE 3

| Tested compounds | Inhibition of CXCL12-TR binding 10 µM, % |
| --- | --- |
| (D) | 26 ± 1 |
| (E) | 1.8 ± 0.7 |
| 59 | 83 ± 2 |
| Chalcone-4 | 96 ± 2 |
| 1 | 76 ± 5 |

Inhibition of the CXCR4-CXCL12 binding was also studied with compounds (1), (28), (33), and (60) of general formula (I).

Results are summarized in Table 4 below.

TABLE 4

| Tested compounds | Inhibition of CXCL12-TR binding 10 µM, % |
| --- | --- |
| 28 | 44 ± 1 |
| 33 | 58 ± 15 |
| 60 | 53 ± 14 |
| 1 | 76 ± 5 |

Structure-Activity Relationship (SAR)

One can deduce from these comparative examples that removing the hydroxyl substituent (OH) in para position of the B cycle leads to a loss of affinity of compound (C) for CXCL12.

In the same way, removing the methoxy substituent (OCH$_3$) in meta position of the B cycle leads to a loss of affinity of compound (A) for CXCL12.

Compounds (1) and (59) of the invention are far better than compounds (D) and (E) which do not possess an OH substituent in para position of the B cycle.

Conclusion:

Even if some compounds are better than others, all compounds (1) to (10), (28), (33), (59) and (60) of formula (I) are interesting CXCL12 chemokine neutraligands.

Example 3: Solubility and Stability of Compound (1)

Among the compounds identified as CXCL12 neutraligands in the in vitro study, compound (1) was selected for in vivo studies.

The results of the solubility and stability of neutraligand (1) and of chalcone-4 are reported in Table 5 below.

Their solubility in assay media was evaluated. (2-Hydroxypropyl)-o-cyclodextrin (Cdx) was used as excipient because of its low toxicity and its capacity to increase bioavailability. Solubility in PBS/Cdx (10% w/w) was assessed and showed that all compounds can be tested at a 300 µM concentration without artefacts. The compound stability was evaluated in PBS only and in PBS/Cdx.

TABLE 5

Solubility and stability of compound (1) and chalcone 4

| | Solubility µM | | Stability[a] | |
| --- | --- | --- | --- | --- |
| Compd | PBS | PBS/Cdx | PBS | PBS/Cdx |
| Chalcone-4 | 9 | >300 | 100% | 100% |
| 1 | 36.4 | >5000 | 100% | 100% |

[a]Monitored after 24 h in HEPES-BSA buffer

Example 4: In Vivo Biological Evaluation of Compound (1) in a Mouse Model of Airway Allergic Eosinophilic Inflammation Asthma is one of the most common chronic inflammatory diseases, and a major health problem with 300 million cases worldwide, imposing a considerable burden on society in morbidity, quality of life, and healthcare costs. Although great advances have been made in the understanding of the mechanisms of chronic inflammation in asthma, there has been little progress in developing new medications, and the association between inhaled glucocorticoids and the bronchorelaxant B$_2$-agonists form the gold standard, first-line therapy of persistent asthma to alleviate bronchial inflammation together with bronchoconstriction. Unfortunately for the patients, long-term use of high dose inhaled glucocorticoid therapy has potential to cause systemic side effects including dysphonia, topical candidiasis, lung infection, intraocular pressure and cataracts, and skeletal effects with osteoporosis in elderly and growth deceleration in children. The most recent studies suggest that chemokine and their receptors may be targeted in asthma and atopic diseases.

The in vivo activity of compound (1) was tested in the 8-day murine model of allergic eosinophilic airway inflammation previously described[13].

Briefly, Balb/c mice were sensitized to ovalbumin (OVA) and challenged 3 times with OVA or saline at 24 h interval. Treatments with each compound (300 nmol/kg in 10%

PBS/Cdx) were administered by the intranasal route 2 h before each challenge. Bronchoalveolar lavage was performed 24 h after the last challenge, and eosinophil, macrophage, neutrophil and lymphocyte numbers quantified.

Using the same protocol, the dose-response of compound (1) and chalcone-4 was evaluated on eosinophil recruitment after intranasal administration (FIG. 1).

The reference chalcone 4 had an $IC_{50}$ higher than 500 nmol/kg, but the actual value could not be determined precisely because the solubility threshold was reached at this concentration in PBS/Cdx. In contrast, the novel pyrimidinone (1) proved to be more soluble, and its calculated $IC_{50}$ was 300 nmol/kg. Furthermore, the selectivity of (1) was also evaluated towards two other chemokines, namely CCL17 and CCL22, with no activity at 5 µM (data not shown).

Overall, pyrimidinone (1) is a novel CXCL12 neutraligand, one of the most potent and soluble in our in vitro SAR (structure-activity relationship) studies and the most active to date in the in vivo inhibition of allergic eosinophilic airway inflammation in mice.

Conclusion:

Pyrimidinone (1) (300 nmol/kg, intranasal route, n=6) inhibits the recruitment of eosinophils in a murine model of allergen-sensitized and -challenged mice with bronchial hypereosinophilia in asthma.

Example 5: In Vivo Biological Evaluation of Compound (1) in a Mouse Model of Atopic Dermatitis The in vivo activity of compound (1) was tested in a murine model of atopic dermatitis as previously described (Zhang et al, *Proc Nat Acad Si USA* 2009, 106, 1536-41). Briefly, Balb/c mice were topically administered with a vitamin D analogue, MC903 (2 or 4 nmol/ear) every other day for 13 days. Treatments with each compound (350 µmol/Kg in acetone/olive oil 50/50) were topically applied 2 h before each MC903 application.

The effect of the neutraligand (1) and chalcone-4 (reference compound) is seen morphologically (photographs in FIG. 2A) and was evaluated on ear thickness (FIG. 2B) comparatively to the inactive chalcone-1, which is not a CXCL12 neutraligands (FIG. 2C). The reference chalcone-4 and compound (1) totally abolished the atopic response to MC903.

Example 6: In Vivo Biological Evaluation of Compound (1) in a Mouse Model of Airway Neutrophilic Inflammation of Chronic Obstructive Pulmonary Disease (COPD)

The in vivo activity of compound (1) was tested in the murine model of neutrophilic airway inflammation induced by lipopolysaccharide (LPS) as previously described (Flacher et al, *ACS Chem Biol.* 2015, 10:2697-705)[14].

Briefly, Balb/c mice were administered intranasally with LPS (lipopolysaccharide from *E. coli*, O55B5, 1 µg, Sigma Aldrich) or saline. Treatments with (1) or Chalcone-4 (350 µmol/kg) in 1% CMC (carboxymethylcellulose) were administered by the intraperitoneal route 2 h before LPS instillation. Bronchoalveolar lavage was performed 24 h after LPS, and neutrophil, lymphocyte, eosinophil and macrophage numbers quantified.

Figure 3:
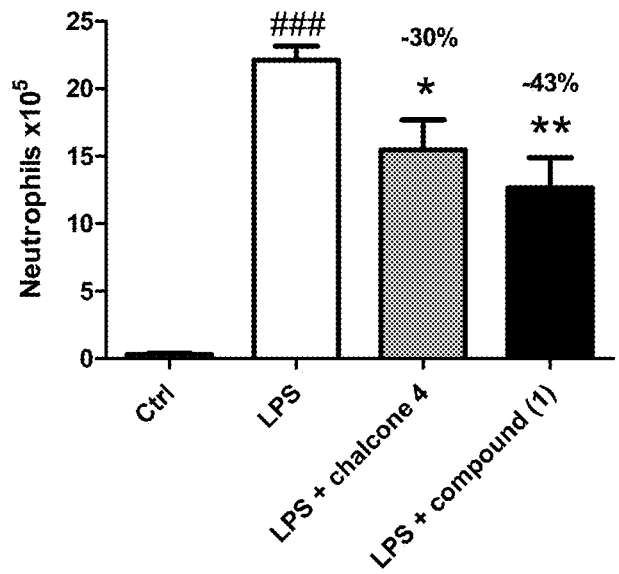

The reference chalcone-4 showed 30% inhibition of neutrophil recruitment at 350 µmol/kg. The novel pyrimidinone (1) reduced neutrophil recruitment by 43% (FIG. 3).

Overall, compound (1) is a novel CXCL12 neutraligand, one of the most potent and soluble in our in vitro SAR studies and the most active to date in the in vivo inhibition of airway neutrophilic inflammation in mice.

Conclusion:

Compound (1) (350 µmol/kg i.p., n=6) inhibits the recruitment of polymorphonuclear neutrophils induced by LPS (intranasally, 1 µg), a first model for neutrophilic inflammation in COPD.

Example 7: In Vivo Evaluation of Compound (1) in Lupus

The Animal Model and the Assay.

MRL/lpr lupus prone mice, which is the most commonly studied mouse model of the disease, bears an autosomic recessive mutation in the gene encoding Fas[15]. The MRL[+/+] background is responsible for the development of autoimmune kidney disease, and the lymphoproliferation (lpr)/Fas mutation converts a mild nephritis into a much severe disease, with a 50% mortality rate at 24 weeks of age[13].

Based on the fact that compared to normal mice (e.g. CBA/J mice), MRL/lpr mice show an elevated number of leukocytes in their blood, which is easy to measure, we have established a rapid, robust and reliable routine assay allowing to evaluate in vivo properties of compounds by measuring the decrease of this abnormal peripheral hypercellularity a few days after administration[14]

Peripheral Hypercellularity Measurements.

The test was as described previously (Schall et al., 2012; Briand et al., 2014). All experimental protocols were carried out with the approval of the French Institutional Animal Care and Use Committee. Briefly, groups of 11-13 week-old MRL/lpr mice (same age and sex, male or female) were injected intravenously (retro-orbital route) with 100 µg of each molecule per 100 µL of 9% o NaCl: chalcone 4-phosphate or compound (1) (in PBS/Cdx 10%), or cyclophosphamide, hydroxychloroquine, amethopterin, azathioprine, or mycophenolate mofetil (8-10 mice/condition). The control group of mice received 100 µL of 9% o NaCl only. After 5 days, mice were bled individually. Red blood cells were lysed using EasyLyse reagent (DAKO, ref. S2364) according to the manufacturer's protocol. After centrifugation, white blood cells (WBCs) resuspended in phosphate buffer saline containing fetal calf serum were stained with acridine orange/propidium iodide and counted using a LUNA FL apparatus (logos Biosystems, Annandale, USA). The number of living WBCs in each group was compared to the one counted in the control group and the decrease of peripheral cell number was calculated. To avoid any bias due to groups of mice, the results mixed from several independent experiments are presented. The results are expressed as the mean decreased of peripheral WBCs percentage SEM. Statistical differences were determined using the unpaired t test. Statistical results were calculated using the graphPad Prism software.

Results with Compound (1).

Figure 4:
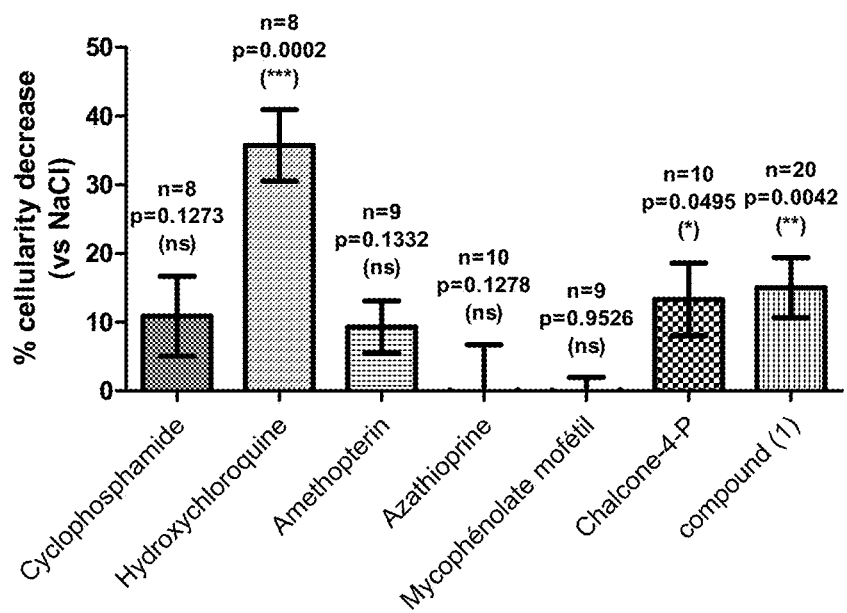

As shown in FIG. 4, chalcone-4-P (administered i.v.), and compound (1) (administered i.v. at a dose of 3.9 mg/kg in Cdx 10%), significantly reduce peripheral blood hypercellularity (p <0.05).

Example 8: In Vivo Evaluation of Compound (1) in the Model of Fentanyl-Induced Hyperalgesia Pain is a major health problem that substantially reduces quality of life and imparts high health costs and economic loss to society. Although in recent years great advances have been made in the understanding of mechanisms that underlie pain, there has been little progress in developing new analgesics, and systemic administration of opiate analgesics such as morphine still remains the most effective means of alleviating severe pain across a wide range of conditions. Unfortunately for the patients, opiate treatments are associated with several side effects including the development of pain hypersensitivity (hyperalgesia), which have been proposed to be responsible for the decrease in the efficacy of treatment over time (tolerance).

The most recent studies suggest that chemokine and their receptors are involved in these phenomena[20].

In this example we investigated in mice whether a neutralizing compound of CXCL12, compound (1), when co-administered with an opiate can prevent the development of secondary hyperalgesia induced by opiate administration.

Experiments were conducted on adult male C57BL/6J mice housed in groups of five per cage under a 12 h/12 h light/dark cycle at a constant temperature (21±1° C.) with free access to food and water. They were habituated to the experimental room and handled for one week before starting experiments. Every mouse was used only once.

Model of Fentanyl-Induced Hyperalgesia in Mice.

Analgesia and hyperalgesia induced by fentanyl were evaluated as previously described[16]. A dose of fentanyl was injected four times (4×60 µg·kg$^{-1}$, s.c.) at 15 min intervals, which mimics its use in human surgery. The nociceptive threshold of naive and treated mice was assessed in the tail immersion test[17] by measuring the latency time to withdraw their tail from a thermostated (48±0.5° C.) water bath.

As shown in FIG. 5, when fentanyl was administered to mice, it induced an analgesic effect (increase of tail withdrawal latency) that lasted 2 hours after its administration. In the following days (D1, D2 and D3), animals that were injected with fentanyl alone on day 0 displayed a strong decrease of their basal nociceptive threshold indicating that they developed pain hypersensitivity. Compound (1) alone (50 mg/kg, i.p.) had no effect on the nociceptive threshold of the animals while it completely prevented the development of secondary hyperalgesia induced by fentanyl when it was co-administered with fentanyl at the dose of 10 mg/kg. A similar effect was observed with chalcone-4 at 100 mg/kg. The analgesic effect of fentanyl was preserved in animals that were co-administered with compound (1) and chalcone-4.

Example 9: In Vivo Evaluation of Compound (1) on Pulmonary Hypertension (PH)

The combination of pulmonary vasoconstriction, in situ thrombosis, and pulmonary arterial wall remodeling is largely responsible for the rise in pulmonary vascular resistance (PVR) and pulmonary arterial pressure (PAP) in patients with pulmonary arterial hypertension (PAH).

Although the spectrum of therapeutic options for PAH has expanded in the last decade, available therapies remain essentially palliative.

Experimental Strategy.

The activity of compound (1) vs chalcone-4 was evaluated in an animal model of pulmonary hypertension (PH) (by convention, animal models are still referred to as having PH rather than PAH): the SU-5416 (20 mg/Kg)/Hypoxia rat model. Chalcone-4 and compound (1) (100 mg/kg/day) were prepared in carboxymethylcellulose (CMC 1% in saline) and administered I.P. Rats were treated for 3 weeks in a curative protocol, and were then left for 2 weeks in normoxia. An additional group of healthy rats with no PH was used as the control group (CTR).

The SU-5416/Hypoxia Rat Model.

PH was induced by a single subcutaneous injection of SU5416 (20 mg/kg) in Wistar rats, followed by a 3-week exposure to chronic hypoxia (10% $FiO_2$). Right ventricular structure and function was assessed by echocardiography using the GE Vivid 9 ultrasound. Before treatment begins, echocardiography measurements of each rat have been performed to validate the presence of PH in animals (acceleration time/ejection time). Then, the rats were randomized by numbering the animals from 1 to 4 in each cage at the beginning of the study, and then looking at a random number table. Each rat has been treated by intraperitoneal administration. At the end of the treatment period, a right heart catheterization (RHC) was performed to determine the PH severity and the cardiac function.

Right Heart Catheterization (RHC).

Animals were anesthetized with isoflurane. A polyvinyl catheter was introduced into the right jugular vein and pushed through the right ventricle into the pulmonary artery. Cardiac output in rats was measured using the thermodilution method.

Assessment of Right Ventricular Hypertrophy (RVH).

After measurement of hemodynamic parameters, the thorax was opened and the left lung immediately removed and frozen. The right lung was fixed in the distended state with formalin buffer. The right ventricular hypertrophy assessed by the Fulton index [weight ratio of right ventricle (RV) and (left ventricle (LV)+septum)] and the percentage of wall thickness [(2× medial wall thickness/external diameter)× 100] and of muscularized vessels were determined as previously described[21].

Lung Histology and Immunostaining.

Histological sections were stained with hematoxylin and eosin, and immunohistochemistry for alpha-smooth muscle actin was performed as previously described[1']. Images were taken with a microscope Nikon Eclipse 80i and NIS-Elements BR 2.30 software.

Statistical Analyses.

The data are expressed as means SEM. Statistical significance was tested using the 20 nonparametric Mann-Whitney test or two-way ANOVA with Bonferroni post hoc tests.

Significant difference was assumed at a p value of less than 0.05.

Results 1. Beneficial effects of chalcone-4 and compound (1) on pulmonary hemodynamic parameters and right ventricular hypertrophy in the SuHx rat models.

In this curative protocol, a substantial decrease in values of total pulmonary vascular resistance (TPVR) was noted in SuHx rats treated with chalcone-4 and compound (1) when compared with the SuHx rats treated with vehicle.

Interestingly, a substantial increase in values of cardiac output in SuHx rats treated with compound (1) was compared with the SuHx rats treated with vehicle or chalcone-4. Consistent with these findings, a significant decrease in values of Fulton index (assessing right ventricular hypertrophy) in SuHx rats treated with (1) when compared with the SuHx rats treated with vehicle or chalcone-4 (FIG. 6A).

2. Beneficial Effects of Chalcone-4 and Compound (1) on the Pulmonary Vascular Remodeling in the SuHx Rat Models.

Consistent with our observations, chalcone-4 and compound (1) substantially attenuated the pulmonary vascular remodeling in the SuHx rat model (FIGS. 6B and 6C). Eight weeks after the SU-5416 administration, in SuHX rats treated with vehicle, a pronounced pulmonary vascular remodeling was noted with occluded distal pulmonary arteries, that was attenuated in SuHx rats treated with chalcone-4 and compound (1).

BIBLIOGRAPHY

1. Fernandez E J, Lolis E. Structure, function, and inhibition of chemokines. *Annual review of pharmacology and toxicology* 2002; 42: 469-499.
2. Daubeuf F, Hachet-Haas M, Gizzi P, Gasparik V, Bonnet D, Utard V, Hibert M, Frossard N, Galzi J L. An antedrug of the CXCL12 neutraligand blocks experimental allergic asthma without systemic effect in mice. *The Journal of biological chemistry* 2013; 288: 11865-11876.
3. Galzi J L, Hachet-Haas M, Bonnet D, Daubeuf F, Lecat S, Hibert M, Haiech J, Frossard N. Neutralizing endogenous chemokines with small molecules. Principles and potential therapeutic applications. *Pharmacology & Therapeutics* 2010; 126: 39-55.
4. Gasparik V, Daubeuf F, Hachet-Haas M, Rohmer F, Gizzi P, Haiech J, Galzi J L, Hibert M, Bonnet D, Frossard N. Prodrugs of a CXC Chemokine-12 (CXCL12) Neutraligand Prevent Inflammatory Reactions in an Asthma Model in Vivo. *ACS medicinal chemistry letters* 2012; 3:10-14.
5. Hachet-Haas M, Balabanian K, Rohmer F, Pons F, Franchet C, Lecat S, Chow K Y, Dagher R, Gizzi P, Didier B, Lagane B, Kellenberger E, Bonnet D, Baleux F, Haiech J, Parmentier M, Frossard N, Arenzana-Seisdedos F, Hibert M, Galzi J L. Small neutralizing molecules to inhibit actions of the chemokine CXCL12. *The Journal of biological chemistry* 2008; 283: 23189-23199.
6. Balabanian, K.; Brotin, E.; Biajoux, V.; Bouchet-Delbos, L.; Lainey, E.; Fenneteau, O.; Bonnet, D.; Fiette, L.; Emilie, D.; Bachelerie, F. Proper desensitization of CXCR4 is required for lymphocyte development and peripheral compartmentalization in mice. *Blood* 2012, 119, 5722-5730.
7. Romain, B.; Hachet-Haas, M.; Rohr, S.; Brigand, C.; Galzi, J. L.; Gaub, M. P.; Pencreach, E.; Guenot, D. Hypoxia differentially regulated CXCR4 and CXCR7 signaling in colon cancer. *Mol. Cancer* 2014, 13, 58.
8. Valenzuela-Fernandez, A.; Palanche, T.; Amara, A.; Magerus, A.; Altmeyer, R.; Delaunay, T.; Virelizier, J. L.; Baleux, F.; Galzi, J. L.; Arenzana-Seisdedos, F. Optimal inhibition of X4 HIV isolates by the CXC chemokine stromal cell-derived factor 1 alpha requires interaction with cell surface heparan sulfate proteoglycans. *J Biol. Chem.* 2001, 276,
9. Gould, S.; Scott, R. C. 2-Hydroxypropyl-beta-cyclodextrin (HP-beta-CD): a toxicology review. *Food Chem. Toxicol.* 2005, 43, 1451-1459.
10. Z. Zhang, P. Hener, N. Frossard, S. Kato, D. Metzger, M. Li & P. Chambon. Thymic stromal lymphopoietin overproduced by keratinocytes in mouse skin aggravates experimental asthma. *Proc Nat Acad Sci USA,* 106(5): 1536-41, 2009.
11. V Flacher, P Neuberg, F Point, F Daubeuf, Q Muller, D Sigwalt, J D Fauny, J S Remy, N Frossard, A Wagner, C Mueller, E Schaeffer. Mannoside glycolipid conjugates display anti-inflammatory activity by inhibition of Toll-like receptor-4 mediated cell activation. *ACS Chem Biol.* 2015, 10:2697-705.
12. Nagata, S., Suda, T. (1995) Fas and Fas ligand: lpr and gld mutations. *Immunol Today* 16 , 39-43.
13. Theofilopoulos, A. N, Dixon, F. J. (1985) Murine models of systemic lupus erythematosus. *Adv Immunol* 37:269-390.
14. Schall, N., Page, N., Macri, M., Chaloin, O., Briand, J.-P., and Muller, S. (2012) Peptide-based approaches to treat lupus and other autoimmune diseases. *J. Autoimmunity* 39, 143-153.
15. Briand, J.-P., Schall, N. & Muller, S. (2014) Generation of self-peptides to treat systemic lupus erythematosus. Chapter 13, in *Systemic Lupus Erythematosus: Methods and Protocols*, Methods in Molecular Biology (Eggleton P. and Ward, F. J. Eds.), Springer Science+Business Media, New York, vol. 1134, pp 173-192.
16. Célèrier E[1], Rivat C, Jun Y, Laulin J P, Larcher A, Renier P, Simonnet G. Long-lasting hyperalgesia induced by fentanyl in rats: preventive effect of ketamine. Anesthesiology, 2000. 92, 465-472.
17. Elhabazi K[1], Trigo J M, Mollereau C, Mouledous L, Zajac J M, Bihel F, Schmitt M, Bourguignon J J, Meziane H, Petit-demouliere B, Bockel F, Maldonado R, Simonin F. Involvement of neuropeptide F F receptors in neuroadaptive responses to acute and chronic opiate treatments. *Br J Pharmacol,* 2012. 165, 424-35.
18. Guignabert C, Tu L, Izikki M, Dewachter L, Zadigue P, Humbert M, Adnot S, Fadel E, Eddahibi S. Dichloroacetate treatment partially regresses established pulmonary hypertension in mice with SM22alpha-targeted overexpression of the serotonin transporter. FASEB journal 2009; 23: 4135-4147.
19. Tu L, Dewachter L, Gore B, Fadel E, Dartevelle P, Simonneau G, Humbert M, Eddahibi S, Guignabert C. Autocrine fibroblast growth factor-2 signaling contributes to altered endothelial phenotype in pulmonary hypertension. American journal of respiratory cell and molecular biology 2011; 45: 311-322.
20. Parsadaniantz et al., 2015, Nature reviews neuroscience, 16: 69-78.

The invention claimed is:
1. A compound having the general formula (I):

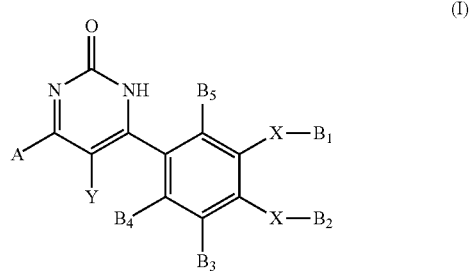

a pharmaceutically acceptable salt thereof or a tautomeric form thereof,
wherein
A represents a cyclic or heterocyclic radical chosen from

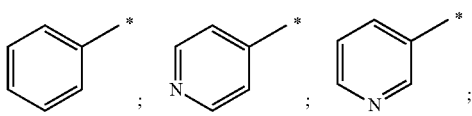

said cyclic or heterocyclic radical may be substituted with substituents chosen from halogen selected from F, I, C or Br; $(C_1-C_{10})$ alkyl; OR with R representing H, $(C_1-C_{10})$ alkyl, $CF_3$; CONHR' with R' representing H, $(C_1-C_6)$alkyl-$NH_2$, a divalent hydrocarbon radical (—$CH_2$—) linked covalently to a cyclic or heterocyclic compound, saturated or unsaturated, chosen from cyclopropyl ($C_3H_5$—), cyclobutyl ($C_4H_7$—), cyclopentyl ($C_5H_9$—), cyclohexyl ($C_6H_{11}$—), morpholinyl piperazinyl, piperazinyl salt phenyl ($C_6H_5$—), benzyl ($C_6H_5CH$—), phenetyl ($C_6H_5CH_2CH_2$—), tolyl ($C_6H_4CH_3$—), xylyl ($C_6H_3(CH_3)_2$—), benzylidene ($C_6H_5CH=CH$—), benzoyl ($C_6H_5CO$), biphenyl (or diphenyl) ($C_{12}H_9$—), naphtyl ($C_{10}H_7$—) or tetrazolyl $COOR_a$, with $R_a$ representing H, $(C_1-C_{10})$alkyl; $NR_aR'_a$ with $R_a$ and $R'_a$ representing independently H, $(C_1-C_{10})$ alkyl; CN; a divalent hydrocarbon radical (—$CH_2$—) linked covalently to a cyclic or heterocyclic compound, saturated or unsaturated, chosen from cyclopropyl ($C_3H_5$—), cyclobutyl ($C_4H_7$—), cyclopentyl ($C_5H_9$—), cyclohexyl ($C_6H_{11}$—), morpholinyl piperazinyl, piperazinyl salt phenyl ($C_6H_5$—), benzyl ($C_6H_5CH$—), phenetyl ($C_6H_5CH_2CH_2$—), tolyl ($C_6H_4CH_3$—), xylyl ($C_6H_3(CH_3)_2$—), benzylidene ($C_6H_5CH=CH$—), benzoyl ($C_6H_5CO$), biphenyl (or diphenyl) ($C_{12}H_9$—), naphtyl ($C_{10}H_7$—) or tetrazolyl and n being an integer from 0 to 5;
Y represents H; $(C_1-C_{10})$alkyl; $(CO)(C_1-C_{10})$alkyl; aryl chosen from phenyl, benzyl, phenetyl, tolyl, xylyl, benzylidene or benzoyl;
X represents O, NH or CO;
when X represents O or NH,
then $B_1$ and $B_2$ are each independently H; $(C_1-C_{10})$alkyl; $CO(C_1-C_{10})$alkyl; $CF_3$; $(CH_2)_mNR_aR_b$; $P(O)(OH)_2$; $(CH_2)_pOCO(C_1-C_{10})$alkyl; $CO(CH_2)_pNR_aR_b$; $COCH[(CH_2)_nOH][NR_aR_b]$; $COCH[(CH_2)_nNR_aR_b][NR_aR_b]$; $COCH[(CH_2)_nNR_aR_b][NHCOR_a]$; $COCH[(C_1-C_{10})$alkyl]$[NR_aR_b]$; $COCH(R_d)NH(R_e)$; a divalent hydrocarbon radical (—CH—)$_n$ linked covalently to a cyclic or heterocyclic compound, saturated or unsaturated, chosen from cyclopropyl, cyclobutyl, cyclopentyl, cyclohexyl, morpholinyl, morpholinyl salt, piperazinyl, piperazinyl salt, phenyl, benzyl, phenetyl, tolyl, xylyl, benzylidene, benzoyl, biphenyl, naphtyl or tetrazolyl; sulfonate; carboxylate; one or more amino-acids, selected from Lysine or Serine;

with m being an integer from 2 to 5, p being an integer from 1 to 5, n being an integer from 0 to 5, $R_a$ and $R_b$ being each independently H, $(C_1-C_{10})$alkyl and $R_d$ and $R_e$ being each independently H, $(C_1-C_{10})$alkyl, $(CH_2)_n$ $NR_aR_b$, $COCH_3$, when at least one X represents CO, then $B_1$ and/or $B_2$ which is linked to said CO represents, independently, $(C_1-C_{10})$ alkyl; $OR_c$; $C_6H_5$; $(PO)(OH)_2$; a $(CH_2)_n$ group linked covalently to a cyclic or heterocyclic compound, saturated or unsaturated, chosen from cyclopropyl, cyclobutyl, cyclopentyl, cyclohexyl, morpholinyl, morpholinyl salt, piperazinyl, piperazinyl salt, phenyl, benzyl, phenetyl, tolyl, xylyl, benzylidene, benzoyl, biphenyl, naphtyl, tetrazolyl, thiophen, pyrrol, pyrazol, oxazol, thiazol, oxadiazol, thiadiazol, pyrimidine, pyrazine, pyridazine;

with $R_c$ being H, $(C_1-C_{10})$ alkyl, aryl chosen from phenyl, benzyl, phenetyl, tolyl, xylyl, benzylidene or benzoyl, and n being as defined previously, $B_3$, $B_4$, $B_5$ are each independently H; halogen chosen from F, I, C or Br; $(C_1-C_{10})$ alkyl; OR; CONHR'; $COOR_a$; CN; a divalent hydrocarbon radical $(—CH—)_n$ linked covalently to a cyclic or heterocyclic compound, saturated or unsaturated, chosen from cyclopropyl $(C_3H_5—)$, cyclobutyl $(C_4H_7—)$, cyclopentyl $(C_5H_9—)$, cyclohexyl $(C_6H_{11}—)$, morpholinyl

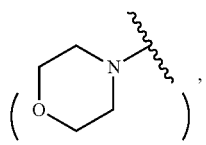, piperazinyl, piperazinyl salt

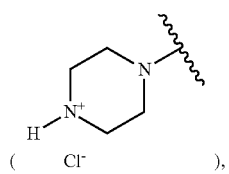 [SMILES: *N1CC[NH2+]CC1 ; [Cl-]], phenyl $(C_6H_5—)$, benzyl $(C_6H_5CH_2—)$, phenetyl $(C_6H_5CH_2CH_2—)$, tolyl $(C_6H_4CH_3—)$, xylyl $(C_6H_3(CH_3)_2—)$, benzylidene $(C_6H_5CH=CH—)$, benzoyl $(C_6H_5CO)$, biphenyl (or diphenyl) $(C_{12}H_9—)$, naphtyl $(C_{10}H_7—)$ or tetrazolyl

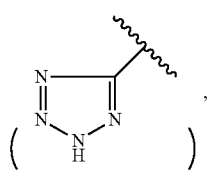

with R representing H, $(C_1-C_{10})$ alkyl, $CF_3$; R' representing H, $(C_1-C_6)$alkyl-$NH_2$, a divalent hydrocarbon radical $(—CH_2—)$ linked covalently to a cyclic or heterocyclic compound, saturated or unsaturated, chosen from cyclopropyl $(C_3H_5—)$, cyclobutyl $(C_4H_7—)$, cyclopentyl $(C_5H_9—)$, cyclohexyl $(C_6H_{11}—)$, morpholinyl

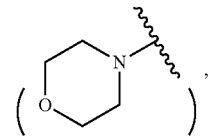, piperazinyl, piperazinyl salt

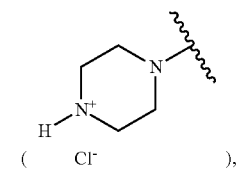, phenyl $(C_6H_5—)$, benzyl $(C_6H_5CH—)$, phenetyl $(C_6H_5CH_2CH—)$, tolyl $(C_6H_4CH_3—)$, xylyl $(C_6H_3(CH_3)_2—)$, benzylidene $(C_6H_5CH=CH—)$, benzoyl $(C_6H_5CO)$, biphenyl (or diphenyl) $(C_{12}H_9—)$, naphtyl $(C_{10}H_7—)$ or tetrazolyl

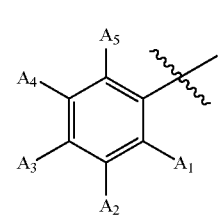;

$R_a$ and n being as defined previously, with the proviso that when X represents O, then $B_1$ and $B_2$ do not represent at the same time a $(C_1-C_{10})$ alkyl, and with the proviso that compound (I) is not the 4-(1,2-dihydro-6-(4-hydroxy-3-methoxyphenyl)-2-oxopyrimidin-4-yl)-2-methylbenzoic acid.

2. The compound according to claim 1, wherein A is a phenyl group having the following formula:

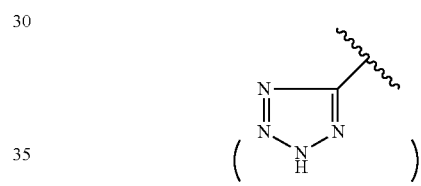

(A)

wherein $A_1$, $A_2$, $A_3$, $A_4$, $A_5$ are each independently H; halogen chosen from F, I, C or Br;

$(C_1-C_{10})$ alkyl; OR with R representing H, $(C_1-C_{10})$ alkyl, $CF_3$; CONHR' with R'=H, $(C_1-C_6)$alkyl-$NH_2$, a divalent hydrocarbon radical $(—CH_2—)$ linked covalently to a cyclic or heterocyclic compound, saturated or unsaturated, chosen from cyclopropyl $(C_3H_5—)$, cyclobutyl $(C_4H_7—)$, cyclopentyl $(C_5H_9—)$, cyclohexyl $(C_6H_{11}—)$, morpholinyl

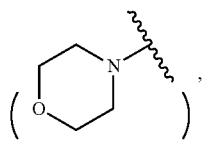

piperazinyl, piperazinyl salt

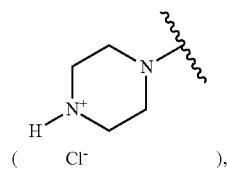 [SMILES: *N1CC[NH2+]CC1 ; [Cl-]]

phenyl ($C_6H_5$—), benzyl ($C_6H_5CH$—), phenetyl ($C_6H_5CH_2CH$—), tolyl ($C_6H_4CH_3$—), xylyl ($C_6H_3(CH_3)_2$—), benzylidene ($C_6H_5CH=CH$—), benzoyl ($C_6H_5CO$), biphenyl (or diphenyl) ($C_{12}H_9$—), naphtyl ($C_{10}H_7$—) or tetrazolyl

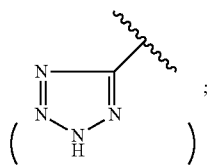

$COOR_a$ with $R_a$ representing H, ($C_1$-$C_{10}$)alkyl; $NR_aR'_a$ with $R_a$ and $R'_a$ representing independently H, ($C_1$-$C_{10}$)alkyl; CN; a divalent hydrocarbon radical (—$CH_2$—) linked covalently to a cyclic or heterocyclic compound, saturated or unsaturated, chosen from cyclopropyl ($C_3H_5$—), cyclobutyl ($C_4H_7$—), cyclopentyl ($C_5H_9$—), cyclohexyl ($C_6H_{11}$—), morpholinyl

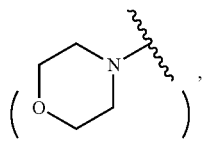

piperazinyl, piperazinyl salt

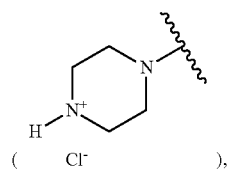 [SMILES: *N1CC[NH2+]CC1 ; [Cl-]]

phenyl ($C_6H_5$—), benzyl ($C_6H_5CH$—), phenetyl ($C_6H_5CH_2CH_2$—), tolyl ($C_6H_4CH_3$—), xylyl ($C_6H_3(CH_3)_2$—), benzylidene ($C_6H_5CH=CH$—), benzoyl ($C_6H_5CO$), biphenyl (or diphenyl) ($C_{12}H_9$—), naphtyl ($C_{10}H_7$—) or tetrazolyl

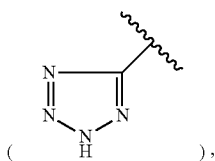

and n being an integer from 0 to 5.

3. The compound of formula (I) according to claim 2, wherein:

$A_1$, $A_2$, $A_4$, $B_4$, $B_5$ and Y represent H.

4. The compound of formula (I) according to claim 3, wherein:

$A_3$, $A_5$ and $B_3$ are each independently H; a halogen chosen from F, I or Cl; an alkyl radical chosen from methyl, ethyl or isopropyl; an OR group chosen from OH, $OCH_3$, $OC_2H_5$ or $OCF_3$; COOH; CN; a cyclic or heterocyclic compound chosen from cyclohexyl, morpholinyl, piperazinyl, piperazinyl salt or tetrazolyl;

when X represents O or NH, then $B_1$ and $B_2$ are each independently H; methyl, ethyl; $COCH_3$; $COCH(CH_3)_2$; $CF_3$; $CH_2$—$CH_2$—$NH_2$, $CH_2$—$CH_2$—$NH_3^+$ $Cl^-$; $P(O)(OH)_2$, $P(O)(ONa)_2$; $CH_2OCOCH_3$; $COCH[(CH_2)OH][NH_3^+$ $Cl^-]$; COCH $[(CH_2)_4NH_3^+$ $Cl^-][NH_3^+$ $Cl^-]$; $SO_3$—$Na^+$; COCH $[(CH_2)_4NH_3^+$ $Cl^-][NHCOCH_3]$; $COCH[(CH(CH_3)_2]$ $[NH_3^+$ $Cl^-]$; a hydrocarbon radical (—$CH_2$—)$_n$ linked covalently to a cyclic or heterocyclic compound, saturated or unsaturated, chosen from

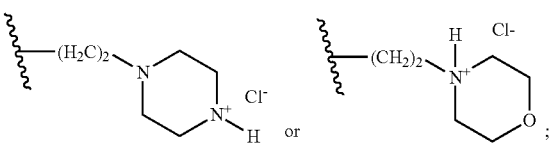

n being as defined previously, when at least one X represents CO, then $B_1$ and/or $B_2$ which is linked to said CO represents, independently, methyl, ethyl; OH, $OCH_3$, $OC_6H_5$; $C_6H_5$; $(PO)(OH)_2$; a hydrocarbon radical (—$CH_2$—)$_n$ linked covalently to a cyclic or heterocyclic compound, saturated or unsaturated, chosen from

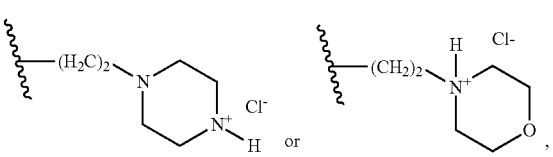

n being as defined previously.

5. The compound according to claim 1, wherein X represents O, $B_1$ represents a ($C_1$-$C_{10}$) alkyl and $B_2$ represents H.

6. The compound according to claim 4, which is selected from the group comprising compounds of formula (I) wherein:

$A_1=A_2=A_4=B_4=B_5=Y=H$, and

X=O, $A_5=B_3=H$, $A_3=Cl$, $B_1=CH_3$, $B_2=H$ (1),
X=O, $A_5=B_3=H$, $A_3=OCH_3$, $B_1=CH_3$, $B_2=H$ (2),
X=O, $A_5=B_3=H$, $A_3=OH$, $B_1=CH_3$, $B_2=H$ (3),

X=O, $A_5$=$B_3$=H, $A_3$=CH(CH$_3$)$_2$, $B_1$=CH$_3$, $B_2$=H (4),
X=O, $A_5$=$B_3$=H, $A_3$=F, $B_1$=CH$_3$, $B_2$=H (5),
X=O, $A_5$=$B_3$=H, $A_3$=I, $B_1$=CH$_3$, $B_2$=H (6),
X=O, $A_5$=Cl, $A_3$=$B_3$=H, $B_1$=CH$_3$, $B_2$=H (7),
X=O, $A_5$=$A_3$=$B_3$=H, $B_1$=CH$_3$, $B_2$=H (8),
X=O, $A_5$=$A_3$=OCH$_3$, $B_3$=H, $B_1$=CH$_3$, $B_2$=H (11),
X=O, $A_3$=OCF$_3$, $A_5$=$B_3$=H, $B_1$=CH$_3$, $B_2$=H (12),
X=O, $A_3$=OCH$_2$CH$_3$, $A_5$=$B_3$=H, $B_1$=CH$_3$, $B_2$=H (13),
X=O, $A_5$=OCH$_3$, $A_3$=$B_3$=H, $B_1$=CH$_3$, $B_2$=H (14),
X=O, $A_3$=CN, $A_5$=$B_3$=H, $B_1$=CH$_3$, $B_2$=H (15),
X=O, $A_3$=cyclohexyl, $A_5$=$B_3$=H, $B_1$=CH$_3$, $B_2$=H (16),
X=O, $A_3$=Cl, $A_5$=H, $B_3$=OCH$_3$, $B_1$=CH$_3$, $B_2$=H (17),
X=O, $A_3$=tetrazolyl, $A_5$=$B_3$=H, $B_1$=CH$_3$, $B_2$=H (18),
X=O, $A_3$=morpholinyl, $A_5$=$B_3$=H, $B_1$=CH$_3$, $B_2$=H (19),
X=O, $A_3$=piperazinyl salt

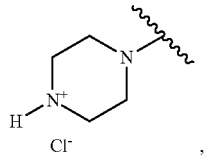

$A_5$=$B_3$=H, $B_1$=CH$_3$, $B_2$=H (21),
X=O, $A_3$=COOH, $A_5$=$B_3$=H, $B_1$=CH$_3$, $B_2$=H (22),
X=O, $A_3$=methyl-piperazinyl

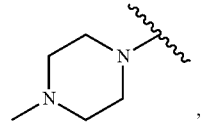 [SMILES: *N1CCN(C)CC1]

$A_5$=$B_3$=H, $B_1$=CH$_3$, $B_2$=H (24),
and their mixtures.

7. The compound of formula (I) according to claim 4, wherein:
$A_1$=$A_2$=$A_5$=$B_3$=$B_4$=$B_5$=Y=H, and
X=O, $A_4$=CH$_3$, $A_3$=OH, $B_1$=CH$_3$, $B_2$=H (59).

8. The compound according to claim 4, which is selected from the group comprising compounds of formula (I) wherein:
$A_1$=$A_2$=$A_4$=$B_4$=$B_5$=Y=H, and
X=O, $A_5$=$B_3$=H, $A_3$=Cl, $B_1$=CF$_3$, $B_2$=H (9),
X=O, $A_5$=$B_3$=H, $A_3$=Cl, $B_1$=H, $B_2$=CH$_3$ (10),
X=O, $A_3$=Cl, $A_5$=$B_3$=H, $B_1$=CH$_3$, $B_2$=PO(ONa)$_2$ (20),
X=O, $A_3$=C, $A_5$=$B_3$=H, $B_1$=CH$_2$CH$_2$NH$_3$$^+$ Cl$^-$, $B_2$=H (23),
X=O, $A_3$=Cl, $A_5$=$B_3$=H, $B_1$

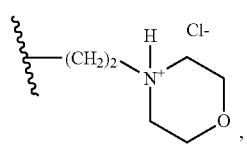

$B_2$=H (25),
X linked to $B_1$ represents O and X linked to $B_2$ represents NH, $A_3$=Cl, $A_5$=$B_3$=H, $B_1$=CH$_3$, $B_2$=COCH$_3$ (26),
X linked to $B_1$ represents O and X linked to $B_2$ represents CO, $A_3$=C, $A_5$=$B_3$=H, $B_1$=CH$_3$, $B_2$=OH (27),
and their mixtures.

9. The compound of general formula (I) according to claim 6, which is more particularly selected from the group comprising compounds (1), (2), (3), (5), (7), (8), (9) and their mixture.

10. The compound of general formula (I) according to claim 1, which is selected from the group comprising compounds of formula (I) wherein:
X=O, $B_3$=$B_4$=$B_5$=Y=H, $B_1$=CH$_3$, $B_2$=H, and
A represents

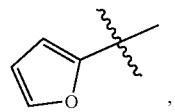

(28)

A represents

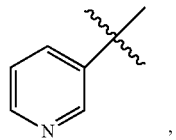

(29)

A represents

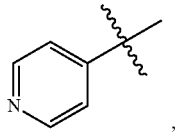

(30)

A represents

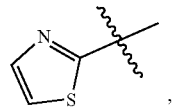

(31)

A represents

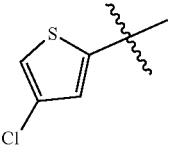

(32)

A represents
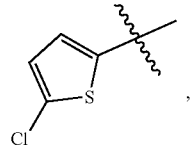 (33)
A represents
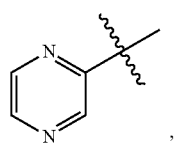 (34)
A represents
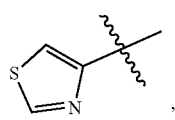 (35)
A represents
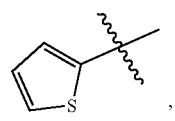 (36)
A represents
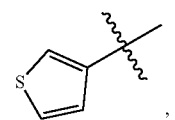 (37)
A represents
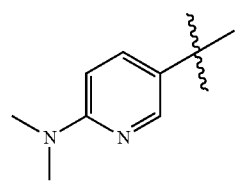 (38)
A represents
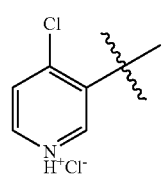 (39)
A represents
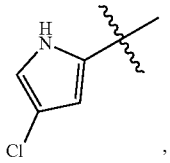 (40)
A represents
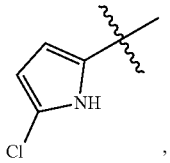 (41)
A represents
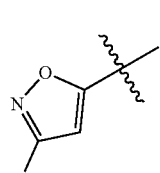 (42)
A represents
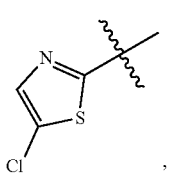 (43)
A represents
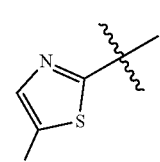 (44)

A represents

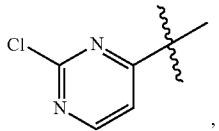 (45)

A represents

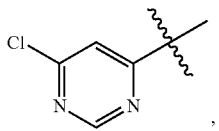 (46)

A represents

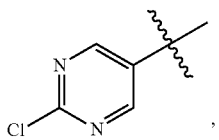 (47)

A represents

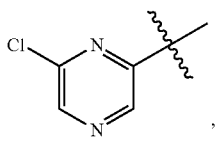 (48)

A represents

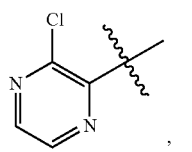 (49)

A represents

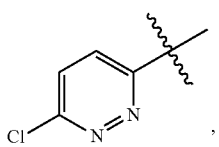 (50)

A represents

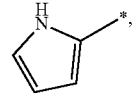 (60)

and their mixtures.

11. A method of inhibiting the biological activity of CXCL12 in a subject comprising administering to the subject a compound of general formula (I) according to claim 1.

12. The method according to claim 11 wherein the method is for the prevention and/or treatment of a disease in the subject chosen from the group comprising inflammation and inflammatory diseases, immune and auto-immune diseases, pain-related diseases, genetic diseases and/or cancer.

13. The method according to claim 12, wherein the disease is chosen in the group comprising asthma, atopic dermatitis, allergic rhinitis, atopic conjunctivitis, rhinoconjunctivitis, chronic obstructive pulmonary disease (COPD), lupus, Sjögren syndrome, hyperalgesia/pain, pulmonary hypertension (PH), obliterative bronchiolitis, chronic lung allograft diseases, rhumatoid arthritis, inflammatory bowel disease, WHIM syndrome (Warts, Hypogammaglobulinemia, Immunodeficiency and Myelokathexis syndrome), hypereosinophilic syndromes, eosinophilic bronchiolitis, Churg-Strauss syndrome, and eosinophilic granulomatosis with polyangeiitis.

14. A pharmaceutical composition comprising at least a compound of formula (I) according to claim 1, and optionally a pharmaceutically acceptable excipient or carrier.

15. The pharmaceutical composition according to claim 14, comprising a pharmaceutically acceptable excipient or carrier.

16. A method for the prevention and/or treatment of a disease in a subject chosen from the group comprising asthma, atopic dermatitis, allergic rhinitis, atopic conjunctivitis, rhinoconjunctivitis, chronic obstructive pulmonary disease (COPD), lupus, Sjögren syndrome, hyperalgesia/pain, pulmonary hypertension (PH), obliterative bronchiolitis, chronic lung allograft diseases, rhumatoid arthritis, inflammatory bowel disease, WHIM syndrome (Warts, Hypogammaglobulinemia, Immunodeficiency and Myelokathexis syndrome), hypereosinophilic syndromes, eosinophilic bronchiolitis, Churg-Strauss syndrome, and eosinophilic granulomatosis with polyangeiitis comprising administering the pharmaceutical composition of claim 14 to the subject.

* * * * *